US011220695B2

(12) United States Patent
de Godoy Lusso et al.

(10) Patent No.: US 11,220,695 B2
(45) Date of Patent: Jan. 11, 2022

(54) COMPOSITIONS AND METHODS FOR PRODUCING TOBACCO PLANTS AND PRODUCTS HAVING ALTERED ALKALOID LEVELS WITH DESIRABLE LEAF QUALITY

(71) Applicant: Altria Client Services LLC, Richmond, VA (US)

(72) Inventors: Marcos Fernando de Godoy Lusso, Chesterfield, VA (US); James A Strickland, Richmond, VA (US); Jesse Frederick, Richmond, VA (US); Dongmei Xu, Glen Allen, VA (US); Chengalrayan Kudithipudi, Midlothian, VA (US)

(73) Assignee: ALTRIA CLIENT SERVICES LLC, Richmond, VA (US)

( * ) Notice: Subject to any disclaimer, the term of this patent is extended or adjusted under 35 U.S.C. 154(b) by 0 days.

(21) Appl. No.: 16/291,878

(22) Filed: Mar. 4, 2019

(65) Prior Publication Data

US 2019/0271000 A1 Sep. 5, 2019

Related U.S. Application Data

(60) Provisional application No. 62/638,928, filed on Mar. 5, 2018.

(51) Int. Cl.
*C12N 15/82* (2006.01)
*A24B 13/00* (2006.01)

(52) U.S. Cl.
CPC .......... *C12N 15/8225* (2013.01); *A24B 13/00* (2013.01); *C12N 15/8218* (2013.01); *C12N 15/8243* (2013.01); *C12N 15/8261* (2013.01)

(58) Field of Classification Search
None
See application file for complete search history.

(56) References Cited

U.S. PATENT DOCUMENTS 4,516,590 A 5/1985 Teng
4,528,993 A 7/1985 Sensabaugh, Jr. et al.
4,660,577 A 4/1987 Sensabaugh, Jr. et al.
4,732,856 A 3/1988 Federoff
4,762,785 A 8/1988 Comai
4,848,373 A 7/1989 Lenkey
4,945,050 A 7/1990 Sanford et al.
4,987,907 A 1/1991 Townend
5,004,863 A 4/1991 Umbeck
5,013,658 A 5/1991 Dooner et al.
5,104,310 A 4/1992 Saltin
5,141,131 A 8/1992 Miller, Jr. et al.
5,149,645 A 9/1992 Hoekema et al.
5,159,135 A 10/1992 Umbeck
5,177,010 A 1/1993 Goldman et al.
5,231,019 A 7/1993 Paszkowski
5,316,931 A 5/1994 Donson et al.
5,372,149 A 12/1994 Roth et al.
5,463,174 A 10/1995 Moloney et al.
5,464,763 A 11/1995 Schilperoort et al.
5,469,976 A 11/1995 Burchell
5,491,081 A 2/1996 Webb
5,563,055 A 10/1996 Townsend et al.
5,589,367 A 12/1996 Donson et al.
5,659,026 A 8/1997 Baszczynski et al.
5,689,035 A 11/1997 Webb
5,789,156 A 8/1998 Bujard et al.
5,814,618 A 9/1998 Bujard et al.
5,866,785 A 2/1999 Donson et al.
5,879,918 A 3/1999 Tomes et al.
5,886,244 A 3/1999 Tomes et al.
5,889,190 A 3/1999 Donson et al.
5,889,191 A 3/1999 Turpen
5,932,782 A 8/1999 Bidney
5,981,840 A 11/1999 Zhao et al.
6,072,050 A 6/2000 Bowen et al.
8,124,851 B2 2/2012 Dewey et al.
8,319,011 B2 11/2012 Xu et al.
8,791,329 B2 * 7/2014 Hashimoto ............ A24B 15/20 800/285

(Continued)

FOREIGN PATENT DOCUMENTS

WO WO 2011/027315 3/2011
WO WO 2018/067985 4/2018

OTHER PUBLICATIONS

DeBoer et al. RNAi-mediated down-regulation of ornithine decarboxylase (ODC) leads to reduced nicotine and increased anatabine levels in transgenic Nicotiana tabacum L. Phytochemistry. Apr. 2011;72(4-5):344-55. Epub Jan. 11, 2011. (Year: 2011).*
Williamson et al. Differential Accumulation of a Transcript Driven by the CaMV 35S Promoter in Transgenic Tobacco. Plant Physiol. Aug. 1989;90(4):1570-6. (Year: 1989).*
Kano-Murakami Y. et al. A rice homeotic gene, OSH1, causes unusual phenotypes in transgenic tobacco. FEBS Lett. Nov. 22, 1993; 334(3):365-8. (Year: 1993).*

(Continued)

*Primary Examiner* — Cynthia E Collins
(74) *Attorney, Agent, or Firm* — Arnold & Porter Kaye Scholer LLP

(57) ABSTRACT

The present disclosure includes methods and compositions for improving leaf quality in low-alkaloid tobacco plants, e.g., by combining inducible promoters and non-coding RNAs for suppression of an ornithine decarboxylase (ODC) gene. Also provided are low alkaloid tobacco plants with normal, suppressed, or otherwise altered polyamine levels. Further provided are tobacco plants with altered total alkaloid, nicotine levels, commercially acceptable leaf grade, their development via breeding or transgenic approaches, and production of tobacco products from these tobacco plants.

18 Claims, 6 Drawing Sheets

Specification includes a Sequence Listing.

(56) References Cited

U.S. PATENT DOCUMENTS

| | | | |
|---|---|---|---|
| 9,187,759 | B2 | 11/2015 | Dewey et al. |
| 9,228,194 | B2 | 1/2016 | Dewey et al. |
| 9,228,195 | B2 | 1/2016 | Dewey et al. |
| 9,247,706 | B2 | 2/2016 | Dewey et al. |
| 2004/0118422 | A1 | 6/2004 | Lundin et al. |
| 2005/0178398 | A1 | 8/2005 | Breslin et al. |
| 2006/0191548 | A1 | 8/2006 | Strickland et al. |
| 2007/0240728 | A1 | 10/2007 | Hashimoto et al. |
| 2008/0120737 | A1 | 5/2008 | Hashimoto et al. |
| 2017/0233756 | A1 | 8/2017 | Begemann et al. |
| 2018/0119163 | A1 | 5/2018 | Kudithipudi et al. |

OTHER PUBLICATIONS

McGinnis. RNAi for functional genomics in plants. Brief. Funct. Genomics. Mar. 2010;9(2):111-7. Epub Jan. 6, 2010. (Year: 2010).*

Sandler et al. Inhibition of gene expression in transformed plants by antisense RNA. Plant Molecular Biology, 1988, vol. 11, No. 3, pp. 301-310. (Year: 1988).*

Van der Meer et al. Antisense inhibition of flavonoid biosynthesis in petunia anthers results in male sterility. Plant Cell. Mar. 1992;4(3):253-620. (Year: 1992).*

Anwar et al., "Polyamine Interactions with Plant Hormones: Cross-talk at Several Levels," In: Kusano T., Suzuki H. (eds) *Polyamines*, Springer, Tokyo 22:267-302 (2015).

Baldwin, "The alkaloidal responses of wild tobacco to real and simulated herbivory," *Oecologia*, 77: 378-381 (1988).

Bowman et al., "Revised North Carolina Grade Index for Flue-Cured Tobacco," *Tobacco Science*, 32:39-40 (1988).

Cermak et al., " Efficient Design and Assembly of Custom TALEN and Other TAL Effector-Based Constructs for DNA Targeting/" *Nucleic Acids Research*, 39:e82 (2011).

Collins et al., "Determination of Nicotine Alkaloids in Tobacco Using the Autoanalyzer," *Tobacco Science* 13:79-81 (1969).

Chaplin JF, Weeks WW (1976). Association between percent total alkaloids and other traits in flue-cured tobacco. Crop Sci. 16: 416-418.

Chaplin JF et al., "Agronomic, chemical, and smoke characteristics of flue-cured tobacco lines with different levels of total alkaloids," *Crop Sci*. 75: 133-136 (1983).

Christensen et al., "Sequence Analysis and Transcriptional Regulation by Heat Shock of Polyubiquitin Transcripts from Maize," *Plant Mol. Biol*., 12:619-632 (1989).

Christensen et al., "Maize Polyubiquitin Genes: Structure, Thermal Perturbation of Expression and Transcript Splicing, and Promoter Activity Following Transfer to Protoplasts by Electroporation," *Plant Mol. Biol*., 18:675-689 (1992).

Christou et al., "Stable Transformation of Soybean Callus by DNA-Coated Gold Particles," *Plant Physiol*., 87:671-674 (1988).

Crossway et al., "Micromanipulation Techniques in Plan Biotechnology," *Biotechniques*, 4:320-334 (1986).

Dalton et al "Effects of down-regulating ornithine decarboxylase upon putrescine-associated metabolism and growth in Nicotiana tabacum L.," J. Exp. Bot. 67: 3367-3381 (2016).

Davis, "A Combined Automated Procedure for the Determination of Reducing Sugars and Nicotine Alkaloids in Tobacco Products Using a New Reducing Sugar Method," *Tobacco Science*, 20:139-144 (1976).

Davis et al., "Tobacco, Production, Chemistry and Technology", Blackwell Publishing, Article, "Chapters 4B and 4C", pp. 70-103 (1999).

DeBoer KD, Dalton HL, Edward FJ, Hamill JD Nicotiana tabacum L. *Phytochem*. 72:344-355 (2011).

DeBoer et al., "RNAi-mediated Down-regulation of Ornithine Decarboxylase (ODC) Impedes Wound-stress Stimulation of anabasine Synthesis in Nicotiana glauca," *Phytochem*. 86: 21-28 (2013).

De Wet et al., "The Experimental Manipulation of Ovule Tissues," ed. Chapman et al. (Longman, N.Y.), pp. 197-209 (1985).

Dewey et al., "Molecular genetics of alkaloid biosynthesis in *Nicotiana tabacum," Phytochemistry*, 94:10-27 (2013).

D'Halluin et al., "Transgenic Maize Plants by Tissue Electroporation," *Plant Cell*, 4:1495-1505 (1992).

Doyle et al.,. "TAL Effector-Nucleotide Targeter (TALE-NT) 2.0: Tools for TAL Effector Design and Target Prediction," *Nucleic Acids Research*, 40:W117-122 (2012).

Fariduddin et al., "Polyamines: Potent Modulators of Plant Responses to Stress," *J. Plant Interac*., 8:1-16 (2013).

Fedoroff et al., "Cloning of the Bronze Locus in Maize by a Simple Procedure Using the Transposable Controlling Element *Activator* (*Ac*)," *Proc. Natl. Acad. Sci. USA*, 81:3825-3829(1984).

Finer et al., "Transformation of Soybean Via Particle Bombardment of Embryogenic Suspension Culture Tissue," *In Vitro Cell Dev. Biol*., 27P:175-182 (1991).

Fluhr R, Mattoo AK. Ethylene—biosynthesis and perception. *Crit. Rev. Plan Sci*. 15:479-523 (1996).

Gaj et al., "ZFN, TALEN and CRISPR/Cas-based methods for genome engineering," *Trends in Biotechnology*, 31(7):397-405 (2013)

Gatz et al., "Regulation of a modified CaMV 35S promoter by the Tnl0-encoded Tet repressor in transgenic tobacco," *Mol. Gen. Genet*., 227:229-237 (1991).

Harpaz-Saad et al., "The Formation of ACC and Competition Between Polyamines and Ethylene for SAM," *Annu. Plant Reviews*, 44: 53-81 (2012).

Hibi et al., "Putrescine N-Methyltransferase in Cultured Roots of *Hyoscyamus albus," Plant Physiology* 100: 826-35 (1992).

Hildreth et al., "Tobacco nicotine uptake permease (NUP1) affects alkaloid metabolism," Proc. Natl. Acad. Sci. USA 108: 18179-18184 (2011).

Hildering et al., "Chimeric Structure of the Tomato Plant After Seed Treatment with EMS and X-Rays," *Pergamon press*, pp. 317-320 (1965).

Hoekema et al., "A binary plant vector strategy based on separation of vir- and T-region of the *Agrobacterium tumefaciens* Ti-plasmid," *Nature*, 303:179-180 (1983).

Kaeppler et al., "Silicon carbide fiber-mediated stable transformation of plant cells," *Plant Cell Reports* 9:415-418 (1990).

Kaeppler et al., "Silicon carbide fiber-mediated stable uansformation of plant cells," *Theor. Appl. Genet*. 84:560-566 (1992).

Kessler et al. "Plant responses to insect herbivory: the emerging molecular analysis," *Annu Rev. Plant Biol*., 53: 299-328 (2002).

Kidd et al., "The A and B loci in Tobacco Regulate a Network of Stress Response Genes, few of which are Associated with Nicotine Biosynthesis," *T. Plant Mol. Biol*., 60: 699-716 (2010).

Kushad et al., "Interrelationship of Polyamine and Ethylene Biosynthesis During Avoado Fruit Development and Ripening," *Plant Physiol*., 87:463-467 (1988).

Last et al., "pEmu: An Improved Promoter for Gene Expression in Cereal Cells," *Theor. Appl. Genet*., 81:581-588 (1991).

Legg et al., "Inheritance of Percent Total Alkaloids in *Nicotiana tabacum," L. J. Hered*., 60:213-217(1969)

Legg et al., "Registration of LA Burley 21 Tobacco Gerplasm," *Crop. Sci*., 10:212(1970).

Legg et al., "Inheritance of Per Cent Total Alkaloids in *Nicotiana tabacum* L. II. Genetic Effects of two Loci in Burley 21 x LA Burley 21 Populations," Can. J. Genet. Cytol. 13: 287-291 (1971).

Lester, "Polyamines and their cellular anti-senescence properties in honey dew muskmelon fruit," Plant Sci. 160: 105-112 (2000).

Mattoo et al., "Higher polyamines restore and enhance metabolic memory in ripening fruit," *Plant Sci*., 174: 3 86-3 93 (2008).

McCabe et al., "Stable Transformation of Soybean (*Glycine Max*) by Particle Acceleration," *Biotechnology*, 6:923-926 (1998).

McCallum et al., "Targeting Induced Local Lesions IN Genomes (TILLING) for Plant Functional Genomics," *Nat. Biotechnol*., 18:455-457 (2000).

McNellis et al., "Glucocordticoid-Inducible Expression of a Bacterial Avirulence Gene in Transgenic *Arabidopsis* Induces Hypersensitive Cell Death," *Plant J*., 14(2):247-257 (1998).

Mehta et al., "Engineered Polyamine Accumulation in Tomato Enhances Phytonutrient Content, Juice Quality, and Vine Life," *Nat. Biotechnol*., 20: 613-618 (2002).

Miller et al., "A Grade Index for Type 22 and 23 Fire-Cured Tobacco," *Tobacco Intern*., 192:55-57 (1990).

(56) References Cited

OTHER PUBLICATIONS

Morilla et al., "Free Polyamine Contents and Decarboxylase Activities duing Tomato Development and Ripening," *J. Agri. Food Chem.*, 44: 2608-2611 (1996).
Morita et al., "Vacuolar Transport of Nicotine is Mediated by a Multidrug and Toxic Compound Extrusion (MATE) Transporter in *Nicotiana tabacum," PNAS*, 106:2447-52 (2009).
Nambeesan et al., "Overexpression of Yeast Spermidine Synthase Impacts Ripening, Senscence and Decay Symptoms in Tomato," *The Plant Journal*, 63(5):836-847 (2010).
Nölke et al., "Polyamines Delay Leaf Maturation in Low-alkaloid Tobacco Varieties," *Plant Direct*, 2:1-12 (2018) <https://onlinelibrary.wiley.com/doi/epdf/10.1002/pld3.77>.
Odell et al., "Identification of DNA Sequences Required for Activity of the Cauliflower Mosaic Virus 35S Promoter," *Nature*, 313:810-812 (1985).
Onkokesung et al., "MYB8 Controls Inducible Phenolamide Levels by Activating Three Novel Hydroxycinnamoyl-Coenzyme A: Polyamine Transferases in Nicotiana attenuate," *Plant Physiology* 158 (1) 389-407 (2012).
Paszkowski et al., "Direct Gene Transfer to Plants," *EMBO J.*, 3:2717-2722.
Poehlman, "Breeding Field Crops," Van Nostrand Reinhold, New York(3.sup.rded), (1987).
Piotrowski et al., "Plant C-N Hydrolases and the Identification of a Plant N-Carbamoylputrescine Amidohydrolase Involved in Polyamine Biosynthesis," *J. Biol. Chem.*, 278:1708-1712 (2003).
Porta et al., "Use of Viral Replicons for the Expression of Genes in Plants," (1996) *Molecular Biotechnology*, 5:209-221.
Riggs et al., "Stable Transformation of Tobacco by Electroporation: Evidence for Plasmid Concatenation," *Proc. Natl. Acad. Sci. USA*, 83:5602-5606(1986).
Saftner et al., "Polyamine Levels and Tomato Fruit Development: Possible Interaction with Ethylene," *Plant Physiol.*, 92:547-550 (1990).
Saitoh et al., "The Alkaloid Contents of Sixty Nicotiana Species," *Phytochem.*, 24: 477-480(1985).
Schena et al., "A Steroid-Inducible Gene Expression System for Plant Cells," *Proc. Natl. Acad. Sci. USA*, 88:10421-10425 (1991).
Serafini-Fracassini, et al., "Spermine Delays Leaf Senescence in Lactuca sativa and Prevents the Decay of Cholorplast Photosystems," *Plant Physiol. Biochem*, 48:602-611 (2010).
Shillito et al., "[19] Direct Transfer to Protoplasts of Dicotyledonous and Monocotyledonous Plants by a Number of Methods Including Electroporation," *Meth. Enzymol.*, 153:313-336 (1987).
Shoji et al. Clustered Transcription Factor Genes Regulate Nicotine Biosynthesis in Tobacco, *The Plant Cell*, 22:3390-3409 (2010)
Shoji, "Stress-induced Expression of NICOTINE2-locus Genes and their Homologs Encoding Ethylene Response Factor Transcription Factors in Tobacco," *Phytochem.*, 113:41-49 (2015).
Singh et al., "Cytological Characterization of Transgenic Soybean," *Theor. Appl. Genet.*, 96:319-3 24(1998).
Sobieszczuk-Nowicka, et al., "From Accumulation to Degradation: Reprogramming Polyamine Metabolism Facilitates Dark-Induced Senescence in Barley Leaf Cells," *Front. Plant Sci.*, 6(1196):1-14 (2016).
Tiburcio et al., "The Roles of Polyamines During the Lifespan of Plants: From Development to Stress," *Planta*, 240:1-18 (2014).
Tomes et al., "16 Direct DNA Transfer into Intact Plant Cells Via Microprojectile Bombardment," *Plant Cell, Tissue, and Organ Culture*, pp. 197-198 (1995).
Velten et al., "Isolation of a Dual Plant Promoter Fragment from the Ti Plasmid of *Agrobacterium tumefaciens" The EMBO Journal*, 3:2723-2730 (1984).
Verkerk, "Chimerism of the Tomato Plant After Seed Irradiation wit Fast Neutrons," *Neth. J. Agric. Sci.*, 19:197-203 (1971).
Wang et al., Generation of Tobacco Lines with Widely Different Reduction in Nicotine Levels Via RNA Silencing Approaches, *J. Biosci.*, 3 3(2) 177-184 (2008).
Wang et al., "Nicotine Concentration in Leaves of Flue-cured Tobacco Plants as Affected by Removal of the Shoot Apex and Lateral Buds," *Integr. Plant Biol.*, 50:958-964 (2008).
Weising et al., Foreign Genes in Plants: Transfer, Structue, Expression, and Applications, *Ann. Rev. Genet.*, 22:421-477 (1988).
Wernsman, E. A., and Ruffy, R. C., "Tobacco," Chapter 17, pp. 669-698. In: Cultivar Development. Crop Species. W. H. Fehr (ed.), MacMillan Publishing Co., Inc., New York, N.Y. (1987).

* cited by examiner

Leaf PA content (nmol g-1 FW)
250
200
150
100
50
0
NA
HI
LI
LA
Before flowering
Topping
Harvest
Leaf 6
Leaf 23
F Put
F Spd
F Spm
C Put
C Spd
C Spm Root PA content (nmol g-1 FW)
Not analyzed DL-[1-14C]-arginine
NA
LA
14CO2 (nmol h-1 g-1 FW)
80
60
40
20
0
**
*
Topping
Harvest
Topping
Harvest
Leaves
Roots L-[1-14C]-ornithine
NA
LA
14CO2 (nmol h-1 g-1 FW)
60
40
20
0
*
**
**
Topping
Harvest
Topping
Harvest
Leaves
Roots

SEQUENCE LISTING

```
<160> NUMBER OF SEQ ID NOS: 36

<210> SEQ ID NO 1
<211> LENGTH: 2001
<212> TYPE: DNA
<213> ORGANISM: Nicotiana sp.

<400> SEQUENCE: 1

cttttaccta aacttaaata ttggccttat gcacgggcat caactcgcgt attactaaga     60

agaaagaaga acggctcctc gtctcccatg tcggcctctg gaactcttaa tataaccgcc    120

gacagacaaa accggctggt ctctcactgt ttcttatcct cagaattatt atgaacataa    180

actaaagtac ctatctcttg ttttctcatt tcacaccatt tttttcttca cttcacactt    240

ggtctcaatc aaataaaaaa cagcaaccgc cttagcttgt tgtcttcttc actactccac    300

ttgtccctag agttccccaa aaatatcaag ctaagaaaaa gttaactaaa gaagagaata    360

tatgggagct gaggtttctt tcataagctg accgactctt tatttggcgg cgcttatttt    420

atttattact tcaaaagaaa agttcttttt gttttccttt tttataattt tcaactccca    480

acttgtgtgt gttgtctaaa tgtctatata taaatatgta tataacggtt tgtttaagaa    540

acttgcattg gtactggttt gttcttgtca accttcttga ctagtatata tattgtaaac    600

ttttgtgtct ctgtattgga gatttttgtt tgagttctct ttttgaatat tgcatgtgta    660

tttacaaggt ggcgaattca agagacaaaa tatctaacag gagaagacat gaagataggg    720

atagagatga taattataat gtgttggaat cgatgttttc gggtaatatt aatagggaac    780

aggagatgtc tgtaatggtt tctgcactaa aacatgttgt tgctggtgaa gatagattga    840

atcaccaaat cttgactgat gaaaatggtg cagctgagaa taatcttggt tcaggttttt    900

cttcagtttc ttgggggstt ggtgagaaaa gaggacgtga acaacggcaa agtagtcagc    960

aattcttaca tattggaagt tctgatatga gatcatcagg tatttttatt ttactttact   1020

tttttttttg aaaaaaatga caccgccgta aaaataataa ccgaaaaaag tgtataaaat   1080

ttgtataatt tttgcgttat atatatacat tctgtatgtt atatacaaaa attatacaaa   1140

tagttaacaa atttgtatat aaaaattata caaattttat acatttttcg gctaccacat   1200

ataaatagtt tctggcgccg gctaaaagtg ataatacccc tttttccttt aaagttttgg   1260

attttctttt agtttatgtt gtgttttcag tgggtatttt gaaaacataa ttaactagtg   1320

gccaatgtag cattatacgg attcaattga atccatagct ttcgaggcat aaaataaatt   1380

tatgtgtaaa atttcattaa agttataaga tatagtagaa tttgaaccca tataacagat   1440

atgaacccat aactttaaaa atacaatatg ttcaatgcta gaatcttaaa tgttcaaccc   1500

acaaaattta aattttggat ccgcctctga ttattaaaag tatattttct ctaacggttt   1560

aattaacatt tagataagat gatcaaacat taatactatg atattagagt gggtataagt   1620

tccgggctga agcttaaata tttagatgaa acagacacac aattcaatag tttggatgtg   1680

ttgcaggaat cattattgct aaataacagc taaatgtaga tgagaataaa tggattaaaa   1740

gatttggttg atcttctatg tgagttgtat tcattctgca ttttatttag aagtaaattg   1800
```

```
ctgcagatgc ctttgttttt agttttgatt cttgccattt tctccattaa aaaaatgcac   1860

ttgaaacata caatataaat caagtgtgtg acttttcact atattgattt ttagtacatt   1920

attaatgaaa gatacaatta ggtggatgtg tacgtgcttc attatcacat tttcattatt   1980

ttgaatagca gattttacac a                                              2001
```

<210> SEQ ID NO 2
<211> LENGTH: 2001
<212> TYPE: DNA
<213> ORGANISM: Nicotiana sp.

<400> SEQUENCE: 2

```
ttgtttatgt tgtatgtatt ggtttagtga gttatgatat aatgttttca ttgaaagtgt     60

gacatgatac gagtattttc aaatggacgt gagttagcat ttcagatttt cacttcattt    120

gtcctattta tattaaaccc acaaaatgaa aatacccgta tttatgttta tacactttca    180

taaatttcaa gaatttagac aaaaagattt agctttaaaa ttttgatatg gtaattttgt    240

acgctatttt aaaactatta tgttaatatt tatcctcttt tttaaatttc acaaaaataa    300

atacataaaa tatttatttg taatttttgt ttttctttta ataattacat tttaaaatac    360

ttagttatgg atatacctca tagggggtat aattaagtgt atgattttta taatataggg    420

ggtgtcagtg tttgatctta aaatacaaaa gggtgtatcc gaaactgaat cgtattatat    480

gggtgtttag tataattaac actattatat ataagtaata ttgatattta aatctccgca    540

cttaattaaa tactgtctcg taaaattaac gtctatgtgt actgacaata atgtaatatt    600

tttttaacct tgttataata ggtaatttgt attattttgg aattgatatc tctttttaa     660

tgaaaggtta catataatta tcatttagat gataagagcg tgcataaatt cattaacaat    720

atctaacata tagagggatg aagtagtact attaattttc taaaaaatga gaagcaaaaa    780

aggaatattc ttctatgtcg gcctctagct tagctaagaa ctcaacgccg actgacaaac    840

aactcctaaa gcggctctaa ttttttctct ctaaaatatt cttatccaca tataatagat    900

ctcccttcac acttactaat actgctgtcc tttattctct tcacattttg tccaaaagaa    960

ataatgacaa gtcaacaata aaaaacaatg ttttcatcaa caagattaat ctctccttct   1020

tacacgcaag caaagatgga tctagaattt gcggagatac atgaacaaac tgttcaacta   1080

gtgccaccca ggggcgaatt tataggtaaa tatatggggc acttgaacct attattttc    1140

catcaaacta agtattttat gtatatattt tttagaattg gtctagtatt atctgctgac   1200

actcatgctc caaaaaggct aaatggtgca cttggttgaa tattgaatta tttacctaaa   1260

ggactacgaa tcgaatctca cttaatactt tttttttcct cctttttaa tagtgcactc    1320

atattataaa aatcctatat ccgcctatga tgtcaccatc aaacttttga ttttaacggt   1380

tataagtaaa ttatatcatc gtttttaata tatatagaca aatattttaa aaaaaattgc   1440

cgatgtgtga cctctatctc ctagcatagg tccgccaact tggagagaag aatacaaatt   1500

aaggaagctc atgagctgac tagccgactc tatattcttg tctttattat tttacaaaaa   1560

agtttgactt tactttttg ttttttgtt ttaagtaaat tttcaactcc caacttaggt    1620

tagtctaagt ctctatatat ataacggttg gttcaagaaa gcctaaaaaa gagggggtta   1680

gctggttggt ataattagtt tgttcatctt gtcaactttc ttgaaaagca aaagttttta   1740

atattttgtt ttcctctttt tgaatcttga agtttgattc aaacttctca ttttatagaa   1800

tactctgtta agacttttta gttagtatag tatactagct atatactaga ttaactttt    1860
```

```
tttttttatt tataaagtcc cttaatttag tgaagttttg ttacatgtgt atactcaagg   1920

tggcaaattt tagaaacaaa gccatttata agccaataag agatgatgtg atgttttctg   1980

ggattaatag agaagaggag a                                               2001
```

<210> SEQ ID NO 3
<211> LENGTH: 2001
<212> TYPE: DNA
<213> ORGANISM: Nicotiana sp.

<400> SEQUENCE: 3

```
aggagcgttc aaagtttaga tgatttatta tggtatatgt gcatttttca ccacttgttg     60

ccaatataat actacatttt cctctcgaga cgacaaagaa tgataatgaa gataccttttt   120

cttgctgaag attttgtcag tatactgcaa ctgattttag caactttgct cttcatatta    180

taagtcaatt atatactgtc gaatctttct attgtttaat cagtcgcccc tcatgcatgt    240

aaattaaagt ataatatata taaagtataa cttgaatgtg gatttttccc ccacatatat    300

aataaaacaa tgaaaggaaa agatctatat atgtgtcttt gatttttagt gggccaaaca    360

aaaaaaaaag aagcagcaat atgtcagtat tcaggagaaa ttcaaaaata gtcagattta    420

caactgatca ttcaaaaata gttcagtttc aaaagtaatc aaaatttagc cacttttcat    480

gtaaagataa aaaagagcga aaatattgtt caaaacccga aaaatacgcc agtatattat    540

actggagttc aagtataagt atgcttgaac tccaacatat tatattggag ttccaggata    600

agtatgttgg aactccagca taatatgatg gagttccaac ataagtacac tagaactcta    660

gcataatata ctggagtttc agcaagtata attgtccagt ataatatact ggagtttgga    720

gcacaagtgc tccagtctcc agtatattaa taatggagtc agcaaagtat accggtccag    780

cataatatgc tggagttcat acacaggtgc accgaaatcc agtatattat gctggaccgg    840

tctctgttgc agcaaaatag tggctatttt tcattgactt tgtaaacact gactattttt    900

gaatgaccag tccgaaaact agctataccg tgctattttt acatgaaaaa cggaatacat    960

actataatat atcatgttgt ttatataaat tgaaaagacg aataactcga ataaaaattc   1020

aaaatagtca aatcgatcaa gtgtgtacca tatttggaac gtgtaaatag caaatctcta   1080

tgtcggtggg gcaccctctc tgttataata cagctccaga taagtacagt ctaaattgaa   1140

gtttcaactt gtgttaaaat atttaatctg atattatctg catgctacat aattattgta   1200

cgagcttgga ctttggggct catgcttttg tccttcgttt cgagaacgca aataagttcg   1260

gtgcactaag ctttcgctgt gcgcgggtcc ggataagggt ggaccacaag agtctattgt   1320

atatagtttt accctacatt tctgcaagag gctgtttcta tggcttgaac cggtgacctc   1380

ctggtcacat gacagcaact ttatcagtta ctccaagact cccttttaca aacttcactt   1440

attattacgc aaaaagaaaa gaaaattgtt gtggcttagt tggataggac actttatttg   1500

acgcaattct tgaaatggta aaatacactt aaaaatcaag catttttat attctctgaa    1560

tcaggtcaac tattcagaag tgtttccaag ttgtcataca aatacttttt ccccccaagt   1620

tgcagaggtc ataacttaac ttacttgacg tcaaaaattt catttaaggt gttcaaactt   1680

aaaataagta aaaaaaatct ccgataaagg gtgtttaata tatcttatat atcattaaaa   1740

tttaatattt tacctatata tataatataa ttttcagaca aagggtggtc agttgaccaa   1800

acttagggct atgtaccttc gcccatcatg actatatata tatatatata tatatatata   1860

tatattgtta gtagcccttc aaagttgcat aattattaga gagaatacac atttaaatat   1920

tgaccaaact tgtctataaa tttggatatt tttgctactt taattttctg aagcaaataa   1980
```

```
gaaagaagat catttgagaa a                                              2001


<210> SEQ ID NO 4
<211> LENGTH: 2001
<212> TYPE: DNA
<213> ORGANISM: Nicotiana sp.

<400> SEQUENCE: 4

tgtcgcagga gcttatccac caccttttgt atgatatttt cttttagttg gttatttgat      60

ttgtcctttt ctctatccaa tcgaacaatt ataagaaatg caccaatatt acttttatct     120

atcccaattt atgtgatatt tttattttct gagattcaaa ttttttaatt ttgattatat     180

acttagacat aaaatctttt aacttttccg aaataaaaat tacatatttg aaaattacgt     240

aaaaagtact ataactcaca aaaaatatta attttaaact atttaaaaat atatataaaa     300

agattacagt caaataataa ctcgtttgac tctcaagata cggataccgt cacataaatg     360

ggacgaaggt ggtatattga gtgtcctttc ataaacatag tactagtatt ttttgggaag     420

ctccatgaaa atgatatttt ttaattttta ttagtttatt ttaatttttt attttatcca     480

taatgatatt tttataatga cataaatatt ttcgaactta gtaactgttg ctcaaagttt     540

gcatatttat taaaattcaa taagcaagtg caaaacgttt attgcaaact caaaaaaatta    600

aatgagttat ttcataaaat ttaaatcttg aatttgcata cagtaactta tttaaaatta     660

tatattttaa attaattttt aatatgtacc cgtgggagtt gggtcggagg aagtataatg     720

gagacagaac cagctaagat aatcaataat tatactaaaa ggaatttagt actttctttt     780

tggtgttctc tctgtttcag tttatgtgaa cctattcttt tttagtccgt taaaaaaaat     840

gatctttttc taaatttagt aataatttag cctaaactta taattctacc cttaatgaga     900

aacttttata accatacaaa tattctgagt cttcttttta acttgtttag tataccaaat     960

ttcaaaaatc tttatttttt ttttaaattt tatgctcaat caaatatgtt cacgtaaatt    1020

agaacggatg aattatcacg taactaatct aagtaatcac agttgtctta catcaagctg    1080

gtcataggta aggggaaaca ctaattccaa gaagtcgtaa cgtgacctaa attaaaactg    1140

ccaccctttg gacaaaaaca aagggaaccc attttgcccc attgtgacaa ccaaatgaca    1200

caacatggca tatattgtga catacaccac ccaatcacca aatccaacta ataaatgtct    1260

tactttttgc atctaaggtt gtaacctaac taaatataat gaataaaatt tgtgaaagat    1320

taggattcaa atatataaat agctaaaatt atagatttct tttttttcta tttaaatagc    1380

ttatttggtc acatttctaa aattagctta tttttttttaa aaaaaattat ttttctcaaa   1440

agttatttaa aaaaaatact tttgagaagc agtttgtatt tgagtaatca atttgaaaag    1500

catttttgag tagcaattaa tctttggtca aacttttaaa aattatttgt aaatatatat    1560

atatatatat atatatatat atatatatat attgaacaaa aagtataaat attttgtgtc    1620

gacacttgcg acaaatagat gggtcacatt caatccaaca tctcattagc ttctactacg    1680

tgtttggatt actcccccaa cttgatggct gattgatcat cgaatttttg ccacactatc    1740

acttcttatg gtccaaatac ttctcatact tttctataca taaaattctt caaacccctc    1800

gaaaggtcaa ttatcaactt tcacgtgatc ttggaaactt gcaactttct tgccatgcat    1860

tgtcacttgc ttgaccaact tgcatcacct ttaatattag taataaaatt tttttacttt    1920

ccaatctcaa gatctataaa tagaaagttt tctttcctta gttcttgttt cactatcaaa    1980

tgaagaggca aagaggaaag a                                              2001
```

<210> SEQ ID NO 5
<211> LENGTH: 2001
<212> TYPE: DNA
<213> ORGANISM: Nicotiana sp.

<400> SEQUENCE: 5
ttttataccc atactcgtga tcatattagc gatcccccta atcgtagtga cggccactcc 60
tgcaatttcg gacctttgta cggtacaata gcgaataggg ctcctaaaaa acgtaaacct 120
gtaaatgata aagataacag ctaaaaaaat gcaaccatcc tttgaaacaa tatttttttt 180
aaaaaaaaaa aaaagttctt gcatgcaaat ttaacttcgt atactaatct ccaatgcgat 240
ttagaactta aaaattacta ttcctaaaca attagaaaaa ctgcatttct taatctaagg 300
atgttttgtg tctgtcctat tgaaacaact ttagactaca gatcgttaaa ttgtaatcaa 360
ccttctttta gtgtaaactg acgcggcttt accctttggt cagttaaata atccttacat 420
ttggtaaatg cttatattta ctcacgcgat taagagtaat gacctcgcaa aggtagagtt 480
caactgcacc tcactttgta ttctttgaaa tagccctcaa acattacgtc aatgaaataa 540
cgatatgatc tcgattttga atttctgagt cccaggttag tatatatata attacattcc 600
tattatcatg gcagatattt caaaaaaaag aaaaaagatt aaaaaaagaa agaaaaactg 660
acctagaaat atctccagtc cgcttcctag aaatataatg catgaacact agaagatagg 720
acatttaaga gagtcacatg gttgtttatg gcgagaaata ttgctaaaaa taaaaaaaat 780
atgatattat atgtcacata aagttggata atgtaaatgt tggaggataa aacacttcaa 840
gcccaatcat aggccgactg gtgaatggct gcttaaattt caaattgatt tacaccctac 900
caaatacaaa aatataaact ctttggtatt gttactattt ggcaatcaat catattcata 960
attggcatgt gagttgaagc taattgatga agcgaaattt gatgcgtgag tagtctcttt 1020
attgcaccac actaactgtt gagatatttt gctcaactta tttgaagaaa aacaaaaata 1080
aaaatgaact ctttggacac tttcaatctt tcattgccat ttatcaagat aatctgatgt 1140
aactaaaaaa ataataggac cagtacccaa aatccagatc ttttcccagc aacaggaaac 1200
ctttatcaaa ttttagtccc catttagact acctaatcaa agaagatact ctgcattcga 1260
cttaattcac gcacattgtc aataagacaa agaccttagc gaagccaacc aaactctttc 1320
ttttactttt tcatattgct ccatcagttt taatttatat cacacagttt aattcggtat 1380
gggatttaaa aaaaaacttt taaatcttgt ggtctttaaa gtataaaaga taaaagtttt 1440
gtggagccat aatatttgtg tgactataaa aatttctaaa ataaaatatt tataattata 1500
ttattttcaa atatagaata tataattttt ttggaacgga ctaataaaag aattgtatta 1560
tatactatat caattgaaac ggagggagta gatggttatc cgcacgcatc tttagtagtg 1620
acagttattc gatcttataa taggttggcc tatgcatgct gatgtattgt cttttagtag 1680
ctacatattg agttgaatta ccttttacca tgcctgcgac cccatgcaaa caagagctta 1740
ggtcctacga ggaatgtcct tctcagcacg ccagatgcac atacatgaac caaggcaaaa 1800
aagcaaagga aatttaacct ttttgccatt aattacattt aaactggact agctcattcc 1860
cccagctctc ttacccacaa gctccttcta taaattcaga aaccaactgc accccccaca 1920
ttcatcataa ctcgatctaa ctttagttat tgagagacaa accaattaca gaagcttaat 1980
ccttagagaa attaagagag a 2001

<210> SEQ ID NO 6
<211> LENGTH: 2001

<212> TYPE: DNA
<213> ORGANISM: Nicotiana sp.

<400> SEQUENCE: 6

```
gaattttggt atttttcgaa aatttgaaaa actccaaaag gttatttttc aaaatttttcc     60
cttcaaatca ctcacaaaat ttcaaaaaca gctccaattt atattcatat ccaaacacaa    120
ctataatttt caaatactat tttgaaaaat aattttactt ttttccgaaa ttttacaatt    180
tttatgtcca aacacccacg tagttctttc aataaaattt ctaacatgtt atggcaagac    240
atgtaggacg agagttgatg ttttttttttc ttttgggctt ttcaaatcga gttctgcaat    300
gaattggatt taacaataat agccatctat gactagttat taaaagaatt tgataccaga    360
ccattttaac cagatttgtc atttgtagga atttgggctt ttgtatttat acccgatttt    420
ggggtcacaa ttgaagctat aactacttcg caaaaaaact tgcaaaccta cccactttac    480
aattaacttc aggcttatcg ggtctgaagt taaaaaaaaa tagtctgaag tgcaacgcac    540
ttaaggccaa ttaagtctaa agtgtaaaaa ctaaggccaa atatgtctga agtacaacca    600
atggttttat acatttaaga ccaaatagat gtgaagtgta accaatagtt tcacacactt    660
aaggtcaaaa agtctaaagt gaaaaatttg cacttcagac ttaaggacaa ataggtcaga    720
agtgcaacca atagtttcat atacttaagg ccaataagtc tgaagtgaaa aaattgcact    780
ttagatgcac ttaaggccaa ataggtctga agtgcaacca acattttcat gtacttaaga    840
ccaaagaggc ctgaagtctt tggacttaag tgcaaattgc ccaaaaaataa aaatttgttc    900
ttcgaatttt tacaattcaa tacacgattt aacacctaaa tctactccaa atgagaaaaa    960
taaagcttcg aaacagctta ccactgtaaa acatcataaa ctaccttaaa atatgttcac   1020
aaaacaccat ataaaatcac tatataagaa gaagaagaag aatgaggagg aggaggcctg   1080
aagttgttta aactttggat actacttaaa aaaaattaaa aagtgggtat aggttaaatg   1140
aggaggacca aatagggcac tccgtaaaat ttttacatag taattaccgg tcaagaaagt   1200
taagtaagag ggatgccaca ctctattgag attaccccaa taaatcaccg aactccactg   1260
cttcatcaaa ctacagaaca tggggtcttt ctctctctct ccctccctcc ctccctccct   1320
ctccaactct atctccctca atacgcacaa gcagtacttt ttcattttac tttatatttg   1380
tgaaggggaa ccttgaaaca attataaact tatttctatg tgacatgtca cggattcgag   1440
ctgtggaatc agccactaag actagcatta gggtagactt tctacatcac actccttagg   1500
gtgcggccat tatcgcacct gcatgagccc ggaatatctt gggcgccgag cttccctttt   1560
ttatatttgt ctgtattttt gaataaaaag aaacaaaggt aggaagtgtt taggaatttt   1620
atttcttatg gataatgtat aaaatcctcc ccggcctatt accatattac caactacaca   1680
cttttttttt ccgggaattc tattacccca tgaactattt taaagtataa taaacaccac   1740
cctaagtgat gatgtggcat agagagtatg cacactctct taagggcaag tggaagttac   1800
aaaaataatt ttaaaattga ttaacatgta caagtgtcat cttttgattg gacattacac   1860
aattaattat atctaattta ttagtctcct tcgtcttcta aatctcttct tgcacgaaca   1920
agggagacat cgtttcagcg gcgaaatgcc tgagcgaaaa tccaatacaa cgcaaatcaa   1980
ccgagaaatc aaaagcagat a                                             2001
```

<210> SEQ ID NO 7
<211> LENGTH: 2001
<212> TYPE: DNA
<213> ORGANISM: Nicotiana sp.

<400> SEQUENCE: 7

```
gttttagaga gtactttggc aagaaaaaca agtgtgagag atcacccaaa acatcatatt     60
ttcttcttct ctttattttt ctggcaattt tgatcatgaa tattttcata gtttatttac    120
ccattgtcat gagtagctaa atcctttgtc tagggttttg atggaaccta ttgaagaatg    180
aacttcttga ttatgttaat atagtttgcc agtttaatct ctatttgttc aactacgtgt    240
ttgttgtagt tatttgacag gatcctcaat tagctgtgcc tatttggtat gcataactcg    300
ggagagagtg catatttagg taattgttga acaacatcac tcccaaagta taagagggat    360
ctataactgc gggtttaaag gcggaattag ggataacgaa gtcttgggtg caatctaaag    420
tgaactgtaa taaacaaagc caggtagcgt atctcgggag agtgcgtcta gtaaattatc    480
gtgattactc gggagagatt cacggtaaaa atagtgttca tggttgatag agatgtgttg    540
gtaaatctat atgaaacata aacagaaggg attccatcaa tatgggaaat cactacctta    600
gaaccttctc attattgttc acaacttaag catatttagt ttacaactat ttattgactt    660
tcaatcttag ttattaaata taccatcgac tgttattcac aacatttggg gaagttgatt    720
ctaaagaatt tagtaagtcc aacgaaagta attgataggt taattctctg tggattcgac    780
tctcgacata aatattcaga ttatatttgc aacgtgtgca ttgtcctttt ataaggtata    840
gttgggcatg atcactaata cttacattat tttttctaat acttgccaaa tgaccccaac    900
aaattttcag tctaaatggc cggctagtcg taatagttta acgtatttta aacgtgcgaa    960
aggggcttct tgactttatc attttatggt ttcagccggt agatggggac aacctacaaa   1020
ttatgtggcc aaggggacaa cccaaatgtg aaaaactaat tattatttcg ttcatttcaa   1080
tttatgtgtc ttattttatt caattttttt tatcttttta aatagtagta aatttttaat   1140
accaatgttt gtattttact cttaatgaca cccgttataa ggaatcatat ggcaatatat   1200
atatatatat atatattgac ttgaagagta ctttttatag cttatacaca cctttaattt   1260
aaggtaaaca atattaaaat tcattttaca ttttagtcca tttaagctat acccaccttt   1320
catttaaggt aatattaaaa ttctttttac attttagtcc agttaatcta gaacatatca   1380
gatgaaactg atcagagagt aacgatttaa attttctctg aagcagcttc agtcatatga   1440
ggcgcaatat caaatttctc ctttttggct aacgaaataa aaataaatgc gttagaagtc   1500
tctggtccga atagtagttg ttcgtttaaa acgtttataa atttaaagtt ctactgtagc   1560
cgaacacgtt tgtgtataac tatatatata gacaaaatta atagtcagcc accaaatcag   1620
taggttaatc ttctaaaatg aggctattta actaaagcta tagtctatgt acaatttcag   1680
gcaaccctat gctacttcaa caaccttggt ccccttgaag atctcaatat cccaccttat   1740
caccttatct tgttgatgct acaacgtatt gtatttgatt cttttacttt tatcctgagt   1800
agtggattta tcggaaacag tctctctacc atcacaaggt aggagtaagg tgtgtgtaca   1860
ctctaccact cccaaacccc actttgtggg attacattgt ctttgttatt gttgttgttg   1920
tcgtcgtcgt cggcggcttg aagttctcat tatattagca gccttaagtt cttgttcatt   1980
cttgtttctt atactgccag a                                             2001
```

<210> SEQ ID NO 8
<211> LENGTH: 2001
<212> TYPE: DNA
<213> ORGANISM: Nicotiana sp.

<400> SEQUENCE: 8

```
tttaataagc agcggtttat ttccgggcga aaagggtaag tcggccccta gcagtgagaa     60
```

```
accaaaaaga aattgttcct tatattgtgc gcatgtcaac ttttttggct tggcttgtag    120
acgtatacac gtggaattaa tgagagaaga taataggagt attatagtag ctaggtacat    180
agtatttagc aaatctttca tggctttgac ttcccacgaa attaaagcag taatcttcat    240
aagctgcata ttatctccat tcttatcacc ttttgtacct acccacataa agcccgactg    300
tttggttggt caaaggtcga aatatctatg caacttggcc aatatgcttt ctatataata    360
aaatatgcat ggcctaccat ttaatttgta tagcaacaaa atgtggcaaa taaaaaccct    420
accagtataa tttctgagct ttcaacctaa attaaagaag tctatatcat gctcagccta    480
tatattttga ccatcgagag caaaagcatg acgatgattc cttgtattta agagtaccgt    540
ggcttaattg ttaatgaagt gagtgataat tatcggagat tagagtttaa attattagca    600
gtagttatat tttatctgtc tatgttatgg tggcaaagtt accaaattca tttgctggtt    660
gaaggtaatt accgatgttt aatttgatga aataatcgag gtgcacgcta acagtaggtc    720
attagcctcc tataatgctg aaaaggatgc cctaaacgta ttctaaattt ctatgtcata    780
accatacgtc aagggttata ctattatact actacagtcc aacactcgag aaaaattagg    840
acattgagtt tttatttttt atttttaatt ggcgaatact gttaagttgg ttgcaaatta    900
tatactatct ttttcttgtt aaaaaaatac acaaatatag agacaaattg actaaatgca    960
atcaaaccaa acgctatatc aaacagaatc tgctgtattt aagacttatt caaagttgag   1020
atctcaacat ctcagcctta aaaagttgag atgggtaata ttggttttta aataattata   1080
tgacaaaaaa gaggtaggtt gtttattata taaagatgga tggtgattct ccagatatct   1140
tttggcaaac ataaattaaa ccaaaattca acgccttaaa ggattaacta aggctccaaa   1200
tgtgaattgc gtaacgctgc atgtccccaa aaagtgaggt cggcattagc tgaaatatct   1260
tttcaggatt atcccaaaag aaaataccta gtcacccccg gtacttatac caaatcgagc   1320
aatttaaatc taaaaattat aattaaaatt gaaaatacat atcacttaat cttaatcaag   1380
tgataaaaat ttacacgtca tatatttctt gaatttgtgg taacactatt aaaaaaaaac   1440
tccgcctaaa tgatctaaag tcaaatttga ccccaaaaaa aatctaaact aaagtcaatg   1500
ctccaactca aaccggcgtc ggatacgggg cgtcactggt cagtcctatc aggactcgtg   1560
agacttgtaa ttcttatcca ctaattctca taaattcaat catattacgt tatattttta   1620
gaaaacccat ataaagatga agtagaatta gaatttaata tgttttctat atatagatcc   1680
gaaattagaa aagaagaaag ggcagagatc tgggttcttt tatcattgat cttctgtttt   1740
ccaattgtct taattcagta gctgtcatgc atgcactaga taaaagttat cactaatttt   1800
cagtgggttc cacaagtgca tgtaagtctt aggattttac tactgctact tgtttggtga   1860
cttttatata tattgtttca tagatatcaa gcattgggtg attataacaa caaagatttc   1920
agattcgact aattcaaatt cgtgtcggat aagattatat aaggaattga gaacataaaa   1980
taaggatctt tcattgaaaa a                                              2001
```

<210> SEQ ID NO 9
<211> LENGTH: 2001
<212> TYPE: DNA
<213> ORGANISM: Nicotiana sp.

<400> SEQUENCE: 9

```
tggtatgaaa tttgaattgc attgagtatt cttcgtgttg ctgttgtgtg tttactttga     60
gactatgaga cggtatcccg agagatcccc ctgcatgttt actttgggac tacggatttg    120
```

```
tattccggga gatccccgtg cacttttata ttggaactac gggattgcac ccggtagatt    180

cccccaatat tgggtattta tatttgggac tacggatcgg tattctggga gatccccgcg    240

cactatgagt tggactacga gacagcaccc gggagatcca ctggatattt atatttggga    300

ctacatgatg gtatcctggg agatccctgg ttgttatctc tgtgttaagt tgtattcctt    360

ctgtgattat ttggctctgt tatagttgtt gttattttta ctatcctgtg ttacttctta    420

ttgtttgcac ttaattatat tgtcttattc tatattgtta taccttgttt ttcatctaaa    480

ctcagtaggg ccatgacttt cctcgtcact acccgaccga ggttaggctt ggcacttact    540

gagtactgct gtggtgtact catgcccttt ctgcgcatgt tttttcatgt acagatccag    600

gtacttcgac tcagccttac tatccttaag gcgaggcgat tctccagaga cttcaaagta    660

tatcttccga gtccgcaaac cgagaagtcc ctttctattc tcccatatag tattagccct    720

tctgtattta cttttgttta aacattctgg agttagacac ttgtagttat ccaacagctt    780

gtgatttcat tagattccgg gttttgggaa atattgtttc agttcgagag tttgtattgt    840

atatgtcgag cggcatctaa acgcttcatt atgttatttc tgtagttttt gactagtttt    900

attctgttat tttctgtttc cgtaatttgt taagcttacc tagtcgtaga gattaggtgc    960

tgtcacgata gttcacgaag gacgaactgg ggtcgtgaca agtttactta gattatagga   1020

gtttatggga tatctacagt attttttttt tatatacatt ttattgatta atatgataga   1080

cagttcaaga ataaaagtta caccgctagt acgtaagaaa tttattctta acaaatttaa   1140

tgaacccaag ttgtggttga aaaaaaaagt tgagtttgaa aaaaaaacat ttgtatcaag   1200

ttggggttga aaaaaacaaa ttgaaccaag ttgaagatga aaagagagga gagttcaaaa   1260

aaaaaaaaaa agaaaaaaaa aaaaaagagg agaattcaag ttgaagatga actctttaac   1320

cactgtcttc ctctttctct ctcctggtat aaaccgacat tctttaagga gttcgaaagg   1380

tcgaaagcag atgcatgtaa cttcatcatt ttcagtcaaa gtgcaattaa cggtgggaac   1440

atatctctct gagtcggccg ctgtattgtt gttttttttgg caggcatcaa atctttcttt   1500

tttatttact atttaaagaa atttaataaa aatacaaagc tgagtatatt taactattct   1560

ttgtacaata tagagattga caccaaactt cgtgcatgat ctattagcag aaagtagcac   1620

gaagattcaa ctattctctt cacggctgtt caagtttgaa ttttcctcct tatattatat   1680

agccgtttgt aagggaattt ttatcagtta tctgtaaaaa gaatcagttg tctactttgt   1740

gcatgtgctc caaatcaagt aaaataccat aagggagccc atcaattcag aaatatacga   1800

tttgggttgg tcttattttt gtgctacgaa aagtgttcga cgaaattgat tttgtcagag   1860

ttcaaagtcg gtggcttcag attctgcaga aacggtgttg tgttgaagaa aagctgaaaa   1920

gggtatttat aattcaccaa aaaagcatct gggttggtgt tattttgtcg taattttgtc   1980

tagtttgaag tgggtcgtac a                                             2001
```

<210> SEQ ID NO 10
<211> LENGTH: 2001
<212> TYPE: DNA
<213> ORGANISM: Nicotiana sp.

<400> SEQUENCE: 10

```
acaacaacaa cattattatt aaaaacaact gcggaggcat gattgttgtt gttgttatta     60

ttgttttacg taatattgtt aaaaaacaac ttcagatgca tgattaatta agctaggatc    120

gcagtaaaat ttcataagtg ggatctggag aggatagatc agcgtacgca aatcttatcc    180

ctacattata gaggtagatg ggttatttcc gatagacact cggctcaaag aaagcgattc    240
```

```
caaaacatat tcgaagaaag gaaaaaaata tgtcgaaagt accgacaaaa ataatacgat    300
aatactaata aaagaataga aaaaaaaaac aatacggaac aatattacat tttaaaactc    360
agtccatatc aaacaacatc acaaaaatag ataaggacaa tgtgacaaac taatcacccc    420
tgccctacat tttaatattt gcagtgtaca attaacggca tgcgtcacgc ccttagactt    480
ttgtgtgaat ttacaagtat tttattcctc aattatatcc atcaatttat atggttaaca    540
tttatttatt tattttgggt gcaaattcac atggtttact taatggcaca gtttcttgaa    600
ttataaacaa attcatgtta cccctgttcc aatatcgtct gcactaaaac agacaaaaaa    660
aaatgtttac tcgcatatat taggcgcggc ccttccttga atctttacac agatactttg    720
tgtatcagac tgtcttttac ttgcacacgt tattttcgtc aaatcaatga gtgtaatgca    780
tgcgtattca atataaactt tgtactccct tccgtcctat ttagttatac tttggctaaa    840
aatagttgtt ttaaaataat catggtttaa aaaaaaaaca agaaagagtt acttatattt    900
tttgcaattt taccctttct actctaataa atgttcctca aagaagtaaa agagattaag    960
gggagaaatt aaaaaatagc cagatttata agtggtcatt ctaaaatagt cacagtttca   1020
aaagtaattg aaatttagtc acttttcatg taaagataaa tttgaacgaa aacattgttc   1080
aaaatccgaa aaaatacttc aatataatat actggaattc cagtataata taccggtcca   1140
gtatattata ctggaacttt ccgtgtgttg gagttctaac ataatatgtt ggaagttcat   1200
acacaggtgc accgatctcc agtacattat gctggaactt ttcgtgttgc agcaaaataa   1260
tgattatttt tcaatgactt tgcaaacgct ggctattttt gaatgactag tccgaaaact   1320
ggctagccgg tgctattttt atgagattga gagatctaag aataaataag ggcaattcaa   1380
tcaaataact catattagta atgttttctt aaagtatgcg tgcaaaaggc taagtaggag   1440
agagtattga ttaatcgtga ttaagtgtat atgctatcac ttaaatttga gactcttaaa   1500
cttgaactta ttaatttaat gtaaacatca ggtgcgagta agtattttca tgttaacaga   1560
cacagtctcc caaacacaaa aaaatggaat gacctgtgac aagctgctag caaaacatag   1620
gccctgctaa caccaaaaga ctgttaaagt taaacttatt aatttaatat aaatatcagg   1680
tacgaataag tattttccta actacagccg tcgactagtc ttcaaattgc tagcaaaaca   1740
taggccctaa taacaccaaa gttcctatat taagtgctat atattgtcac tttattttga   1800
gacggttaaa attaaactta ttaatttaat ataaacatca ggtacgagta agtattttca   1860
taactacagt cgtcgactag tcttcaaatt gctagcaaaa cataggccct aaaaacacca   1920
aaattcctat ctctctgtgt atatatatgt aaagcacata tctaattttg aaataaaaca   1980
ttcatagatt agctttttca a                                               2001
```

```
<210> SEQ ID NO 11
<211> LENGTH: 2001
<212> TYPE: DNA
<213> ORGANISM: Nicotiana sp.

<400> SEQUENCE: 11
```

```
taaaaactga gtatgtcaac atgaggatca actggcagat atacttacaa aaggattgtg     60
aagagctcaa catgtacatt tgctgaacaa gctagggttg aagaatctgt atcaaccatc    120
agcttgagag ggagtgttaa tcaacatggt taccactagt ttatttataa agtgtaaatg    180
ctaaaccata gctagtgagt tagttaatag ttagttgagt ttgttataaa tattagtcag    240
ctgtacagtt taacatagct tctctttcag aaatgaaaat tgctcttctc tcatttcctc    300
```

```
tcttctagat tcttcttctc cctccttctc ttagctcaga tctctcttat gacagctaac    360

aataaatacg aatatttctt gtaacggttg ctcattgaat gttgtctttc tcaaccgata    420

tctttctttc aagttttccc cccgattcga gtatttttga aactcactca gcaccggtca    480

catattcgta atcggtgcca gctatttgct tactcatatc ttatttgact tcattgtcac    540

gtgtcagaca gaagtatgtg cgcatatacc atcaagtctc aatttgaaat aaaatcaact    600

taagcagtta aaagtcaaat ctcttttagt tcggtcttta aaataataat ttaaataatg    660

aacctataaa acacgcaact cacactgaat ataggggcag acataaaagc cgaaagactg    720

aattccgaac cggaccgaat tatttcggta tttcgatatc ggtttattca gtatttcggt    780

actatttcgg tataggattt ttagttattc ggtatttcgg tacgatcctc ggtattgaaa    840

tttcgatatt tcggtatacc gaaataccga ataatttaag tacaccttcc ttcactgccc    900

agcccgttat caattttcag cccaagtttc taacttgtta tttctttccc ttagccagta    960

gcctactaag attaagccca acgccccaac ctaacattag aaattattat aattagaaaa   1020

gtataaagaa agtactcaca ttctactgct atgctcatgt agtgatttct attagaaatt   1080

attagaagtg aaggtactgc ccacattttc ttgttgctat actcattatc acgcaattag   1140

aaattttcta atgaattaga attcagtagt tcagcacaga ggcggatgta gcgtattacc   1200

tacgggttca actgaaccta taactttcga cacagagtaa aaatttatat gtaaaaattc   1260

tttaaaattg taaaaatcgt agatatgaac ccataacttt aaaaatataa tgggtaacat   1320

taaaattgaa cccatagaat ttaaatcctg gattcgcctc tggttcagca ttgtttagtt   1380

cacaaaaata tggtacgatg ccgaaccgta tcgaaaccat accgaaccaa acaagaagat   1440

atcgaacaat accgaactac tttggtacag tatttggtat gcacacttga tatatcgaat   1500

accgaaatac cgaaccgtaa ttttcgaata ccgtaccgaa ataccgaaca ctcacccata   1560

actaaacatt aaaaagctag aactcaggtg tttaatgact aaacggaagt aagatctaga   1620

taatccgtca ctctgttgat ttgtaaggct atcgacatgc aaaagtggaa gcaaaatgga   1680

gccgaaattt taacaaaaat gctgaaccaa taccatgaaa ttgatgaatg gtgggaccct   1740

atttcactct tttagaattt gcgtaagacc agaaaataac ttcaatcgaa atcaaaataa   1800

ataccaaccc ttttaggccc caaatcacta cgtgtgattt gcaaacgtca ttagccttat   1860

gtaaacagtg acctcatgcc aacatattat cgcagcctat aaatcttagt ttacatttca   1920

ttttctttca aacacacaca cctcacaata gaactaagtt gtaagagttt cattttcttt   1980

gttctttctc acaaaccaaa a                                             2001
```

<210> SEQ ID NO 12
<211> LENGTH: 2001
<212> TYPE: DNA
<213> ORGANISM: Nicotiana sp.

<400> SEQUENCE: 12

```
ttaactacca gaaatcacat aaatacataa aatcaaaagt ctatcacgga atatcaataa     60

aaagagaaac ataaaatgac aataagtaac aatttcaatt tgaaacttat caaataaatc    120

ttacttgtta cttttcaaat gagtgaaaaa atcgaatcat gccagattaa tatatgttaa    180

gacaaaactt aaagtaggaa gattttgaat ttttatagtt taactttaaa tattttgcac    240

caatgcaagc ttaacgcaag atactgctca tactattttc ttttctgttt ttgtaatgaa    300

gaatgatttt tcttgcataa agattcttat ctttttcgtg catttgacgg gatttttttat    360

ttcttttttc tttttctgtc aacaagaaat ttatttttgt tgtttcgtaa catttttttcg    420
```

```
atggcttgaa accgaaaaac taaatcgatt aaaccgaacc gaacatgaat aaatcgaatt    480
gaaccgaaat tattatggtt cgattttgat tattaaaatc acaaaccaaa aatcgaataa    540
accgaaccta acttctacaa aatcgaacag aaccgaccga cgcttacctg ctcatttgtc    600
aggtgagaca aatattaagt agccatcaga agatcattat atatatatat atggaatctc    660
tattgtgact ccacctgtct catttttaa gtaggatttt tattcaactt ggtagaaaaa     720
gttaaatcgt tactaattga cctatgtgtt catataaaaa attctaatat gtggtcgaaa    780
tttcaaagac cggcgcaagc gtcaagataa attaccaatg gcaataagtt gagtcttgaa    840
atttgcaaac aatcacaact tgtattagct tcgactgaga aaaaaaatgg aagaccaagt    900
gaaactgcta ggagcttttc caagtccctt tagttatagg gtaatttggg ctctgaaaca    960
caagggtatc aactatgaat acatagagga agatctttca aataagagcc atgatctttt   1020
gacatacaac cctatctata agatgattcc tgttcttgta catgctggaa aaccaatagc   1080
agagtccaca gtcatccttg aatacatcga agagacatgg cctcagaatc ctttgctacc   1140
aaaggatcct catgaaaggg ctcaggctag attctggatc aagttcggag aagataaggt   1200
aagttaatca tgttagtatg tttactttag gtccagtgtt tgccaagagt ttttaaatct   1260
aaatatcaga aggaaattaa tgtagagtac ttctagctag cattaaaata tttttactga   1320
ggattcatat aattggcccc aacttggtag tacatgctag ttattgtcaa gtgttaaatc   1380
gagtaaatta cctcatctaa aattttaagc gctaaatgaa ggatactata ctttatttat   1440
aataggtctg cgacacacca tcacttgcag gcttaattca tttttcttga gccaaaaaca   1500
tgaaaatttt gttcatatgt cacaacaata taatgagact tgaagaactc agctcttata   1560
ttattagaca tggatcaaat ttacttagtt attataggcc tgtaacaaca agtaacatgt   1620
tatatctttt taatatagag cccagaattt ttcgcaatat ttcacaagat aggggaagag   1680
caagtcaagg caactgaaaa agcaaaggaa gtgttgaaaa ttatagaaga gcaaggtctt   1740
ggagagaaga agttttttag cggggacaca attggattaa gtgacatagt ctttggatgg   1800
atagcgttat ggctggaagt catacaagaa gctgctgaag taaaggtctt cgactcagtt   1860
agtacttttc ctcgtttaca tgcttggata cataacttta agcaactccc tgtaatcaaa   1920
caaaataccc cacatcggga tgcaatgcta gcttatttca aacgtcgtcg agaaatggtt   1980
gtagcagcgg cacaaggttg a                                             2001
```

<210> SEQ ID NO 13
<211> LENGTH: 2001
<212> TYPE: DNA
<213> ORGANISM: Nicotiana sp.

<400> SEQUENCE: 13

```
atcagtccta gcctcgaacg acttcgaaga acgttgtcag acaatcgagc atagccaaca     60
aaaagccgaa atatccgtga ccaaccgaat attacggctg gaatctcggc atgtatcgat    120
aaggaaccaa caatcagcga atcagaagat tttttacctt tttatagagt tgtaccaaaa    180
ataggactct tctactatat aaagggggtc taatcattca tttgacatat tgtaacacgc    240
actcataagc aatacattat tatttttatc cgtcttttaa gttcttgttc tttttcatcc    300
ataccggtct ttgtgagttc ggttcgagag tgactatttc acttaggctg aaactatcca    360
actcttgtgg tttaaattta tttggtcttt gtttattcaa tagaaactta atttattgct    420
ttgtatcaag ttaatccgcg tatccttaaa accacttata aatttaattg ttatccgatt    480
```

```
ttgagggtaa acacctatat ctatcattct attgtaatag ttgatagggt ttattatcaa    540

taaaacctcc tagtttaatt tagctgttcc ttcttctctt ccaaatattt cactgttcca    600

ttgcagctgc atcagataac taaggagaac aatttggatg gtaggcccag agaaagatat    660

gatctaagac tagagagaaa ttcaccaaga aaatcgtact ccttattaaa attttgttta    720

aacggtcaaa gtagtacttc tcgtcatcct aaatcctagt actatttaat ggcggctttt    780

atgtttctgg aaaaaagtag ttgcaaggag aaattaattt atggatgctg cgtttaacta    840

tagattggtg ttaaacaata tcaaaactca aaaaggttag cttcaaacta aataatattt    900

agacattaat tattatcctg taatatttaa aatttttcatc agaatacttt ccaatttgct    960

aatattatta ttaattctaa tatatatgct ttttttttt gagaaataga gaaatattta   1020

ttttctacga aagatgactt tcgtcttctt ccgccaaaat ataggtgaaa aatcgaagac   1080

gtccatagca gataaaatag agggcactcc tacttgtagt aattgatcac acttaacatg   1140

aaagagctat aatgttagtt attcgttcgg acgaactcga taatttttgt ttaacttgta   1200

ttagaaaatt tattaaatat atataaatat tttaattaca gactcattaa cttaaaagaa   1260

gatatagact cattaactta aaagaagata tagattccaa cacaagttca aaattcataa   1320

acgtcaaatc ttggctaaat ttctgaacat gaatgcattc ctttaaaata tagataataa   1380

gttaggatgt tgtcactttc ttaaagcata ttccgactga gtctggtaga atctcataaa   1440

ctttaggcct tatctcttca attaggcaat tacttacctc cgctctactt taagaaaatt   1500

caatggagta caccattatt aagttcatat aaaaataaaa ttatattaat tctgtctctt   1560

gttggttcgc tctatctttt tctgttttcc tgcttcaacc ataacatata caagaactac   1620

attttccaag ctagatatat ctaacatgac tgactttgta aatttctttt gccaagttaa   1680

agaaaaaaaa tgatgttatc caaataataa agagaaagag ccctaatgaa aaaaatgatt   1740

tactattaga gttgttcagc taatcacatc aattatggtt ttcatcaagt atgactaatg   1800

gcggctctta tctcacgtga tgtgacattg aaattctttg actttaacac taatgtcata   1860

tgctttcaaa ttaataatcc gataaagtct gctaacatgt gactttccaa tttttttctt   1920

ttacaaattg cagacttttc aactcttatt ccctattaaa acccatccat actattcctt   1980

gtttctcacc aaaacccaaa a                                              2001
```

<210> SEQ ID NO 14
<211> LENGTH: 2001
<212> TYPE: DNA
<213> ORGANISM: Nicotiana sp.

<400> SEQUENCE: 14

```
tttcaaatta ctaagttgct aaaataaata cggctaataa gtaccattat ttacatgagt     60

aaatactaaa agaaaaataa gattcatttt atctaaacta tggaaaaact aaaaaaataga    120

tatccaacac tgttttcatt catagtacaa ttgaattgaa tgtcttttaa tttattagta    180

ttagtatgga tttgattttg gtttagaatt tatttgagtt actaacattt atggactata    240

aaacttattg gagcatccaa aaattataag ttccaacttg aaataataca ttagaagata    300

aaactatgaa aaaacttaag aaatatttat aaactacact acaataaata tttttatgta    360

gtaaatatat ttaaaacttc tatacttata atgtcgggtt tgtttgattt cggtttgact    420

ttttttagtt agaaccaaat caaaccaaac catagtcggg tttttttctc ggtttggcgc    480

ggatttccgg gttgatgcga tttgtcgatt tcgtttgtac acccctaaat attacaatag    540

attttttaaa ttggcagcat atataagtta atttcttaag ttttgtatcc ctcagtataa    600
```

```
agaatttatt acactatcgg gacatctttc ctattatagc agaatttttt tcttgtttca    660
aaattaaaaa tctcacattt taagtaggct tgcccataat tatttgggtg acctaatagt    720
ataagaaatt cttcacattg acgagtattg aacttaaaac tcttttatta taaatttaac    780
cttgatgccg ttccatttac cgactcttca aaccacatga ccagaatcaa ttctggaatc    840
cttcatcact aatcaatatc tgttcgaggg catctcatag tcaaaatgtc gtagcaatat    900
cataaaggaa tgggaaaaaa aaatgaaaat aaatcgcctc tggtcgaagc tcataatgaa    960
aatttcggcc ccgcaaactt tatcaagttc tgctctcagg ggttattttg gtttgaggta   1020
taaaaagatt tgatctcggt ataaaatgtc gtatattact tatataatgt ttggtttcta   1080
ttataaaatt cttcccataa ctaatataga tgtctaataa caaatgctaa tttccgaaag   1140
gaatatcggt cggaattcct cggaaattgg ctcgtcggta acgtcgctac cagattttcc   1200
atcgaaaatc cctcctcgat gagccaattt ccaatgggac attcgtcgga aatttacgtt   1260
tttggtagaa cttataacta atactacaca aattttggtt tccacctatc taaagacaaa   1320
aatgccttaa ataaggcagt cttacacaat gcttcaagca ttattctaca acaattcatg   1380
cattattaat attcactctt gtattattat tcccgatcca tgcatgtatt gtaattacgg   1440
catagctaga cgcgcgggaa accaaattaa cgacctctaa acaacaataa caacccagta   1500
gaatctcacc ggtggagttt ggggagggta gagcgtacgc agaccttacc cctatctcgg   1560
aggtatagag agactgtttc cgtgattgac gacgaccttt aaattatttg tttatgaggt   1620
ttgattaact tggacaagat tgtttgtatt catattttag gcttcagttc acttaattaa   1680
actacctata tgagaacatc acatgaagta ctaatactaa gagaaaagac tcaatgtaag   1740
gcggctttta aacaattctc acgtttaact gtctcattca caaaattaga ctgacttgta   1800
ttatttcttt tataagttca actttttgcg tattcagaaa gattctttaa tttggccaac   1860
tggctactat agggactctt ttcttccagt tatataatcc ttgtctctca aattcaagat   1920
ttgtaaacca attcgttatc cctttcttca actttaactt ctatatactt gagattttat   1980
ctctatatat agctaaataa a                                             2001
```

<210> SEQ ID NO 15
<211> LENGTH: 2001
<212> TYPE: DNA
<213> ORGANISM: Nicotiana sp.

<400> SEQUENCE: 15

```
actatactat agtgtgatga tccaattggt catttttgag atctaaaatt tcttttctct     60
atttgagacc tctcatatgt tcattagtaa tatatgaatt gtgggtatgg tggcacgggt    120
tccgagggat ttgaagcctt atggaacact tgaactagaa cttaaagcct taaattacga    180
gaattgacca aagttaatat tttgagtaaa caaacttaga ttcatgattt gaaagtttca    240
ttaggttcgt atgacaattt tggacttaat tatatgttca aagtaggatc cgaggggtta    300
gggtataatt cgacactatc caaaaaagtt gtaaacttat gagttcataa attggatttg    360
aactttaatt ttgagttgtg atgtttctat atatgttttg aacccttgaa caagttcgta    420
tagaatattt aggcaagatt caaagtccaa attggactcg actaaattca gacttcttag    480
ctataactaa gtaaattgtg ttctttttgcg tggaaaaagt ataacacccc atgcaagaca    540
aaagtttgta attcctcggt cttaatttat gtagcagtaa tagattcagc atcgagtata    600
aaaagaaaat aaatttttga aatttatgat ctaaagtaag ccatatacgt ttgcgtaatt    660
```

```
acaaaccatc tcattaagat aaaataaaaa gtttaaagtt aaaatatttt taaataaaaa    720

aatatgtcat tctttttaga taagctaatt aaagaaaagt atatcagata aaatggaaca    780

aaggaatacc aagattaatt gatctacttt caaattcaag tattacctca gctcaacaag    840

aataattttt tttgggggt aagtaattaa tttggtattt gtttagactt tacccttacc    900

ttttgtgagc taaagaggct ggttccaata gaccgtcgat ttaaaaaagc cttttcaaaa    960

gaggtttgta aaatacagga attaaaaaaa gatgaaaata ctaaaaaaga aaaaggaaaa   1020

atattataat agtagtaaag aaaccaaagc aaaagaagca acaatagtaa taaaattaaa   1080

gagtaagatg atgatggtga tgacaatgat aatactaata ataataataa taatgatgat   1140

gatgatgatg atgatgatga tgatgatgat gatgatgatg atgatgatga tgatgatgat   1200

ggggagaaaa gggagaagat aaggtgatct aaactagact atgttcttcc acagaaaaga   1260

gagaaatcac tcgacgacct actaacattc tactctaatc ctcgactttc atgctcttct   1320

atctcgggtc gtgtcctagg taagttgaaa atgtggcatg tctaattacc tctctccaat   1380

tcttcttcgg tctacctcta ctctccttag acctatcatt gccaacctct cgcactaggg   1440

catccatgct cctcctcttt acatactaaa agtatcccag tcgcacttct cgcatcttgt   1500

cctccacaga ggtcactccc actctgtcgt gaatatcttt gttcctattc ttatctctcc   1560

taatatgtcc gccatatcac ctgaaattac ttaattttgt catctgtcac tcaccattta   1620

attttttaaa aggtccaaat ttaccccgat caacttttga gtatagttca gaattacaag   1680

ctagaaaaat aatagtatta aatcaaagtc tacggaggac gaagttgctc aatctcgcat   1740

gccgtatagt ataggggcaa cttcgcccct tctccgaata ttcgaccatt ttttctcata   1800

aaattctatg tctctccatc acaacatcag atttgaactt tctacatttt ttttttcttc   1860

acttgtgaca aaaaatacac tgttttaatt ccatgacgtg cttcactggg tgtgactttg   1920

gctttttaag tctttgtcgg tcatcttctg cttgtctata taagaagcag cctaatggtt   1980

ccttaaacac acaatttcag c                                              2001
```

<210> SEQ ID NO 16
<211> LENGTH: 2001
<212> TYPE: DNA
<213> ORGANISM: Nicotiana sp.

<400> SEQUENCE: 16

```
ttatgtgaca tttttttct ttttatgatg tttaaaaaaa ctagtatctc attaattaat     60

taattatatg tctgaaaata ttaatttttt tactttaaac tttctattct atctttagtg    120

ttatgatttt tatatataac catggaaatg ccatgactta tttagtatca cgcgttttaa    180

aaatttttct tttattttt aaaatttcat atattccagt caaatagatt cacataaaat    240

gagacggatg gggtaaatag taaatcttaa agctagcaaa ctatgttcaa catcatttga    300

tgggtttctt ttttcaggat aatattttat gtgtatttgg tctttttgga ttgttttatt    360

aaaagaaaaa ctccttgaga tgcatggtaa gccaattgat cgtcattgtt attttgaaat    420

aacaagtacc atatcatatg aggccgtgat tatctaaaga cagataagga aattgggcta    480

tcaaaataaa tatgtaagag ttatgttcct catcattaag tatgtgaaac aaaattgtca    540

acttgtacaa cgattctgga atctacttgg cgttttcaaa gctctctgag ccacaacaag    600

ttcttgcaat taagttttat aaataatttc catgtcctca tatttcacta tcttccagat    660

atcccataag actacgtacg acaaacggca ccataaatat taatcataac aggaagacta    720

aactcaattt ctaatttccc tattaccaga aaaattagaa caaataacaa gaagactgtg    780
```

```
atactccatg aagaaaacca ttaaaacatt ccgggttctt actagaatgt ggagtaatat    840
atgctttcct gttttggaaa gtgctaaacc cacaggctaa ggtaagaaaa gtagtcccac    900
atgctagaag cttcataggc cccgactatt ataagctact atacgttgct tgacaaaagt    960
ggaaatgcaa atcgaattct caaacttgca tctcactttc cagcctaggc cacaaaataa   1020
aagacgccat aaattaatta gttcgtggat caagaggtca caatttggac aacagtaaca   1080
aggttccatg tcaatctcct agttaatggt gttcctttgg atttccctat cccttttaat   1140
tagctactcc ctccgtctca aattatctgt cgtgatttct aaagttattg tctaaattta   1200
tttttcatat tagtagttca agactaaatt aattatttct tttccatttt acccttaata   1260
tgatattgtt cttgaagatg aagataatac ataaatagga agattatata tatcttaaaa   1320
cataaataag ggtaaaatag tccaaacctc ttctcattaa tattttctta attaagtggc   1380
gtgtaaaaaa gaaacacgac agataatttg aggggagaat atttgtaaag aaaaacaaca   1440
atttgcttct aaacagaccc aaaaggaatg ttagcccaat cctggtaaaa cataaatgtc   1500
agcaagacag tgctatgttt aattatcaga aattaacagt actacttgca atcggaacac   1560
gactattaaa caaacaaagg tattatctac cagtacattt ctctttcatt aaattcctgt   1620
ggtcagactt agttactgcc cctttgagaa ttcttgtcct actacttcat cctcaacttt   1680
ccgtccaata tattattctg gtcatttgtt tatttctgaa aagcttggaa ttacatatat   1740
acatcctagt ccatttaatt aagataaaat ttcctcattc tccctgacat caatatgtgc   1800
taaaagtcgc ccttgtcact caccctagtt cacactcgag ctttgggatt ggcattctct   1860
ccatttcatt ataaattcaa gccaccacac aacacagagt cacagagcta aatatagcat   1920
atatatatat atatatatat atatatatac ctccctgcat atcttcctca gagtcaaatt   1980
aagcttcaag caaaacaacc a                                             2001
```

<210> SEQ ID NO 17
<211> LENGTH: 2001
<212> TYPE: DNA
<213> ORGANISM: Nicotiana sp.

<400> SEQUENCE: 17

```
cataatgtat tttctcaaag aattatataa tatgtgtata ctattaaaat acattgtata     60
tgatagtaat ccacaagtat aatataatct atatatacca ttaagatata ctagtaatat    120
attcatatat accatcatca ttcatcatgt ttttaataat tatacaacat aatgaataat    180
taaatttaat atagtactac gtataagtgt aaaaatagag gtacaatcag ttacttgaag    240
gaggagtgga ataagaaata aattgaagac aaaagttgga ttgaatagac gcaaaaggaa    300
aggttttagg gtgaggaaaa tttataattg tacagtattc aaaaagagga gaaagtgagg    360
gttttagggt acacggaatt aaatagggga gagaaaatta ttgggaaact tcaaaagttg    420
tggattacca ttaattacta atcctatttt aatgggattg gtccaacatt ataggtttat    480
gctagaaata taacgtagtt aataagctgc catatttgtt actccctccg gtccacaata    540
tgtgatcaat ttaccttttg attttggtcc aaaataagtg tttaaaatag cacggtctag    600
ccagttttcg gactggtcat tcaaaaatag ccagcgttta ccaagtcaat gaaaaataac    660
cactattttg ctgcaacaga gaccggtcca acataatata ttggagtttg gtgcacctgt    720
gtatgaactt ccagataata tactggagca ccggtgctcc aaactccagt atattatgct    780
agaccgatat attatactag aactccagta tattatgctg gagtattttt ccggattttg    840
```

```
aacaatattt tcgttaagat atatctttac atgaaaagtg gctaaatttc gattaccttt    900

gaaactgtgg ctatttttga atgaccactt gtaaatctgg caatttttga atttctcccc    960

catttatata atcaagaaaa aatttgattt tttttaaaa ttatccttat atacgtatcc    1020

ctaaaaagtt ttttactcct cacattaaat tatgctgcaa catttaatta agggtaattt    1080

agtcacacta actattttg tctagaattt atatttcctt aatgggtgtg cccaaggtaa    1140

attgaccact tatactggac cggagagagt aattgcttgc tgctactaga atttagtaaa    1200

attttcttaa atattgccaa atatgttttt tccacgtgtt aatttggacg aatccagtaa    1260

attttgctta actttatatt tgtattaaaa aaattagtaa ctatatataa atattttaat    1320

tatggacccg gtaactaaaa cgaagataca aattccaaga caaattcaga aatcataaac    1380

atcaaatctt gtttgtacct atgaatgcat tccttaaaat atactacaag ttagggtgtt    1440

gtcactttct tgaagcatat tccgactgag tcttgtagaa tctcatgagc gttaggcctt    1500

atcgcttcaa ttaggcaatt acttacctcc tctgtacttt aagaaaattc aatgtagtac    1560

accattatta agttcatttc ataaataaaa ttaattctgt cacctctata acatataaga    1620

acgtatattt tccaagctag atatatctaa catgaatgac tttgtgaaat tcttttgcca    1680

agttaaagaa aaaaaatggt gtccaaagaa taaagagaaa aggcccctaa taaaaaaata    1740

atttattaat tagagttgtt caaacaatca cgtcaataat ggttttcatc aagaatgact    1800

agtggcggct cttatctcga gcgatgtggc atgattttga ctttaacact aatatcaaat    1860

gctttctata tcaattatcc tatagagtct gctaacaagt aattcaattc tttaatttct    1920

tttacaaatt ccagactttt caagtcttct tccctattaa aacccaccca ctctattcct    1980

tgtttctcac caaaacccaa a                                              2001
```

<210> SEQ ID NO 18
<211> LENGTH: 2001
<212> TYPE: DNA
<213> ORGANISM: Nicotiana sp.

<400> SEQUENCE: 18

```
atgaacgggt cgattttagg gtatttgaca tttaatcctc tcggtctcac ggtaggcatt      60

cggatcgata tttaaggaaa ataaaatata aacaaactaa tatatatata tatatatata    120

tacacgacac cttaagatat tagaagttgg ccaagaaatt taaatgaaca ataacaaaag    180

atttgctttt tgcatctcgt tgtccatgag attttctttg tctgctcacg acatttccac    240

cttaaccatc taaatcaaaa gttaatttgt tcctacaata cgatatcgca atcttattac    300

gccctccatt gcattttatg gaaggtatta tttttgtgg agttatacta ttttttcttt    360

agttataatt ttcttatttt tttttaaaaa aacattttga atcattagct atgtagtact    420

gttcgtgtaa tttataaata tatataaaaa aatttaaaaa aatgaggaat taatagtaaa    480

ttcacatcga aaatcaagtg ttttgactat cctactccac accctgtcac ataaattagg    540

aaaaagaaag aaaaaaagaa aagaaaagaa ataccttcca atttactgct tccctttaag    600

aacatgaaaa atcttgctaa tagattgcta gtagttgttt tctaaataac tcacgtctct    660

atcttgtctg ccaccttgaa aatatatgac tgtttctatc ttttctttag ataataatag    720

ttgagcaatc aatatctaaa actgtttttt tctttcatct taatctaatc attaagtaat    780

caatgtattt ttaaccagtg ctttattttt gctttgggta agattgtttc atctatataa    840

catttgttcc tcaccaatta ctaccattaa acatgaacaa aatgtttcat ggacagtgca    900

ttcttttccc ttataaatca cgtatctatc tatttctcca ccttaaatcc atatatatat    960
```

```
atatatatat atatatatat atatatgttt catggacagt gcattctttt cccttataaa   1020
tcacgtatct atctatttct ccaccttaaa tccatatata tatatatata tatatatata   1080
tatatatata tatatatata tatatatata tatatatata tatatatata tacttttaat   1140
attgtatcct attaaggatc aatatttttt cttctcgttt tctgcgttga gtaaggtatt   1200
aggtagattg gttttaaagt tgtacctccc tcttaactcc tcgtctttaa taacgttaaa   1260
tttagactgc ttgacttatc tcatgaataa tgcaacgtgt tccatataat tcagatctcc   1320
atctctttta ctaccttgaa tatatataat attgttatga agttaaacta aaagaacaaa   1380
aaaatataga gagaaataac aacttttaaa taacaataat agtaaaacta attcatacat   1440
tgtgagactt gatctcttat gaaagtctca aactttacag taaaatgaag gaaaactacc   1500
ggttatatcc atttataagt atataattat aaaaattggt gaattcataa aatattatta   1560
atattagtca attagctatt tgtaacccaa aaaaggttaa agttttgctt ttatttgagt   1620
gtgtattatt agaatagatt aagtacattt taagaagctt gaatttcagt tttgggatga   1680
tttggtggag ttttaaggtg gtttgaatta aaaattaaaa gtagaagatg attaaaattt   1740
catggtaaag gacaacagta acttagcaag accttataca cgtaatgagc taacactaat   1800
cttccatctc caataatgaa aatcatgagt ttcgtggatc acgttttata ctagcttttc   1860
atgcagctaa ctagaacata atatattatt taataataat aaaaaactag aatataatct   1920
atataaagac tacagcctct cagcactttc tcaccacttc cttttcaata cttactttct   1980
actatattga agaagaaaat a                                              2001
```

<210> SEQ ID NO 19
<211> LENGTH: 2001
<212> TYPE: DNA
<213> ORGANISM: Nicotiana sp.

<400> SEQUENCE: 19

```
ataaagtaaa aatgataaag ttgaagaaca attgttgagc acggcaaacg agaaaagcag     60
agtagaatat tctattgaag taaataataa tgtgtttaca aatgattggg gtccccttta    120
tataggaggg aaaaacccta atatggtaca ttcccaacta tggtgaagaa ttctattggt    180
attgttgtat aacaacctag tacggactcg tactattttg tacaaatctt atcccataat    240
ttatgccttg atccacgtgt tcttgagaaa ttcccgctct ttcttgagtg tcatcgaaat    300
tgtactgccc ttgaggcaga tcatgacggg tctccgattt tctcctcgag gtgcgcacat    360
cctggccagg gtcgattctt acttcgagct tcccgaactc gagctcgggg tatgatcaag    420
ccttcgaaat cgagctctcc aatttcgacc gtatacaatt ttaagaattg aatatacttt    480
gatcttttct tgaaaaagta tttatttatt ttatcttctc gcctagcgca atgaaatcaa    540
tatttattat tttcaaaaac ttacattttt ctttagtttt attttaataa tatttttata    600
ttttttctaa aattatattc ttattaatat aggtacacgc gcagagcgca taccttaata    660
ctagcttgag ggtacgtgtt ttgcatgtgt atcccatatt ctatatctat atctatacta    720
tattaaaaac actaacgctc ttggcgaaat gccgttcgct tattttatcc ttaaaaaata    780
ttatatattg gatatattat cctttaacat atataatcat cttcaggaac ttatattttt    840
attttattat ttaaatataa atttttaata aattagtact cattgagata gaatacacgc    900
gcatcgcgcg taccttgagg ctagtagaaa agaaaagtat gatagtatat gagtaacgtg    960
ttggaaatta agggaaggaa agaaaatttt ctttacatcc aaatttgaaa gttatttgac   1020
```

```
gtcatcgaga tgacggccat gttcaagttt tccacaaata atgtgaaaag aaaaagaaga   1080
agacacacac tgtgtttggt tttattatag ttttttcttt tagagaattg attgtacaaa   1140
ttattataag aaatagtata atataagatt tagaaataag attattagaa aaaacaaaca   1200
tcaaaaagta tttattttaa tttctttttc caatggacat tcccattctt ctgaaacaac   1260
atagataaaa atatgaaagc aaaaattatc agatcgttta atgcagataa tattaattaa   1320
cacattaacc ataaccaata ttttatttaa aaaaagcaca actgctagat caaaaaagtg   1380
tttaacttca tgcattgaca attttttaaa ataattttgc agcatcaggt aaaatatttt   1440
ttcttcgttt cccaccctgt gtacggtata cacgggtact tatattgggg cccaactaaa   1500
ttcggattcg tccggagaag tcccacattg gggcataaag cgctccctga cgaaggcgac   1560
tccataccca tggacttgaa cccgagacct ttggttaagg atgaacgaga cctccggtgc   1620
caggtaaaat attggtaact gcttatataa gtttaatatg gtaacctgag ccgaaggtct   1680
atcggaaaca gactttctgc cctatcaggg taggggtaag gtctgcatac acagtaccct   1740
ctccaaaccc cacttagtga gactttagtg ggtagttgtt gttgttattg ttatggtaac   1800
ctgggaaaca ggataaataa ctatctataa caggatatat tacattgata ttaccatgtc   1860
aaaaaattaa gcaagtacat gaataatcgc cgtgaaatct tcaagatttc tcctataaat   1920
acccttggta gtaaatctag tttttccatt caaagtacaa catttctcct atagtcatgg   1980
aatttgttct cttttcacaa a                                             2001
```

```
<210> SEQ ID NO 20
<211> LENGTH: 2001
<212> TYPE: DNA
<213> ORGANISM: Nicotiana sp.

<400> SEQUENCE: 20

aaatttttgc taaagtactc tctttttatt agttgaaaaa gaaattactc tttctataac     60
atgaaaataa agtactcatt tgttgaaatg aaagaaaata tttttttcta catcatgaaa    120
agatactcgt tatggggaca tggcgaatag gggtgggttg gtggggatat ggggaatagg    180
gggaagattg aaaaagagtt ttgggaaagt tttttttttgt tttgataggg aaaatatttt    240
cctccaattt gagaaaaatg agttcatggg cgtggggtgg aggtgggtag ctggaggtgt    300
ggggtgggtt ggtggggata tgtggaatag gggaagattg gaaaagagtt ttgggaaagt    360
attttttttt gttttgatgg ggaaaacatt ttcctctaat tgatgaaaaa tgagttcact    420
agaaaaatat tttccaaaat atttaatcca accaaacatg ataaaattaa aaaatattta    480
aaaatatttt cgttcgtacc aaacacaccc acagtggaac tgattaatct gtgtgttacg    540
taatttgtgc cgcttcatgc atttatttcg tgcgacgatt tggaattctt caataaataa    600
ctaatagtga aagatcatat aatactagta atactagctt taaaaaaatg taagtgtcgg    660
gagggtgacg gaaatgacaa ttatgtcata aacacacgtt gttcatactt cacatagggg    720
cgactctaag gctttgggac cataatagta gcagcagtag taatagtagt cgtaatcata    780
gtaacagtag tggtaataat cgtagtggtg atagtggtgg taatggtagt gatggtagtg    840
gtagtaataa tagtagcagt agtgatagta ataataatag taatagtaga tagtggtggt    900
agtggtagta gtaatagtgg tagtagatat tcaccaataa gcgtgctact taatagaata    960
aactacaaca atcgtttaaa ttgatcagga gtaaatactt ttgacaccgt caatactcaa   1020
aacttaagct attacgttat atatgtacgc ttattctttt tctcgtttgt gatgatagcc   1080
aaatcaaaat tttcaatttg agttctagac ctcgacattc gatagtccac cactttattt   1140
```

```
tttgtgctct ttttcctaat ttgtttttga aattcgcttt tttgtcttaa atgatttaaa   1200
agtaaatttt attgttagtg taaatatttt ataaaataaa tttaagagcc tctcaatatg   1260
atttcatctt aggccacgaa atccgttgag cacaggggcg gagccacctt atgggatgcg   1320
tgacaccgct tcatcggaaa gatttattaa atacatatat agacatatgc aaaaccaaat   1380
aatacataaa aacgataaag gtgacaacac ttgaaataaa ataactcatt gtccaactgg   1440
ttaagcgttt caacttctta gtatgtcggg agtacgaatc cttttggtgg aacccttatg   1500
tttttattgt tttgaagaca ttatttatta aaaaagaatt aaaatatatt ctatattagt   1560
aaggacctct aacaaaatta agcaacaaca aaagtcactt gaacaagaat tcatttgtta   1620
gtcaatttga caataaatat actcaaatca ttcttggaaa aagacatatt tggtactagt   1680
atttctaaca agattattat taatacattt agaaaataaa aactcgttgt aaagatttat   1740
agtaatgttt tgaattttat ttttttaat aaatacaatg tcattatagt tattcatttg   1800
ttcacttctt tgtttaccta ttacaaaata tgatacggac ttacgaaaaa ttttgcgtac   1860
gacactggtt gagctgcccc tgtgttcaca ttggaagaat aatatcatgg cacatttctt   1920
ctctataaat tcaaggttag catggtcgaa taaagcatcc aaaacaaata tcgcatatcc   1980
aatctaaaga aacaaaaaaa a                                             2001
```

```
<210> SEQ ID NO 21
<211> LENGTH: 2001
<212> TYPE: DNA
<213> ORGANISM: Nicotiana sp.

<400> SEQUENCE: 21

aagggaaaaa aataaaaata gaagagaaat gcaagggttt gctttcttgt accaaatatt     60
gaaagaaaaa aaatgttaca accatttcat ttgcaaaaaa aaaaaaataaa aaaataaatt   120
gaaattgaaa ttcaaaagta aagctgtttg gttcggaaca gaagtcgatt ttgaaaatcg   180
aaccgacgcg ttttacgaaa atgaaaacga ccatcgctag attttcacaa actaaaacaa   240
tttttccag aaaccttata cccataagca aattcaacac ataaattctc cccaattatt   300
tttaagaaaa tttagaacta ttttttaaga aattaaatta aaccaactca actattcaag   360
caacgcatta agtataacgg attcttaaag tctcgttctt aattctcgaa atgtgtcgag   420
aaatcacaac cgttaaatct aatgcctcaa agtaaagaaa atgaataagg agtgtagcaa   480
aaatatcaat gtggacaaga tggtcgtata taatttgtac aaagaaaatt caaatgggaa   540
tctcttaccc agtcaaaaca tgcatattct cttggattct aggcaagctt tcccattcca   600
aagtcaatgg aacgaaccaa ttattgctct ctaagtcttt ttctttcact aaagagtaaa   660
ttcaatatct tgacaattag gcactaagta aactgaagaa atagaatccc aatatttttc   720
cttcctcgta acaataacat taaagactca tcaatgtgac tcgaccaaag gttcagtagc   780
ttcattttca caaatagggg tgacaatttg aatccaaatc catctagccc gtccaaagat   840
taatggttga gctacaaaca ttttaattta tgagttaatt taggctgagc ccaagttaac   900
tcattatttt tttataactc attctgaccc attaaacagc ccaaatataa ctcatgaaac   960
tcacgcaaaa caaagaatct cagtccaatt tatctagaaa tttacttaat caccccaatt  1020
tcactttttt ttttgtattt ttaattttct gttcttttat ttttctgcac cacccaccct  1080
acccctatcc cccccaaacc ccctcaaaaa ttaattttta cctttttttt tttttaatat  1140
tttcaatttt ttttttgta tttctgcacc acccacccgc cctaaccccc tacccccggc    1200
```

```
aaaaaccctc aatttttttt acttttttttg tttatttttt ttaatttttt attttttttt   1260

tatttttcta caccacccta aaagtatagt acaaaattca gatttgaact ccttttttatt   1320

ggtagattaa tcaaagtaga aaaaaaaaga cagtttgaaa actacctcat tctataaggt   1380

tttcagaact cgtttgctta ctgagaaaat gaattattca cagttaaaat atattttaat   1440

gttcaatata agtaatatca gcataatttt tataccacat ctaacgaggg ataacaattc   1500

agggattagc tataccggaa taaaacaagt aaaatgataa aattgtcctt ctaccaaagc   1560

cttttaaagg aaaatcaagg ttaatattag aaacaaaaca ttatcaaagt taatttagtt   1620

taaaaccaaa taaatgcttt atacgtatat cttattacta atgcagtaaa ccaaataaat   1680

cagaggtact aaatgatctc aatattagta caatttagtt acgtactaaa atttctaaca   1740

taattttatt ctcgccaacc ctacaagtat agtactccaa cccctttctc ttggcaaaat   1800

aatccaatag gaaataaaga cggtaagaaa attggcacac gttatatatg acttttgaca   1860

ctatttaagc cagccaatgg cattagtggt tgcatacttt gaatgtagag aaataactaa   1920

taaagactgt tgagagttgt ttcttcttac ccctttttgaa gtttattttc ctcagatttt   1980

cacagttcca agcaagcact a                                              2001

<210> SEQ ID NO 22
<211> LENGTH: 847
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 22

gccattcttc agtccacaat aggcggcgga gcttcaccta cagcggcggc ggcggaaaac     60

ggtaccagaa aagtcatccc tctctcaaga gatgccctcc aagatttcat gttatcaatc    120

ataacccaaa aattacaaga tgagaaacaa cctttttacg tgttagattt gggtgaagtt    180

gtttctctta tggaccaatg gaaatctgct ctcccaaata tccgtccatt ttacgctgtt    240

aaatgtaacc ctgaaccgtc gttcctttca attttatctg ctatgggctc aaattttgat    300

tgtgctagcc gagctgaaat tgagtacgtt ttgtcccttg gcatttctaa taagatcttc    360

aacacctaca ccattttttt aatcactact acccattgca ttgaacaaac ttccaagttc    420

ttcttagctt cagattaaga aagtaccctt tcttggcttt gttgatgtgg taccattgtc    480

cattgtcttg tgtgtttcca gaaatgccaa gggacaaaac gtactcaatt tcagctcggc    540

tagcacaatc aaaatttgag cccatagcag ataaaattga aaggaacgac ggttcagggt    600

tacatttaac agcgtaaaat ggacggatat ttgggagagc agatttccat tggtccataa    660

gagaaacaac ttcacccaaa tctaacacgt aaaaaggttg tttctcatct tgtaattttt    720

gggttatgat tgataacatg aaatcttgga gggcatctct tgagagaggg atgacttttc    780

tggtaccgtt ttccgccgcc gccgctgtag gtgaagctcc gccgcctatt gtggactgaa    840

gaatggc                                                              847

<210> SEQ ID NO 23
<211> LENGTH: 1302
<212> TYPE: DNA
<213> ORGANISM: Nicotiana sp.

<400> SEQUENCE: 23

atggccggcc aaacaatcat cgtttccggg ttgaacccgg cggccattct tcagtccaca     60
```

```
attggcggcg gagcttctcc tacagcggcg gcggcggcgg aaaacggcac cagaaaagtc    120
atccctctct caagagatgc cttacaagat ttcatgttat caatcataac ccaaaaatta    180
caagatgaga aacaaccttt ttacgtgcta gacttgggtg aggttgtttc tcttatggac    240
caatggaaat ctgctctccc aaatatccgt ccattttacg ctgttaaatg taaccctgaa    300
ccgtcgttcc tttcaatttt atctgctatg ggctcaaatt ttgattgtgc tagccgagct    360
gaaattgagt atgttttatc tcttggcatt tcacctgacc gtattgtttt cgcaaatcca    420
tgcaaaccgg aatccgatat tatttttgca gcaaaagttg gggtgaatct tacaacctat    480
gattctgaag acgaggttta caagatccga aagcatcacc cgaaatccga actcttgctc    540
cgcatcaagc ccatgctcga cggcaacgcg agatgcccaa tgggcccgaa atacggcgcg    600
cttccagaag aagtcgaccc gctgctccgg gcagctcaag ccgcccgtct caccgtatcc    660
ggcgtctcat tccacatcgg tagcggagat gccgattcaa acgcttatct cggcgccata    720
gccgcggcta aggaagtgtt tgaaacagct gctaaactcg ggatgtcgaa aatgactgtt    780
ctagacgtcg gcggcgggtt tacatccggc caccagttca caaccgccgc cgtcgccgtt    840
aaatcagctt taaaacaaca cttcgatgac gaaccggagt tgacaatcat agctgaaccg    900
ggtcggtttt ttgcagagac ggcgtttact ttggcaacga cgattatagg gaaaagagtg    960
aggggtgaat tgagggagta ttggattaac gacgggctgt acggttcgat gaactgtgta   1020
ctttacgacc atgcgacggt gaatgcaacg ccgttagctg ttctgtcgaa tcgtagtaac   1080
gttacctgcg gcgggtcgaa aacgtttccg acgactgtgt ttgggcccac ttgtgatgct   1140
cttgatactg ttttaaggga ttaccagtta ccggagctgc aggttaatga ttggctggtt   1200
tttcctaata tgggtgctta tactaaagct gctgggtcca attttaatgg atttaatact   1260
tccgccattg ttactcacct cgcttattct tatccaagct ga                      1302
```

<210> SEQ ID NO 24
<211> LENGTH: 1299
<212> TYPE: DNA
<213> ORGANISM: Nicotiana sp.

<400> SEQUENCE: 24

```
atggccggcc aaacaataat cgtttccggg ttgaacccgg cggccattct tcagtccaca     60
ataggcggcg gagcttcacc tacagcggcg gcggcggaaa acggtaccag aaaagtcatc    120
cctctctcaa gagatgccct ccaagatttc atgttatcaa tcataaccca aaaattacaa    180
gatgagaaac aacctttta cgtgttagat ttgggtgaag ttgtttctct tatggaccaa     240
tggaaatctg ctctcccaaa tatccgtcca ttttacgctg ttaaatgtaa ccctgaaccg    300
tcgttccttt caattttatc tgctatgggc tcaaattttg attgtgctag ccgagctgaa    360
attgagtacg ttttgtccct tggcatttca cctgaccgta ttgtttttgc aaatccatgc    420
aaaccggaat ccgatattat ttttgcagca aaagttgggg tgaatttaac aacgtacgat    480
tcagaagacg aggtttacaa gatccgaaag catcacccga aatccgaact cttgctccga    540
atcaagccaa tgttcgacgg caacgcgagg tgcccaatgg gtccaaaata cggcgcgctt    600
ccagaagaag tcgagccgct gctccgggca gctcaggccg cccggctcac cgtctccggt    660
gtctccttcc acatcggcag cggagatgcc gattcaaacg cttatctcgg cgccatagcc    720
gcggctaagg aagtgtttga aacagctgct aaactcggta tgtcgaaaat gactgttcta    780
gacgtcggcg gcgggtttac atccggccac cagttcacaa ccgccgccgt cgctgttaga    840
tcagctttaa aacaacactt cgatgatcaa ccggagttga caatcatagc tgaaccgggc    900
```

```
cggtttttttg cggagactgc gtttacttta gcgacgacga ttatagggaa aagagtgagg    960

ggagaattga gggagtattg gattaacgac gggttgtacg gttcgatgaa ctgtgtactt   1020

tacgaccatg cgacggtgaa tgcaacgccg ttagctgttt tgtcgaatcg tactaacgtt   1080

acctgcggcg ggtcgaaaac gtttccgacg actgtgtttg ggcccacttg tgatgctctt   1140

gatactgttt taagggatta ccagttaccg gagctgcagg ttaatgattg gctagttttt   1200

cctaatatgg gtgcttatac taaagctgct gggtccaatt ttaatggatt taatacgtcc   1260

gccattgtta ctcacctcgc ttatgcttat ccaagctga                          1299
```

<210> SEQ ID NO 25
<211> LENGTH: 807
<212> TYPE: DNA
<213> ORGANISM: Nicotiana sp.

<400> SEQUENCE: 25

```
atgccagatt taatccgttc aattgcagag aaccatgaag ctggccagcc attttatctc     60

atggatttgg ctataattga aaagctaatg gacaaatgga accattcttt tccaaatata    120

aaacctttct atgctgtgaa atgcaacacc gaacctgctc ttcttactaa actagccaaa    180

ttgggtgcaa attttgattg tgctagccaa ctagaaatag aaaccgtctt aaatctcgaa    240

attggcccaa accaaatcat atttgctaac ccatgcaaag ctatttccca catcaaatac    300

gcagccaatg ttggggtcaa tctcacaact tttgattcca aacttgaaat tgacaagatc    360

aagaaatggc acccacattg tcatttgttg cttcgagtta aagcgcctaa tgatagcggc    420

gcattacgtc ccctgggaaa aaaattcggc gtgctaccag aagaagttga gccactactg    480

cattacgctt gtaatgtggt cgggctaaaa gttgtaggcg tttcatttca tgttggatct    540

atagcacaaa atcctagcat ttatcgcgag gcgattgcag ctgctagggc cgtttttgat    600

gttgctgatc atcttcgaat gcctaaaatg caaattttaa acattggtgg aggatttaga    660

tcaacaccat tgttcgagga aatagctagt gtagtaaacg aggcagtcca agattatttt    720

cccatgacta atttaacaat atttgcagag ccagggcggt ttttttgcag aaacggaatt    780

tacgttagtc gctcatgtga ttggtaa                                        807
```

<210> SEQ ID NO 26
<211> LENGTH: 1140
<212> TYPE: DNA
<213> ORGANISM: Nicotiana sp.

<400> SEQUENCE: 26

```
atgccagatt taatccgttc aattgcagag aaccatgaag ctggccagcc attttatctc     60

atggatttgg ctataattga aaagctaatg gacaaatgga accattcttt tccaaatata    120

aaacctttct atgctgtgaa atgcaacagc gaacctgctc ttcttactaa actagccaaa    180

ttgggtgcaa attttgattg tgctagccaa ctagaaatag aaaccgtctt aaatctcgga    240

attagcccaa accaaatcat atttgctaac ccatgcaaag ctatttccca catcaaatac    300

gcagccaatg ttagggtcaa tctcacaact tttgattcca aacttgaaat tgacaagatc    360

aagaaacggc acccacattg tcatttgttg cttcgagtta aagcgcctaa tgatagtggc    420

gcattacgtc ccctgggaaa aaaattcggc gtgctaccag aagaagttga gccactactg    480

cattacgctt gtaatgtggt cgggctaaaa gttgtaggcg tttcatttca tgttggatct    540

atagcacaaa atcctagcat ttatcgcgag gcgattgcag ctgctagggc cgtttttgat    600
```

```
gttgctgatc atcttcgaat gcctaaaatg caaattttaa acattggtgg aggatttaga    660

tcaacaccat tgttcgagga aatagctagt gtagtaaacg aggcagtcca agattatttt    720

cccatgacta atttaacaat atttgcagag ccagggcggt tttttgcaga aacggcattt    780

acgttagtcg ctcatgtgat tggtaaaaga gttagaggtg agaaaataga atattggatt    840

gatgaaggga tttatggatc atttaggcca acactttata atagttgttt tgtgggtata    900

aagccattgt tacttcaggt aacagaaaaa tcttgtcaaa tttatgagtc aactatttat    960

ggaccaagtt gtgactcact tgatgcagtg gctattgaca taaacttgcc ggagcttcat   1020

ttggatgacc tgatagtgtt ttctaatatg ggtgcatatt caacatgtgg aggaactaag   1080

ttcaatggat ttgatatgtt atctacacct gcctatcttg ttaactcaaa ttctagctaa   1140
```

```
<210> SEQ ID NO 27
<211> LENGTH: 1140
<212> TYPE: DNA
<213> ORGANISM: Nicotiana sp.

<400> SEQUENCE: 27

atgccagatt taatccgttc aattgcagaa aaccatgaag ctggccagcc attttatcta     60

cttgatttgg ctataattga aaagcttatg gacaaatgga accattcttt tccaaatatg    120

aaacctttct atgctgtgaa atgcaacact gaacctgcac ttcttactaa actagccaaa    180

ttgggtgcaa attttgattg tgctagccaa ctagaaatag aaaccgtctt aaatctcgga    240

attagcccaa accaaatcat atttgctaac ccatgcaaag ctatttccca catcaaatac    300

gcagccactg ttggggtcaa tctcacaact tttgattcca aacttgaaat tgacaagatc    360

aagaaatggc aaccacaatg tcatttgttg cttcgaatta aagcccctag tgatagtggc    420

gcgttacgtc ccctgggaaa aaaatttggt gtattaccag aagaagttga gccattactg    480

cattatgctt ataatgtggt agggctgaaa gttgtaggcg tttcatttca cgttggatct    540

atagcacaag atcccagcat ttatcgcgag gcgattgcaa ctgctaggac cgtgtttgat    600

gttgttgatc atcttcgaat gcctaaaatg cagattttaa acattggtgg aggatttaga    660

tcaacaccat tgttcgagga aatagctagt gtggtaaatg aagcagtcca agattatttt    720

tccatgccta atttaacaat atttgcagag ccaggacggt tttttgcgga gacagccttt    780

acattagtca ctcatgtgat tggtaaaaga gttagaggtg aaaaaataga gtattggatt    840

gatgaaggga tttatggatc atttaggcca acactttata atagttgttt tgtgggtata    900

aaaccattgt tacgtcaggt aacagaaaaa tcttgtcaaa tttgtgagtc aactatttat    960

ggaccaagtt gtgactcact tgatgcagta gctattgaca taaaattgcc agagcttcat   1020

ttggatgacc tgatagtgtt ttacaacatg ggcgcatatt caatatgcgg aggaactaaa   1080

ttcaatggat ttgatatgtt atctacacct acctatcttg ttaacgcaaa ctctagctaa   1140
```

```
<210> SEQ ID NO 28
<211> LENGTH: 1053
<212> TYPE: DNA
<213> ORGANISM: Nicotiana sp.

<400> SEQUENCE: 28

atggacaaat ggaaccattc ttttccaaat ataaaacctt tctatgctgt gaaatgcaac     60

agtgaacctg cacttcttac taaactagcc aaattgggtg caaattttga ttgtgctagc    120

caactagaga tcgagaccgt cttaaatctc ggaattagcc ccaaccaaat catatttgct    180

aacccatgca aagctatttc ccacattaaa tacgcagcca atgttggggt caatctcaca    240
```

```
acttttgatt caaaacttga aattgacaag atcaagaaat ggcacccaca atgtcattta    300

ttgcttcgaa ttaaagcccc tagtgatagt ggctcgttac gtcccctggg aaaaaaattc    360

ggcgcgttac cagaagaagt tgagccacta ctgcattacg cttgtaatat ggtcgggcta    420

aaagttgtag gcgtttcatt tcacgttgga tctatagcac aagatcccag catttatcgc    480

gaggcgattg cagctgctag gaccgtgttt gatgttgctg atcatcttcg aatgcctaaa    540

atgcaaattt tagacattgg tggaggattt agatcgacac cattgttcga ggaaatagct    600

agtgtagtaa aaaaagcagt ccaagattat ttacccttgc ccaacttaac attatttgca    660

gagccagggc ggtttttgc agaaacggcc tttactttag tcactcatgt gattggtaaa    720

agagttagag gtgagaaaat agagtattgg attgatgaag ggatttatgg atcatttagg    780

ccaacgcttt acaatagttg ttttgtgggt attaagccat tttacgtca ggttgaagaa    840

aaatcttgtc aaatatgtga gtcaactatt tatggaccaa gttgtgactc acttgatgca    900

gtggctattg acataaaatt gcccgagctt catttggatg atctgatagt gttttataac    960

atgggcgcat attcaatatg tggaggaact aagttcaatg gatttgatat gttatctacc   1020

cctatctatc ttgttaattc aaattcaagc taa                               1053
```

```
<210> SEQ ID NO 29
<211> LENGTH: 433
<212> TYPE: PRT
<213> ORGANISM: Nicotiana sp.

<400> SEQUENCE: 29

Met Ala Gly Gln Thr Ile Ile Val Ser Gly Leu Asn Pro Ala Ala Ile
1               5                   10                  15

Leu Gln Ser Thr Ile Gly Gly Gly Ala Ser Pro Thr Ala Ala Ala Ala
            20                  25                  30

Ala Glu Asn Gly Thr Arg Lys Val Ile Pro Leu Ser Arg Asp Ala Leu
        35                  40                  45

Gln Asp Phe Met Leu Ser Ile Ile Thr Gln Lys Leu Gln Asp Glu Lys
    50                  55                  60

Gln Pro Phe Tyr Val Leu Asp Leu Gly Glu Val Val Ser Leu Met Asp
65                  70                  75                  80

Gln Trp Lys Ser Ala Leu Pro Asn Ile Arg Pro Phe Tyr Ala Val Lys
                85                  90                  95

Cys Asn Pro Glu Pro Ser Phe Leu Ser Ile Leu Ser Ala Met Gly Ser
            100                 105                 110

Asn Phe Asp Cys Ala Ser Arg Ala Glu Ile Glu Tyr Val Leu Ser Leu
        115                 120                 125

Gly Ile Ser Pro Asp Arg Ile Val Phe Ala Asn Pro Cys Lys Pro Glu
    130                 135                 140

Ser Asp Ile Ile Phe Ala Ala Lys Val Gly Val Asn Leu Thr Thr Tyr
145                 150                 155                 160

Asp Ser Glu Asp Glu Val Tyr Lys Ile Arg Lys His His Pro Lys Ser
                165                 170                 175

Glu Leu Leu Leu Arg Ile Lys Pro Met Leu Asp Gly Asn Ala Arg Cys
            180                 185                 190

Pro Met Gly Pro Lys Tyr Gly Ala Leu Pro Glu Glu Val Asp Pro Leu
        195                 200                 205

Leu Arg Ala Ala Gln Ala Ala Arg Leu Thr Val Ser Gly Val Ser Phe
    210                 215                 220
```

```
His Ile Gly Ser Gly Asp Ala Asp Ser Asn Ala Tyr Leu Gly Ala Ile
225                 230                 235                 240

Ala Ala Ala Lys Glu Val Phe Glu Thr Ala Ala Lys Leu Gly Met Ser
                245                 250                 255

Lys Met Thr Val Leu Asp Val Gly Gly Gly Phe Thr Ser Gly His Gln
            260                 265                 270

Phe Thr Thr Ala Ala Val Ala Val Lys Ser Ala Leu Lys Gln His Phe
        275                 280                 285

Asp Asp Glu Pro Glu Leu Thr Ile Ile Ala Glu Pro Gly Arg Phe Phe
    290                 295                 300

Ala Glu Thr Ala Phe Thr Leu Ala Thr Thr Ile Ile Gly Lys Arg Val
305                 310                 315                 320

Arg Gly Glu Leu Arg Glu Tyr Trp Ile Asn Asp Gly Leu Tyr Gly Ser
                325                 330                 335

Met Asn Cys Val Leu Tyr Asp His Ala Thr Val Asn Ala Thr Pro Leu
            340                 345                 350

Ala Val Leu Ser Asn Arg Ser Asn Val Thr Cys Gly Gly Ser Lys Thr
        355                 360                 365

Phe Pro Thr Thr Val Phe Gly Pro Thr Cys Asp Ala Leu Asp Thr Val
    370                 375                 380

Leu Arg Asp Tyr Gln Leu Pro Glu Leu Gln Val Asn Asp Trp Leu Val
385                 390                 395                 400

Phe Pro Asn Met Gly Ala Tyr Thr Lys Ala Ala Gly Ser Asn Phe Asn
                405                 410                 415

Gly Phe Asn Thr Ser Ala Ile Val Thr His Leu Ala Tyr Ser Tyr Pro
            420                 425                 430

Ser


<210> SEQ ID NO 30
<211> LENGTH: 432
<212> TYPE: PRT
<213> ORGANISM: Nicotiana sp.

<400> SEQUENCE: 30

Met Ala Gly Gln Thr Ile Ile Val Ser Gly Leu Asn Pro Ala Ala Ile
1               5                   10                  15

Leu Gln Ser Thr Ile Gly Gly Gly Ala Ser Pro Thr Ala Ala Ala Ala
            20                  25                  30

Glu Asn Gly Thr Arg Lys Val Ile Pro Leu Ser Arg Asp Ala Leu Gln
        35                  40                  45

Asp Phe Met Leu Ser Ile Ile Thr Gln Lys Leu Gln Asp Glu Lys Gln
    50                  55                  60

Pro Phe Tyr Val Leu Asp Leu Gly Glu Val Val Ser Leu Met Asp Gln
65                  70                  75                  80

Trp Lys Ser Ala Leu Pro Asn Ile Arg Pro Phe Tyr Ala Val Lys Cys
                85                  90                  95

Asn Pro Glu Pro Ser Phe Leu Ser Ile Leu Ser Ala Met Gly Ser Asn
            100                 105                 110

Phe Asp Cys Ala Ser Arg Ala Glu Ile Glu Tyr Val Leu Ser Leu Gly
        115                 120                 125

Ile Ser Pro Asp Arg Ile Val Phe Ala Asn Pro Cys Lys Pro Glu Ser
    130                 135                 140

Asp Ile Ile Phe Ala Ala Lys Val Gly Val Asn Leu Thr Thr Tyr Asp
145                 150                 155                 160
```

```
Ser Glu Asp Glu Val Tyr Lys Ile Arg Lys His His Pro Lys Ser Glu
                165                 170                 175

Leu Leu Leu Arg Ile Lys Pro Met Phe Asp Gly Asn Ala Arg Cys Pro
            180                 185                 190

Met Gly Pro Lys Tyr Gly Ala Leu Pro Glu Glu Val Glu Pro Leu Leu
        195                 200                 205

Arg Ala Ala Gln Ala Ala Arg Leu Thr Val Ser Gly Val Ser Phe His
    210                 215                 220

Ile Gly Ser Gly Asp Ala Asp Ser Asn Ala Tyr Leu Gly Ala Ile Ala
225                 230                 235                 240

Ala Ala Lys Glu Val Phe Glu Thr Ala Ala Lys Leu Gly Met Ser Lys
                245                 250                 255

Met Thr Val Leu Asp Val Gly Gly Gly Phe Thr Ser Gly His Gln Phe
            260                 265                 270

Thr Thr Ala Ala Val Ala Val Arg Ser Ala Leu Lys Gln His Phe Asp
        275                 280                 285

Asp Gln Pro Glu Leu Thr Ile Ile Ala Glu Pro Gly Arg Phe Phe Ala
    290                 295                 300

Glu Thr Ala Phe Thr Leu Ala Thr Thr Ile Ile Gly Lys Arg Val Arg
305                 310                 315                 320

Gly Glu Leu Arg Glu Tyr Trp Ile Asn Asp Gly Leu Tyr Gly Ser Met
                325                 330                 335

Asn Cys Val Leu Tyr Asp His Ala Thr Val Asn Ala Thr Pro Leu Ala
            340                 345                 350

Val Leu Ser Asn Arg Thr Asn Val Thr Cys Gly Gly Ser Lys Thr Phe
        355                 360                 365

Pro Thr Thr Val Phe Gly Pro Thr Cys Asp Ala Leu Asp Thr Val Leu
    370                 375                 380

Arg Asp Tyr Gln Leu Pro Glu Leu Gln Val Asn Asp Trp Leu Val Phe
385                 390                 395                 400

Pro Asn Met Gly Ala Tyr Thr Lys Ala Ala Gly Ser Asn Phe Asn Gly
                405                 410                 415

Phe Asn Thr Ser Ala Ile Val Thr His Leu Ala Tyr Ala Tyr Pro Ser
            420                 425                 430
```

<210> SEQ ID NO 31
<211> LENGTH: 268
<212> TYPE: PRT
<213> ORGANISM: Nicotiana sp.

<400> SEQUENCE: 31

```
Met Pro Asp Leu Ile Arg Ser Ile Ala Glu Asn His Glu Ala Gly Gln
1               5                   10                  15

Pro Phe Tyr Leu Met Asp Leu Ala Ile Ile Glu Lys Leu Met Asp Lys
            20                  25                  30

Trp Asn His Ser Phe Pro Asn Ile Lys Pro Phe Tyr Ala Val Lys Cys
        35                  40                  45

Asn Thr Glu Pro Ala Leu Leu Thr Lys Leu Ala Lys Leu Gly Ala Asn
    50                  55                  60

Phe Asp Cys Ala Ser Gln Leu Glu Ile Glu Thr Val Leu Asn Leu Glu
65                  70                  75                  80

Ile Gly Pro Asn Gln Ile Ile Phe Ala Asn Pro Cys Lys Ala Ile Ser
                85                  90                  95

His Ile Lys Tyr Ala Ala Asn Val Gly Val Asn Leu Thr Thr Phe Asp
            100                 105                 110
```

```
Ser Lys Leu Glu Ile Asp Lys Ile Lys Lys Trp His Pro His Cys His
        115                 120                 125

Leu Leu Leu Arg Val Lys Ala Pro Asn Asp Ser Gly Ala Leu Arg Pro
    130                 135                 140

Leu Gly Lys Lys Phe Gly Val Leu Pro Glu Glu Val Glu Pro Leu Leu
145                 150                 155                 160

His Tyr Ala Cys Asn Val Val Gly Leu Lys Val Val Gly Val Ser Phe
                165                 170                 175

His Val Gly Ser Ile Ala Gln Asn Pro Ser Ile Tyr Arg Glu Ala Ile
            180                 185                 190

Ala Ala Ala Arg Ala Val Phe Asp Val Ala Asp His Leu Arg Met Pro
        195                 200                 205

Lys Met Gln Ile Leu Asn Ile Gly Gly Gly Phe Arg Ser Thr Pro Leu
    210                 215                 220

Phe Glu Glu Ile Ala Ser Val Val Asn Glu Ala Val Gln Asp Tyr Phe
225                 230                 235                 240

Pro Met Thr Asn Leu Thr Ile Phe Ala Glu Pro Gly Arg Phe Phe Cys
                245                 250                 255

Arg Asn Gly Ile Tyr Val Ser Arg Ser Cys Asp Trp
            260                 265


<210> SEQ ID NO 32
<211> LENGTH: 379
<212> TYPE: PRT
<213> ORGANISM: Nicotiana sp.

<400> SEQUENCE: 32

Met Pro Asp Leu Ile Arg Ser Ile Ala Glu Asn His Glu Ala Gly Gln
1               5                   10                  15

Pro Phe Tyr Leu Met Asp Leu Ala Ile Ile Glu Lys Leu Met Asp Lys
            20                  25                  30

Trp Asn His Ser Phe Pro Asn Ile Lys Pro Phe Tyr Ala Val Lys Cys
        35                  40                  45

Asn Ser Glu Pro Ala Leu Leu Thr Lys Leu Ala Lys Leu Gly Ala Asn
    50                  55                  60

Phe Asp Cys Ala Ser Gln Leu Glu Ile Glu Thr Val Leu Asn Leu Gly
65                  70                  75                  80

Ile Ser Pro Asn Gln Ile Ile Phe Ala Asn Pro Cys Lys Ala Ile Ser
                85                  90                  95

His Ile Lys Tyr Ala Ala Asn Val Arg Val Asn Leu Thr Thr Phe Asp
            100                 105                 110

Ser Lys Leu Glu Ile Asp Lys Ile Lys Lys Arg His Pro His Cys His
        115                 120                 125

Leu Leu Leu Arg Val Lys Ala Pro Asn Asp Ser Gly Ala Leu Arg Pro
    130                 135                 140

Leu Gly Lys Lys Phe Gly Val Leu Pro Glu Glu Val Glu Pro Leu Leu
145                 150                 155                 160

His Tyr Ala Cys Asn Val Val Gly Leu Lys Val Val Gly Val Ser Phe
                165                 170                 175

His Val Gly Ser Ile Ala Gln Asn Pro Ser Ile Tyr Arg Glu Ala Ile
            180                 185                 190

Ala Ala Ala Arg Ala Val Phe Asp Val Ala Asp His Leu Arg Met Pro
        195                 200                 205

Lys Met Gln Ile Leu Asn Ile Gly Gly Gly Phe Arg Ser Thr Pro Leu
```

```
    210                 215                 220

Phe Glu Glu Ile Ala Ser Val Val Asn Glu Ala Val Gln Asp Tyr Phe
225                 230                 235                 240

Pro Met Thr Asn Leu Thr Ile Phe Ala Glu Pro Gly Arg Phe Phe Ala
                245                 250                 255

Glu Thr Ala Phe Thr Leu Val Ala His Val Ile Gly Lys Arg Val Arg
            260                 265                 270

Gly Glu Lys Ile Glu Tyr Trp Ile Asp Glu Gly Ile Tyr Gly Ser Phe
        275                 280                 285

Arg Pro Thr Leu Tyr Asn Ser Cys Phe Val Gly Ile Lys Pro Leu Leu
    290                 295                 300

Leu Gln Val Thr Glu Lys Ser Cys Gln Ile Tyr Glu Ser Thr Ile Tyr
305                 310                 315                 320

Gly Pro Ser Cys Asp Ser Leu Asp Ala Val Ala Ile Asp Ile Asn Leu
                325                 330                 335

Pro Glu Leu His Leu Asp Asp Leu Ile Val Phe Ser Asn Met Gly Ala
            340                 345                 350

Tyr Ser Thr Cys Gly Gly Thr Lys Phe Asn Gly Phe Asp Met Leu Ser
        355                 360                 365

Thr Pro Ala Tyr Leu Val Asn Ser Asn Ser Ser
    370                 375


<210> SEQ ID NO 33
<211> LENGTH: 379
<212> TYPE: PRT
<213> ORGANISM: Nicotiana sp.

<400> SEQUENCE: 33

Met Pro Asp Leu Ile Arg Ser Ile Ala Glu Asn His Glu Ala Gly Gln
1               5                   10                  15

Pro Phe Tyr Leu Leu Asp Leu Ala Ile Ile Glu Lys Leu Met Asp Lys
            20                  25                  30

Trp Asn His Ser Phe Pro Asn Met Lys Pro Phe Tyr Ala Val Lys Cys
        35                  40                  45

Asn Thr Glu Pro Ala Leu Leu Thr Lys Leu Ala Lys Leu Gly Ala Asn
    50                  55                  60

Phe Asp Cys Ala Ser Gln Leu Glu Ile Glu Thr Val Leu Asn Leu Gly
65                  70                  75                  80

Ile Ser Pro Asn Gln Ile Ile Phe Ala Asn Pro Cys Lys Ala Ile Ser
                85                  90                  95

His Ile Lys Tyr Ala Ala Thr Val Gly Val Asn Leu Thr Thr Phe Asp
            100                 105                 110

Ser Lys Leu Glu Ile Asp Lys Ile Lys Lys Trp Gln Pro Gln Cys His
        115                 120                 125

Leu Leu Leu Arg Ile Lys Ala Pro Ser Asp Ser Gly Ala Leu Arg Pro
    130                 135                 140

Leu Gly Lys Lys Phe Gly Val Leu Pro Glu Glu Val Glu Pro Leu Leu
145                 150                 155                 160

His Tyr Ala Tyr Asn Val Val Gly Leu Lys Val Val Gly Val Ser Phe
                165                 170                 175

His Val Gly Ser Ile Ala Gln Asp Pro Ser Ile Tyr Arg Glu Ala Ile
            180                 185                 190

Ala Thr Ala Arg Thr Val Phe Asp Val Val Asp His Leu Arg Met Pro
        195                 200                 205
```

```
Lys Met Gln Ile Leu Asn Ile Gly Gly Gly Phe Arg Ser Thr Pro Leu
    210                 215                 220

Phe Glu Glu Ile Ala Ser Val Val Asn Glu Ala Val Gln Asp Tyr Phe
225                 230                 235                 240

Ser Met Pro Asn Leu Thr Ile Phe Ala Glu Pro Gly Arg Phe Phe Ala
                245                 250                 255

Glu Thr Ala Phe Thr Leu Val Thr His Val Ile Gly Lys Arg Val Arg
            260                 265                 270

Gly Glu Lys Ile Glu Tyr Trp Ile Asp Glu Gly Ile Tyr Gly Ser Phe
        275                 280                 285

Arg Pro Thr Leu Tyr Asn Ser Cys Phe Val Gly Ile Lys Pro Leu Leu
    290                 295                 300

Arg Gln Val Thr Glu Lys Ser Cys Gln Ile Cys Glu Ser Thr Ile Tyr
305                 310                 315                 320

Gly Pro Ser Cys Asp Ser Leu Asp Ala Val Ala Ile Asp Ile Lys Leu
                325                 330                 335

Pro Glu Leu His Leu Asp Asp Leu Ile Val Phe Tyr Asn Met Gly Ala
            340                 345                 350

Tyr Ser Ile Cys Gly Gly Thr Lys Phe Asn Gly Phe Asp Met Leu Ser
        355                 360                 365

Thr Pro Thr Tyr Leu Val Asn Ala Asn Ser Ser
    370                 375


<210> SEQ ID NO 34
<211> LENGTH: 350
<212> TYPE: PRT
<213> ORGANISM: Nicotiana sp.

<400> SEQUENCE: 34

Met Asp Lys Trp Asn His Ser Phe Pro Asn Ile Lys Pro Phe Tyr Ala
1               5                   10                  15

Val Lys Cys Asn Ser Glu Pro Ala Leu Leu Thr Lys Leu Ala Lys Leu
            20                  25                  30

Gly Ala Asn Phe Asp Cys Ala Ser Gln Leu Glu Ile Glu Thr Val Leu
        35                  40                  45

Asn Leu Gly Ile Ser Pro Asn Gln Ile Ile Phe Ala Asn Pro Cys Lys
    50                  55                  60

Ala Ile Ser His Ile Lys Tyr Ala Ala Asn Val Gly Val Asn Leu Thr
65                  70                  75                  80

Thr Phe Asp Ser Lys Leu Glu Ile Asp Lys Ile Lys Lys Trp His Pro
                85                  90                  95

Gln Cys His Leu Leu Leu Arg Ile Lys Ala Pro Ser Asp Ser Gly Ser
            100                 105                 110

Leu Arg Pro Leu Gly Lys Lys Phe Gly Ala Leu Pro Glu Glu Val Glu
        115                 120                 125

Pro Leu Leu His Tyr Ala Cys Asn Met Val Gly Leu Lys Val Val Gly
    130                 135                 140

Val Ser Phe His Val Gly Ser Ile Ala Gln Asp Pro Ser Ile Tyr Arg
145                 150                 155                 160

Glu Ala Ile Ala Ala Ala Arg Thr Val Phe Asp Val Ala Asp His Leu
                165                 170                 175

Arg Met Pro Lys Met Gln Ile Leu Asp Ile Gly Gly Gly Phe Arg Ser
            180                 185                 190

Thr Pro Leu Phe Glu Glu Ile Ala Ser Val Val Lys Lys Ala Val Gln
        195                 200                 205
```

-continued

```
Asp Tyr Leu Pro Leu Pro Asn Leu Thr Leu Phe Ala Glu Pro Gly Arg
    210                 215                 220

Phe Phe Ala Glu Thr Ala Phe Thr Leu Val Thr His Val Ile Gly Lys
225                 230                 235                 240

Arg Val Arg Gly Glu Lys Ile Glu Tyr Trp Ile Asp Glu Gly Ile Tyr
                245                 250                 255

Gly Ser Phe Arg Pro Thr Leu Tyr Asn Ser Cys Phe Val Gly Ile Lys
            260                 265                 270

Pro Phe Leu Arg Gln Val Glu Glu Lys Ser Cys Gln Ile Cys Glu Ser
        275                 280                 285

Thr Ile Tyr Gly Pro Ser Cys Asp Ser Leu Asp Ala Val Ala Ile Asp
    290                 295                 300

Ile Lys Leu Pro Glu Leu His Leu Asp Asp Leu Ile Val Phe Tyr Asn
305                 310                 315                 320

Met Gly Ala Tyr Ser Ile Cys Gly Gly Thr Lys Phe Asn Gly Phe Asp
                325                 330                 335

Met Leu Ser Thr Pro Ile Tyr Leu Val Asn Ser Asn Ser Ser
            340                 345                 350


<210> SEQ ID NO 35
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 35

ttggctagga gagtcagaag tg                                              22


<210> SEQ ID NO 36
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 36

tcatcgaacg cttgttcccg tg                                              22
```

COMPOSITIONS AND METHODS FOR PRODUCING TOBACCO PLANTS AND PRODUCTS HAVING ALTERED ALKALOID LEVELS WITH DESIRABLE LEAF QUALITY

CROSS-REFERENCE TO RELATED APPLICATION

This application claims priority to U.S. Provisional Application No. 62/638,928, filed on Mar. 5, 2018, and is incorporated by reference herein in its entirety.

INCORPORATION OF SEQUENCE LISTING

A sequence listing contained in the ASCII file named "P34584US01_0025633_00547_SL.txt" which is 88,025 bytes (measured in MS-Windows®) and created on Feb. 14, 2019, is filed electronically herewith and incorporated by reference in its entirety.

FIELD

The present disclosure includes tobacco plants having altered total alkaloid and nicotine levels and commercially acceptable leaf grade, their development via breeding or transgenic approaches, and production of tobacco products from these tobacco plants.

BACKGROUND

Tobacco is one of the most widely grown non-food crops in the world with global production exceeding 7.4 million tons (FAOSTAT, Food and Agriculture Organization of the United Nations (FAO) (2014), faostat.fao.org) and resulting tobacco products having an annual global market size of USD 770 billion (Euromonitor International, 2016). Nicotine is the main alkaloid accumulating in tobacco leaves. Nicotine and other minor alkaloids are also precursors to tobacco-specific nitrosamines (TSNA). Demands exist for development of tobacco cultivars with lower levels of nicotine.

In commercial tobacco cultivars, nicotine represents 90-95% of the total alkaloid pool or 2-5% of total leaf dry weight (Saitoh F, Nona M, Kawashima N (1985). The alkaloid contents of sixty *Nicotiana* species. Phytochem. 24: 477-480). Nicotine is synthesized in the roots (Dawson R F (1942) Accumulation of nicotine in reciprocal grafts of tomato and tobacco. Am. J. Bot. 29: 66-71), and translocated through the xylem (Baldwin I T (1988). The alkaloidal responses of wild tobacco to real and simulated herbivory. Oecologia 77: 378-381) to aerial parts of the plant (Hildreth S B, Gehman E A, Yang H, Lu R H, Ritesh K C, Harich K C, Yu S, Lin J, Sandoe J L, Okumoto S, Murphyd, A S, Jeleskoaet J G (2011). Tobacco nicotine uptake permease (NUP1) affects alkaloid metabolism. Proc. Natl. Acad. Sci. USA 108: 18179-18184) where it accumulates in the leaves and is exuded by trichomes in response to insect herbivory (Kessler A, Baldwin I T (2002). Plant responses to insect herbivory: the emerging molecular analysis. Annu Rev. Plant Biol. 53: 299-328). Nicotine biosynthesis is influenced by genetic factors, plant development, biotic and abiotic stresses, phytohormonal signals and agronomic management practices such as topping and suckering (Wang S S, Shi Q M, Li W Q, Niu J F, Li C J, Zhang F S (2008). Nicotine concentration in leaves of flue-cured tobacco plants as affected by removal of the shoot apex and lateral buds. J. Integr. Plant Bio. 50: 958-964; Shoji T, Hashimoto T (2015). Stress-induced expression of NICOTINE2-locus genes and their homologs encoding Ethylene Response Factor transcription factors in tobacco. Phytochem. 113: 41-49). The genetic regulation of nicotine biosynthesis correlates to two independent loci, Nic1 and Nic2, which have a synergistic effect on nicotine levels, but the effect of Nic1 is ~2.4 times stronger than that of Nic2 (Legg P D, Collins G B (1971). Inheritance of percent total alkaloids in *Nicotiana tabacum* L. II. Genetic effects of two loci in Burley 21×LA Burley 21 populations. Can. J. Genet. Cytol. 13: 287-291). Both loci also influence the expression of numerous other genes unrelated to the nicotine biosynthesis pathway (Kidd S K, Melillo A A, Lu R H, Reed D G, Kuno N, Uchida K, Furuya M, Jelesko J G (2006). The A and B loci in tobacco regulate a network of stress response genes, few of which are associated with nicotine biosynthesis. Plant Mol. Biol. 60: 699-716; Shoji T, Kajikawa M, Hashimoto T (2010). Clustered transcription factor genes regulate nicotine biosynthesis in tobacco. Plant Cell 22: 3390-3409). Transcriptional analysis has shown that the Nic2 locus is a gene cluster that encodes at least seven ethylene response transcription factors (ERFs) (Shoji et al. 2010).

Homozygous mutations of either one or both loci can be used to create near-isogenic Burley 21 lines with reduced alkaloid levels, i.e. a high-intermediate (HI) variety with the genotype nic2, a low-intermediate (LI) variety with the genotype nic1, and a low-alkaloid (LA) variety with the genotype nic1nic2 (Legg P D, Chaplin J F, Collins G B (1969). Inheritance of percent total alkaloids in *Nicotiana tabacum* L. J. Hered. 60: 213-217; Legg et al. 1971). LA Burley 21 plants contain only ~5.7% of the total alkaloid levels found in the normal-alkaloid (NA) wild-type variety (Legg P D, Collins G B, Littion C C (1970). Registration of LA Burley 21 tobacco germplasm. Crop. Sci. 10: 212). In LA plants, the synergistic effect of the nic1 and nic2 mutations also causes an unfavorable leaf phenotype characterized by lower yields, delayed ripening and senescence, higher susceptibility to insect herbivory, and poor end-product quality after curing (Chaplin J F, Weeks W W (1976). Association between percent total alkaloids and other traits in flue-cured tobacco. Crop Sci. 16: 416-418; Legg et al. 1970; Chaplin J F, Burk L G (1983). Agronomic, chemical, and smoke characteristics of flue-cured tobacco lines with different levels of total alkaloids. Crop Sci. 75: 133-136).

There is a need to identify genes that restore unfavorable leaf phenotypes in the LA variety of tobacco plants, and to develop tobacco plants and products that contain altered nicotine levels (e.g., reduced nicotine) while maintaining (if not making superior) tobacco leaf quality.

SUMMARY

In an aspect, the present disclosure provide a tobacco plant comprising an inducible promoter operably linked to a transcribable DNA sequence encoding a non-coding RNA for suppression of an ornithine decarboxylase (ODC) gene.

In another aspect, the present disclosure provide a tobacco plant, or part thereof, comprising relative to a control tobacco plant: a first genome modification providing a lower level of nicotine or total alkaloid, and a second genome modification providing a comparable level of one or more traits selected from the group consisting of total leaf polyamine level, total root polyamine level, total leaf chlorophyll level, mesophyll cell number per leaf area unit, and leaf epidermal cell size; and wherein said control plant does not have both said first and said second genome modifications.

In an aspect, the present disclosure provide a method for improving leaf quality in a reduced-alkaloid tobacco plant, said method comprising: growing a tobacco plant, reducing the level of putrescine in said tobacco plant, harvesting leaves from said tobacco plant.

In another aspect, the present disclosure provide a method for improving leaf quality in a reduced-alkaloid tobacco plant, said method comprising: growing a tobacco plant, suppressing the expression or activity of an ornithine decarboxylase (ODC) gene in said tobacco plant, harvesting leaves from said tobacco plant In an aspect, a tobacco plant is provided having suppressed MYB8 activity via either transgene suppression, mutagenesis, or targeted genome editing.

BRIEF DESCRIPTION OF THE DRAWINGS

FIG. 1: Phenotypic characterization of *N. tabacum* L. cv. Burley 21 normal-alkaloid (NA) wild-type plants and three mutant varieties grown in the greenhouse.

FIG. 2: Polyamine analysis in field and greenhouse grown NA and LA plants.

BRIEF DESCRIPTION OF THE SEQUENCES

Figure 1A:
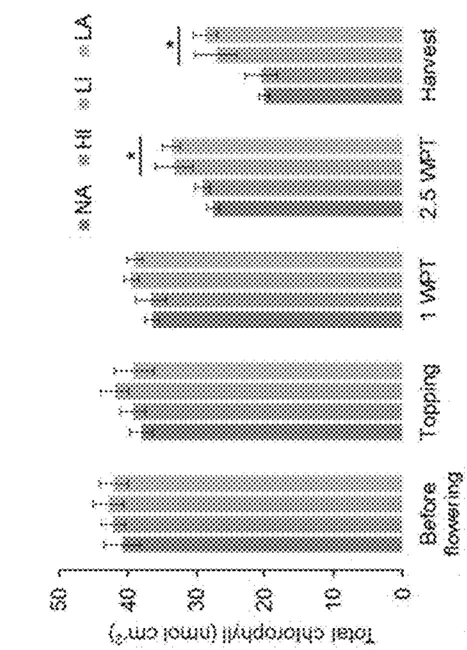
FIG. 1A: Total chlorophyll content of wild-type (NA) high-intermediate (HI, nic2), low-intermediate (LI, nic1) and low-alkaloid (LA, nic1nic2) lines grown in the greenhouse. Chlorophyll was measured twice per leaf in all leaves longer than 15 cm at different developmental stages: before flowering (2.5 weeks before topping), at topping, 1 week post topping (WPT), 2.5 WPT and harvest. Values are means of four biological replicates.

SEQ ID Nos: 1 to 11 set forth sequences of exemplary promoters for topping responsive root specific or preferred expression.

SEQ ID Nos: 11 to 21 set forth sequences of exemplary promoters for topping responsive leaf specific or preferred expression.

SEQ ID No: 22 sets forth a sequence of an exemplary DNA construct encoding a non-coding RNA suppressing an ornithine decarboxylase (ODC).

SEQ ID Nos: 23 to 28 set forth cDNA sequences of exemplary tobacco ODC genes.

SEQ ID Nos: 29 to 34 set forth amino acid sequences encoded by exemplary ODC genes.

SEQ ID Nos: 35 and 36 set forth two miRNA sequences targeting an ODC gene in accordance with the present disclosure.

Various sequences include "N" in nucleotide sequences or "X" in amino acid sequences. "N" can be any nucleotide, e.g., A, T, G, C, or a deletion or insertion of one or more nucleotides. In some instant, a string of "N" are shown. The number of "N" does not necessarily correlate with the actual number of undetermined nucleotides at that position. The actual nucleotide sequences can be longer or shorter than the shown segment of "N". Similarly, "X" can be any amino acid residue or a deletion or insertion of one or more amino acids. Again, the number of "X" does not necessarily correlate with the actual number of undetermined amino acids at that position. The actual amino acid sequences can be longer or shorter than the shown segment of "X". Notwithstanding the use of A, T, G, C (compared to A, U, G, C) in describing any SEQ ID in the sequence listing, that SEQ ID can also refer to a RNA sequence, depending on the context in which the SEQ ID is mentioned.

DETAILED DESCRIPTION

Unless defined otherwise, technical and scientific terms used herein have the same meaning as commonly understood by one of ordinary skill in the art. One skilled in the art will recognize many methods can be used in the practice of the present disclosure. Indeed, the present disclosure is in no way limited to the methods and materials described. For purposes of the present disclosure, the following terms are defined below.

Any references cited herein, including, e.g., all patents and publications are incorporated by reference in their entirety.

As used herein, the singular form "a," "an," and "the" include plural references unless the context clearly dictates otherwise. For example, the term "a compound" or "at least one compound" may include a plurality of compounds, including mixtures thereof.

The term "about" is used herein to mean approximately, roughly, around, or in the region of. When the term "about" is used in conjunction with a numerical range, it modifies that range by extending the boundaries above and below the numerical values set forth. To avoid any doubt, used herein, terms or phrases such as "about", "at least", "at least about", "at most", "less than", "greater than", "within" or alike, when followed by a series of list of numbers of percentages, such terms or phrases are deemed to modify each and every number of percentage in the series or list.

As used herein, a tobacco plant can be from any plant from the *Nicotiana* genus including, but not limited to *Nicotiana tabacum, Nicotiana amplexicaulis* PI 271989; *Nicotiana benthamiana* PI 555478; *Nicotiana bigelovii* PI 555485; *Nicotiana debneyi; Nicotiana excelsior* PI 224063; *Nicotiana glutinosa* PI 555507; *Nicotiana goodspeedii* PI 241012; *Nicotiana gossei* PI 230953; *Nicotiana hesperis* PI 271991; *Nicotiana knightiana* PI 555527; *Nicotiana maritima* PI 555535; *Nicotiana megalosiphon* PI 555536; *Nicotiana nudicaulis* PI 555540; *Nicotiana paniculata* PI 555545; *Nicotiana plumbaginifolia* PI 555548; *Nicotiana repanda* PI 555552; *Nicotiana rustica; Nicotiana suaveolens* PI 230960; *Nicotiana sylvestris* PI 555569; *Nicotiana tomentosa* PI 266379; *Nicotiana tomentosiformis*; and *Nicotiana trigonophylla* PI 555572.

In an aspect, the present disclosure provides tobacco plants, or part thereof, comprising an inducible promoter operably linked to a transcribable DNA sequence encoding a non-coding RNA for suppression of an ornithine decarboxylase (ODC) gene. In one aspect, tobacco plants comprise a mutation or a transgene conferring a reduced level of nicotine. In an aspect, tobacco plants are low-alkaloid tobacco plants. In one aspect, tobacco plants of the present disclosure comprise a nic1 mutation, a nic2 mutation, or both. In an aspect, tobacco plants comprise nicotine at a level below 1%, below 2%, below 5%, below 8%, below 10%, below 12%, below 15%, below 20%, below 25%, below 30%, below 40%, below 50%, below 60%, below 70%, or below 80% of the nicotine level of a control plant when grown in similar growth conditions, where the control plant shares an essentially identical genetic background with the tobacco plant except a low-nicotine conferring mutation or transgene. In another aspect, tobacco plants comprise nicotine or total alkaloids at a level below 1%, below 2%, below 5%, below 8%, below 10%, below 12%, below 15%, below 20%, below 25%, below 30%, below 40%, below 50%, below 60%, below 70%, or below 80% of the nicotine or total alkaloids level of the control plant when grown in similar growth conditions. In another aspect, tobacco plants comprise a total alkaloid level selected from the group consisting of less than 3%, less than 2.75%, less than 2.5%, less than 2.25%, less than 2.0%, less than 1.75%, less than 1.5%, less than 1.25%, less than 1%, less than 0.9%, less than 0.8%, less than 0.7%, less than 0.6%, less than 0.5%, less than 0.4%, less than 0.3%, less than 0.2%, less than 0.1%, and less than 0.05% of the nicotine level of a control plant when grown in similar growth conditions, where the control plant shares an essentially identical genetic background with the tobacco plant except a low-nicotine conferring mutation or transgene. In another aspect, tobacco plants comprise a nicotine or total alkaloid level selected from the group consisting of less than 3%, less than 2.75%, less than 2.5%, less than 2.25%, less than 2.0%, less than 1.75%, less than 1.5%, less than 1.25%, less than 1%, less than 0.9%, less than 0.8%, less than 0.7%, less than 0.6%, less than 0.5%, less than 0.4%, less than 0.3%, less than 0.2%, less than 0.1%, and less than 0.05% of the nicotine or total alkaloids level of the control plant when grown in similar growth conditions.

In an aspect, tobacco plants comprise a transgene or mutation directly suppressing the expression or activity of one or more, two or more, three or more, four or more, five or more, six or more, seven or more, eight or more, nine or more, ten or more, eleven or more, twelve or more, thirteen or more, fourteen or more, fifteen or more, sixteen or more, seventeen or more, eighteen or more, nineteen or more, twenty or more, or all twenty-one genes or loci encoding a protein selected from the group consisting of aspartate oxidase, agmatine deiminase (AIC), arginase, diamine oxidase, arginine decarboxylase (ADC), methylputrescine oxidase (MPO), NADH dehydrogenase, ornithine decarboxylase (ODC), phosphoribosylanthranilate isomerase (PRAI), putrescine N-methyltransferase (PMT), quinolate phosphoribosyl transferase (QPT), S-adenosyl-methionine synthetase (SAMS), A622, NBB1, BBL, MYC2, nic1, nic2, ethylene response factor (ERF) transcription factor, nicotine uptake permease (NUP), and MATE transporter. See Dewey and Xie, Molecular genetics of alkaloid biosynthesis in *Nicotiana tabacum*, Phytochemistry 94 (2013) 10-27.

In an aspect, tobacco plants further comprise one or more mutations in one or more, two or more, three or more, four or more, five or more, six or more, seven or more, eight or more, nine or more, or all ten genes selected from the group consisting of ERF32, ERF34, ERF39, ERF189, ERF115, ERF221, ERF104, ERF179, ERF17, and ERF168. In one aspect, tobacco plants further comprise one or more mutations in ERF189, ERF115, or both. In an aspect, tobacco plants further comprise one or more transgenes targeting and suppressing a gene encoding one or more, two or more, three or more, four or more, five or more, six or more, seven or more, eight or more, nine or more, or all ten proteins selected from the group consisting of ERF32, ERF34, ERF39, ERF189, ERF115, ERF221, ERF104, ERF179, ERF17, and ERF168.

In an aspect, tobacco plants are capable of producing leaves, when cured, having a USDA grade index value selected from the group consisting of 55 or more, 60 or more, 65 or more, 70 or more, 75 or more, 80 or more, 85 or more, 90 or more, and 95 or more. In another aspect, tobacco plants are capable of producing leaves, when cured, having a USDA grade index value comparable to that of a control plant when grown and cured in similar conditions, where the control plant shares an essentially identical genetic background with the tobacco plant except a low-nicotine conferring mutation or transgene. In a further aspect, tobacco plants are capable of producing leaves, when cured, having a USDA grade index value of at least about 65%, at least about 70%, at least about 75%, at least about 80%, at least about 85%, at least about 90%, at least about 95%, or at least about 98% of the USDA grade index value of a control plant when grown in similar conditions, where the control plant shares an essentially identical genetic background with the tobacco plant except a low-nicotine conferring mutation or transgene. In a further aspect, tobacco plants are capable of producing leaves, when cured, having a USDA grade index value of between 65% and 130%, between 70% and 130%, between 75% and 130%, between 80% and 130%, between 85% and 130%, between 90% and 130%, between 95% and 130%, between 100% and 130%, between 105% and 130%, between 110% and 130%, between 115% and 130%, or between 120% and 130% of the USDA grade index value of the control plant. In a further aspect, tobacco plants are capable of producing leaves, when cured, having a USDA grade index value of between 70% and 125%, between 75% and 120%, between 80% and 115%, between 85% and 110%, or between 90% and 100% of the USDA grade index value of the control plant.

In another aspect, tobacco plants are capable of producing leaves, when cured, having a USDA grade index value selected from the group consisting of 55 or more, 60 or more, 65 or more, 70 or more, 75 or more, 80 or more, 85 or more, 90 or more, and 95 or more. In another aspect, tobacco plants are capable of producing leaves, when cured, having a USDA grade index value selected from the group consisting of between 50 and 95, between 55 and 95, between 60 and 95, between 65 and 95, between 70 and 95, between 75 and 95, between 80 and 95, between 85 and 95, between 90 and 95, between 55 and 90, between 60 and 85, between 65 and 80, between 70 and 75, between 50 and 55, between 55 and 60, between 60 and 65, between 65 and 70, between 70 and 75, between 75 and 80, between 80 and 85, between 85 and 90, and between 90 and 95. In a further aspect, tobacco plants are capable of producing leaves, when cured, having a USDA grade index value of at least about 65%, at least about 70%, at least about 75%, at least about 80%, at least about 85%, at least about 90%, at least about 95%, or at least about 98% of the USDA grade index value of the control plant. In a further aspect, tobacco plants are capable of producing leaves, when cured, having a USDA grade index value of between 65% and 130%, between 70% and 130%, between 75% and 130%, between 80% and 130%, between 85% and 130%, between 90% and 130%, between 95% and 130%, between 100% and 130%, between 105% and 130%, between 110% and 130%, between 115% and 130%, or between 120% and 130% of the USDA grade index value of the control plant. In a further aspect, tobacco plants are capable of producing leaves, when cured, having a USDA grade index value of between 70% and 125%, between 75% and 120%, between 80% and 115%, between 85% and 110%, or between 90% and 100% of the USDA grade index value of the control plant.

In an aspect, the present disclosure also provides a tobacco variety, cultivar, or line comprising a mutation selected from the group consisting of a nic1 mutation, a nic2 mutation, and a combination thereof, where the tobacco variety, cultivar, or line has a leaf grade comparable to the leaf grade of a control tobacco variety, cultivar, or line when grown in similar growth conditions, where the control tobacco variety shares an essentially identical genetic background with the tobacco variety, cultivar, or line except the mutation.

In an aspect, the present disclosure further provides non-transgenic tobacco plants, or part thereof, comprising a nicotine or total alkaloid level selected from the group consisting of less than 3%, less than 2.75%, less than 2.5%, less than 2.25%, less than 2.0%, less than 1.75%, less than 1.5%, less than 1.25%, less than 1%, less than 0.9%, less than 0.8%, less than 0.7%, less than 0.6%, less than 0.5%, less than 0.4%, less than 0.3%, less than 0.2%, less than 0.1%, and less than 0.05%, where the tobacco plants are capable of producing leaves, when cured, having a USDA grade index value of 50 or more 55 or more, 60 or more, 65 or more, 70 or more, 75 or more, 80 or more, 85 or more, 90 or more, and 95 or more. In another aspect, such non-transgenic tobacco plants comprise a nicotine level of less than 2.0% and are capable of producing leaves, when cured, having a USDA grade index value of 70 or more. In a further aspect, such non-transgenic tobacco plants comprise a nicotine level of less than 1.0% and are capable of producing leaves, when cured, having a USDA grade index value of 70 or more.

In an aspect, the present disclosure also provides a tobacco plant, or part thereof, comprising a non-transgenic mutation, where the non-transgenic mutation reduces the nicotine or total alkaloid level of the tobacco plant to below 1%, below 2%, below 5%, below 8%, below 10%, below 12%, below 15%, below 20%, below 25%, below 30%, below 40%, below 50%, below 60%, below 70%, or below 80% of the nicotine level of a control plant when grown in similar growth conditions, where the tobacco plant is capable of producing leaves, when cured, having a USDA grade index value comparable to the USDA grade index value of the control plant, and where the control plant shares an essentially identical genetic background with the tobacco plant except the non-transgenic mutation.

In an aspect, the present disclosure provides tobacco plants, or part thereof, comprising a mutation in a gene or locus, where the mutation is absent from LA Burley 21. In an aspect, tobacco plants provided herein comprise a shorter chromosomal introgression at a locus of interest compared to LA Burley 21. In another aspect, tobacco plants provided herein comprise no deletion of a complete gene or a complete genic coding sequence in the locus of interest. In an aspect, tobacco plants provided herein are homozygous at the locus of interest. In another aspect, tobacco plants provided herein are heterozygous at the locus of interest. In an aspect, tobacco plants provided herein comprise a mutation selected from the group consisting of a point mutation, a deletion, an insertion, a duplication, and an inversion at the gene or locus of interest. In an aspect, mutations in the tobacco plants provided herein are introduced by an approach selected from the group consisting of random mutagenesis and targeted mutagenesis. In another aspect, mutations in the tobacco plants provided herein are introduced by a targeted mutagenesis approach selected from the group consisting of meganuclease, zinc finger nuclease, TALEN, and CRISPR.

As used herein, a mutation refers to an inheritable genetic modification introduced into a gene to alter the expression or activity of a product encoded by the gene. Such a modification can be in any sequence region of a gene, for example, in a promoter, 5' UTR, exon, intron, 3' UTR, or terminator region. In an aspect, a mutation reduces, inhibits, or eliminates the expression or activity of a gene product. In another aspect, a mutation increases, elevates, strengthens, or augments the expression or activity of a gene product. In an aspect, mutations are not natural polymorphisms that exist in a particular tobacco variety or cultivar. As used herein, a "mutant allele" refers to an allele from a locus where the allele comprises a mutation. As used herein, "mutagenic" refers to generating a mutation without involving a transgene or with no mutation-related transgene remaining in an eventual mutant. In an aspect, mutagenic is cisgenic. In another aspect, mutagenic is via gene or genome editing. In a further aspect, mutagenic is via random mutagenesis, for example, chemical (e.g., EMS) or physical (r-irradiation) mutagenesis.

In an aspect, tobacco plants provided herein comprise one or more mutations within one or more genes comprising a coding sequence having at least 80%, at least 85%, at least 90%, at least 95%, at least 97%, at least 98%, at least 99%, or 100% identity to a sequence selected from the group consisting of SEQ ID NOs: 23 to 28, and fragments thereof. In an aspect, one or more mutations reduce the expression or activity of one or more genes comprising a coding sequence having at least 80%, at least 85%, at least 90%, at least 95%, at least 97%, at least 98%, at least 99%, or 100% identity to a sequence selected from the group consisting of SEQ ID NOs: 23 to 28, and fragments thereof.

In an aspect, tobacco plants provided herein comprise one or more mutations within one or more genes encoding a polypeptide having at least 80%, at least 85%, at least 90%, at least 95%, at least 97%, at least 98%, at least 99%, or 100% identity to a sequence selected from the group consisting of SEQ ID NOs: 29 to 34, and fragments thereof. In an aspect, one or more mutations reduce the expression or activity of one or more genes encoding a polypeptide having at least 80%, at least 85%, at least 90%, at least 95%, at least 97%, at least 98%, at least 99%, or 100% identity to a sequence selected from the group consisting of SEQ ID NOs: 29 to 34, and fragments thereof.

LA Burley 21 (also referenced as LA BU21) is a low total alkaloid tobacco line produced by incorporation of a low alkaloid gene(s) from a Cuban cigar variety into Burley 21 through several backcrosses (Legg et al. 1970). It has approximately 0.2% total alkaloids (dry weight) compared to the about 3.5% (dry weight) of its parent, Burley 21. LA BU21 has a leaf grade well below commercially acceptable standards. LA BU21 also exhibits other unfavorable leaf phenotypes characterized by lower yields, delayed ripening and senescence, higher susceptibility to insect herbivory, and poor end-product quality after curing (Chaplin and Weeks, 1976; Legg et al. 1970; Chaplin and Burk 1983). LA BU21 leaves further exhibit traits such as higher polyamine content, higher chlorophyll content and more mesophyll cells per unit leaf area.

In plants, polyamines are reportedly involved in developmental, physiological and metabolic processes such as cell growth and division, stress tolerance, vascular differentiation, lignin polymerization, pathogen defense, senescence and ripening (Fariduddin Q, Varshney P, Yusuf M, Ahmad A (2013) Polyamines: potent modulators of plant responses to stress. J. Plant Interac. 8: 1-16; Kusano T, Suzuki H (2015). Polyamines a universal molecular nexus for growth, survival and specialized metabolism. Tokyo: Springer). Several studies have linked polyamines to the regulation of plant cell senescence (Sobieszczuk-Nowicka, E., Kubala, S., Zmienko, A., Malecka, A., Legocka, J. 2016. From accumulation to degradation: Reprograming polyamine metabolism facilitates dark-induced senescence in Barley leaf cells. Front. Plant Sci. doi: 10.3389/fpls.2015.01198). In fruit and vegetative tissues, polyamines act as anti-senescence and anti-ripening regulators that prevent the decay of chloroplast photosystem complexes and changes in cell wall/membrane composition (Lester G E (2000). Polyamines and their cellular anti-senescence properties in honey dew musk melon fruit. Plant Sci. 160: 105-112; Mattoo A K, Handa A K (2008). Higher polyamines restore and enhance metabolic memory in ripening fruit. Plant Sci. 174: 386-393; Serafini-Fracassini D, Di Sandro A, Del Duca S (2010). Spermine delays leaf senescence in *Lactuca sativa* and prevents the decay of chloroplast photosystems. Plant Physiol. Biochem. 48: 602-611). Higher levels of polyamines increase the longevity of tomato vines (Mehta R A, Cassol T, Li N, Ali N, Handa A K, Mattoo A K (2002). Engineered polyamine accumulation in tomato enhances phytonutrient content, juice quality and vine life. Nat. Biotechnol. 20: 613-618), and delayed ripening and leaf senescence was observed in transgenic tomato plants overexpressing a yeast spermidine synthase (Nambeesan S, Datsenka T, Ferruzzi M G, Malladi A, Mattoo A K, Handa A K (2010). Overexpression of yeast spermidine synthase impacts ripening, senescence and decay symptoms in tomato. Plant J. 63: 836-847). Polyamines may act directly by stabilizing cell walls or through crosstalk with phytohormones such as ethylene, abscisic acid, cytokinins and gibberellins (Kussano and Suzuki 2015).

In most plants, putrescine can be synthesized either directly from ornithine by ornithine decarboxylase (ODC) or from arginine via three enzymatic steps, initiated by arginine decarboxylase (ADC) (Michael A J, Furze J M, Rhodes M J, Burtin D (1996). Molecular cloning and functional identification of a plant ornithine decarboxylase cDNA. Biochem. J. 314: 241-248; Piotrowski M, Janowitz T, Kneifel H (2003). Plant C-N hydrolases and the identification of a plant N-carbamoylputrescine amidohydrolase involved in polyamine biosynthesis J. Biol. Chem. 278: 1708-1712; Illingworth C, Mayer M J, Elliot K, Hanfrey C, Walton N J, Michael A J (2003). The diverse bacterial origins of the *Arabidopsis* polyamine biosynthetic pathway FEBS Letters 549: 26-30). Previous studies have stated that the ADC route to putrescine has only a minor effect on the alkaloid profile of tobacco whereas the ODC pathway plays the major role in nicotine biosynthesis (Chintapakorn Y, Hamill J D (2007). Antisense-mediated reduction in ADC activity causes minor alterations in the alkaloid profile of cultured hairy root and regenerated transgenic plants of *Nicotiana tabacum*. Phytochem. 68: 2465-2479; DeBoer K D, Dalton H L, Edward F J, Hamill J D (2011). RNAi-mediated down-regulation of ornithine decarboxylase (ODC) leads to reduced nicotine and increased anatabine levels in transgenic *Nicotiana tabacum* L. Phytochem. 72: 344-355; DeBoer K D, Dalton H L, Edward F J, Ryan S M, Hamill J D (2013). RNAi-mediated down-regulation of ornithine decarboxylase (ODC) impedes wound-stress stimulation of anabasine synthesis in *Nicotiana glauca*. Phytochem. 86: 21-28; Dalton H L, Blomstedt C K, Neale A D, Gleadow R, DeBoer K D, Hamill J D (2016). Effects of down-regulating ornithine decarboxylase upon putrescine-associated metabolism and growth in *Nicotiana tabacum* L. J. Exp. Bot. 67: 3367-3381). Putrescine is converted to spermidine and then spermine by the successive addition of aminopropyl groups derived from decarboxylated S-adenosylmethionine (SAM), in reactions catalyzed by the enzymes spermidine synthase and spermine synthase, respectively. SAM is also a substrate for the biosynthesis of ethylene (Tiburcio A F, Altabella T, Bitrián M, Alcázar R (2014). The roles of polyamines during the lifespan of plants: from development to stress. Planta 240: 1-18), which regulates senescence and fruit ripening (Fluhr R, Mattoo A K (1996). Ethylene—biosynthesis and perception. Crit. Rev. Plant Sci. 15:479-523). The polyamine and ethylene biosynthesis pathways compete for the common precursor SAM but have opposing developmental effects, particularly during the developmental switch from vegetative growth to ripening/senescence (Nambeesan S, Handa A K, Mattoo A K (2008). Polyamines and regulation of ripening and senescence. In: Paliyath G, Murr D P, Handa A K, Lurie S (eds) Postharvest biology and technology of fruits, vegetables and flowers. Willey-Blackwell Publ, Ames. pp 319-340, Harpaz-Saad S, Yoon G M, Mattoo A K, Kieber J J (2012). The formation of ACC and competition between polyamines and ethylene for SAM. Annu. Plant Reviews. 44: 53-81, Gupta A, Pal R K, Rajam M V (2013). Delayed ripening and improved fruit processing quality in tomato by RNAi-mediated silencing of three homologs of 1-aminopropane-1-carboxylate synthase gene. J. Plant Physiol. 170: 987-995). Polyamine levels decrease and ethylene levels increase during the onset of fruit ripening in tomato (Saftner R A, Baldi B G (1990). Polyamine levels and tomato fruit development: possible interaction with ethylene. Plant Physiol. 92: 547-550; Morilla A, Garcia J M, Albi M A (1996). Free polyamine contents and decarboxylase activities during tomato development and ripening. J. Agri. Food Chem. 44: 2608-2611) and avocado (Kushad M M, Yelenosky G, Knight R (1988). Interrelationship of polyamine and ethylene biosynthesis during avocado fruit development and ripening. Plant Physiol. 87:463-467), which reflects the mutually antagonistic effect of ethylene on polyamine biosynthesis and vice versa (Harpaz-Saad et al. 2012; Anwar R, Mattoo A, HandaA (2015). Polyamine interactions with plant hormones: crosstalk at several levels in Kusano T, Suzuki H (eds). Polyamines a Universal Molecular Nexus for Growth, Survival and Specialized Metabolism. Tokyo: Springer. pp 267-303). However, transgenic tomato plants expressing yeast S-adenosylmethionine decarboxylase (SAMDC) under the control of the ripening-specific E8 promoter produced higher levels of ethylene and polyamines simultaneously during fruit ripening, indicating the absence of any competition for SAM in this system (Mehta R A, Cassol T, Li N, Ali N, Handa A K, Mattoo A K (2002). Engineered polyamine accumulation in tomato enhances phytonutrient content, juice quality and vine life. Nat. Biotechnol. 20: 613-618).

Without being bound to any scientific theory, the suppression of nicotine biosynthesis in LA tobacco plants can affect crosstalk between the nicotine, polyamine and ethylene pathways, resulting in the accumulation of putrescine. This would in turn increase metabolic flux towards the higher polyamines spermidine and spermine while inhibiting ethylene biosynthesis, causing a dramatic effect on leaf ripening and senescence.

In an aspect, the present disclosure provides tobacco plants, or part thereof, comprising a low nicotine or low alkaloid-conferring mutation or transgene and capable of producing a leaf comprising a comparable level of one or more polyamines relative to a comparable leaf of a control plant not comprising the same mutation or transgene. In one aspect, a comparable level of one or more polyamines is within 20%, 17.5%, 15%, 12.5%, 10%, 7.5%, 5%, 2.5%, or 1% of the level in a comparable leaf of a control plant not comprising the same mutation or transgene. In an aspect, a comparable level of one or more polyamines is between 0.5% and 1%, between 1% and 2%, between 2% and 3%, between 3% and 4%, between 4% and 5%, between 5% and 6%, between 6% and 7%, between 7% and 8%, between 8% and 9%, between 9% and 10%, between 11% and 12%, between 12% and 13%, between 13% and 14%, between 14% and 15%, between 15% and 16%, between 16% and 17%, between 17% and 18%, between 18% and 19%, or between 19% and 20% of the level in a comparable leaf of a control plant not comprising the same mutation or transgene. In a further aspect, a comparable level of one or more polyamines is between 0.5% and 5%, between 5% and 10%, or between 10% and 20% of the level in a comparable leaf of a control plant not comprising the same mutation or transgene.

In an aspect, the present disclosure provides tobacco plants, or part thereof, comprising a low nicotine or low alkaloid-conferring mutation or transgene and capable of producing a leaf comprising a comparable chlorophyll level relative to a comparable leaf of a control plant not comprising the same mutation or transgene. In one aspect, a comparable chlorophyll level is within 20%, 17.5%, 15%, 12.5%, 10%, 7.5%, 5%, 2.5%, or 1% of the level in a comparable leaf of a control plant not comprising the same mutation or transgene. In an aspect, a comparable chlorophyll level is between 0.5% and 1%, between 1% and 2%, between 2% and 3%, between 3% and 4%, between 4% and 5%, between 5% and 6%, between 6% and 7%, between 7% and 8%, between 8% and 9%, between 9% and 10%, between 11% and 12%, between 12% and 13%, between 13% and 14%, between 14% and 15%, between 15% and 16%, between 16% and 17%, between 17% and 18%, between 18% and 19%, or between 19% and 20% of the level in a comparable leaf of a control plant not comprising the same mutation or transgene. In a further aspect, a comparable chlorophyll level is between 0.5% and 5%, between 5% and 10%, or between 10% and 20% of the level in a comparable leaf of a control plant not comprising the same mutation or transgene.

In an aspect, the present disclosure provides tobacco plants, or part thereof, comprising a low nicotine or low alkaloid-conferring mutation or transgene and capable of producing a leaf comprising a comparable number of mesophyll cell per unit of leaf area relative to a comparable leaf of a control plant not comprising the same mutation or transgene. In one aspect, a comparable number of mesophyll cell per unit of leaf area is within 20%, 17.5%, 15%, 12.5%, 10%, 7.5%, 5%, 2.5%, or 1% of the level in a comparable leaf of a control plant not comprising the same mutation or transgene. In an aspect, a comparable number of mesophyll cell per unit of leaf area is between 0.5% and 1%, between 1% and 2%, between 2% and 3%, between 3% and 4%, between 4% and 5%, between 5% and 6%, between 6% and 7%, between 7% and 8%, between 8% and 9%, between 9% and 10%, between 11% and 12%, between 12% and 13%, between 13% and 14%, between 14% and 15%, between 15% and 16%, between 16% and 17%, between 17% and 18%, between 18% and 19%, or between 19% and 20% of the level in a comparable leaf of a control plant not comprising the same mutation or transgene. In a further aspect, a comparable number of mesophyll cell per unit of leaf area is between 0.5% and 5%, between 5% and 10%, or between 10% and 20° 4 of the level in a comparable leaf of a control plant not comprising the same mutation or transgene.

In an aspect, the present disclosure provides tobacco plants, or part thereof, comprising a low nicotine or low alkaloid-conferring mutation or transgene and capable of producing a leaf comprising a comparable epidermal cell size relative to a comparable leaf of a control plant not comprising the same mutation or transgene. In one aspect, a comparable epidermal cell size is within 20%, 17.5%, 15%, 12.5%, 10%, 7.5%, 5%, 2.5%, or 1% of the level in a comparable leaf of a control plant not comprising the same mutation or transgene. In an aspect, a comparable epidermal cell size is between 0.5% and 1%, between 1% and 2%, between 2% and 3%, between 3% and 4%, between 4% and 5%, between 5% and 6%, between 6% and 7%, between 7% and 8%, between 8% and 9%, between 9% and 10%, between 11% and 12%, between 12% and 13%, between 13% and 14%, between 14% and 15%, between 15% and 16%, between 16% and 17%, between 17% and 18%, between 18% and 19%, or between 19% and 20% of the level in a comparable leaf of a control plant not comprising the same mutation or transgene. In a further aspect, a comparable epidermal cell size is between 0.5% and 5%, between 5% and 10%, or between 10% and 20% of the level in a comparable leaf of a control plant not comprising the same mutation or transgene.

In an aspect, the present disclosure provides tobacco plants, or part thereof, comprising a low nicotine or low alkaloid-conferring mutation or transgene and capable of producing a leaf comprising a comparable leaf yield relative to a comparable leaf of a control plant not comprising the same mutation or transgene. In one aspect, a comparable leaf yield is within 20%, 17.5%, 15%, 12.5%, 10%, 7.5%, 5%, 2.5%, or 1% of the level in a comparable leaf of a control plant not comprising the same mutation or transgene. In an aspect, a comparable leaf yield is between 0.5° 4 and 1%, between 1% and 2%, between 2% and 3%, between 3% and 4%, between 4% and 5%, between 5% and 6%, between 6% and 7%, between 7% and 8%, between 8% and 9%, between 9% and 10%, between 11% and 12%, between 12% and 13%, between 13% and 14%, between 14% and 15%, between 15% and 16%, between 16% and 17%, between 17% and 18%, between 18% and 19%, or between 19% and 20% of the level in a comparable leaf of a control plant not comprising the same mutation or transgene. In a further aspect, a comparable leaf yield is between 0.5% and 5%, between 5% and 10%, or between 10% and 20% of the level in a comparable leaf of a control plant not comprising the same mutation or transgene.

In an aspect, the present disclosure provides tobacco plants, or part thereof, comprising a low nicotine or low alkaloid-conferring mutation or transgene and exhibiting a comparable insect herbivory susceptibility relative to a comparable leaf of a control plant not comprising the same mutation or transgene. In one aspect, a comparable insect herbivory susceptibility is within 20%, 17.5%, 15%, 12.5%, 10%, 7.5%, 5%, 2.5%, or 1% of the level in a comparable leaf of a control plant not comprising the same mutation or transgene. In an aspect, a comparable insect herbivory susceptibility is between 0.5% and 1%, between 1% and 2%, between 2% and 3%, between 3% and 4%, between 4% and 5%, between 5% and 6%, between 6% and 7%, between 7% and 8%, between 8% and 9%, between 9% and 10%, between 11% and 12%, between 12% and 13%, between 13% and 14%, between 14% and 15%, between 15% and 16%, between 16% and 17%, between 17% and 18%, between 18% and 19%, or between 19% and 20% of the level in a comparable leaf of a control plant not comprising the same mutation or transgene. In a further aspect, a comparable insect herbivory susceptibility is between 0.5% and 5%, between 5% and 10%, or between 10% and 20% of the level in a comparable leaf of a control plant not comprising the same mutation or transgene.

Insect herbivory susceptibility level can be assayed by methods known in the art, for example, in an insect feeding assay. In short, a quarter inch layer of 0.7% agar in water is added to a 100 mm Petri dish and allowed to solidify. Leaf discs are cut from the petri dish lid, placed in the plates and pushed gently into the agar. Leaf discs are taken from plants at the 4-5 leaf stage. Discs were taken from lamina only to exclude major midribs. A single disc is taken from each of the four largest leaves of the plant generating 4 replicates per plant. Four plants are sampled for a total of 16 biological replicates test line. A single budworm at the second instar stage is added to the leaf and allowed to feed for 48 hours at ambient temperature. After 48 hours the budworm larvae are weighed and final larval weights are recorded.

Unless specified otherwise, measurements of alkaloid, polyamine, or nicotine levels (or another leaf chemistry or property characterization) or leaf grade index values mentioned herein for a tobacco plant, variety, cultivar, or line can refer to average measurements, including, for example, depending on the context, an average of multiple leaves of a single plant or an average measurement from a population of tobacco plants from a single variety, cultivar, or line. In an aspect, the nicotine, alkaloid, or polyamine level (or another leaf chemistry or property characterization) of a tobacco plant is measured after topping in a pooled leaf sample collected from leaf number 3, 4, and 5 after topping. In another aspect, the nicotine, alkaloid, or polyamine level (or another leaf chemistry or property characterization) of a tobacco plant is measured after topping in a leaf having the highest level of nicotine, alkaloid, or polyamine (or another leaf chemistry or property characterization). In an aspect, the nicotine, alkaloid, or polyamine level of a tobacco plant is measured after topping in leaf number 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30. In another aspect, the nicotine, alkaloid, or polyamine level (or another leaf chemistry or property characterization) of a tobacco plant is measured after topping in a pool of two or more leaves with consecutive leaf numbers selected from the group consisting of leaf number 1, 2, 3, 4, 5, 6, 7, 8, 9, 10, 11, 12, 13, 14, 15, 16, 17, 18, 19, 20, 21, 22, 23, 24, 25, 26, 27, 28, 29, and 30. In another aspect, the nicotine, alkaloid, or polyamine level (or another leaf chemistry or property characterization) of a tobacco plant is measured after topping in a leaf with a leaf number selected from the group consisting of between 1 and 5, between 6 and 10, between 11 and 15, between 16 and 20, between 21 and 25, and between 26 and 30. In another aspect, the nicotine, alkaloid, or polyamine level (or another leaf chemistry or property characterization) of a tobacco plant is measured after topping in a pool of two or more leaves with leaf numbers selected from the group consisting of between 1 and 5, between 6 and 10, between 11 and 15, between 16 and 20, between 21 and 25, and between 26 and 30. In another aspect, the nicotine, alkaloid, or polyamine level (or another leaf chemistry or property characterization) of a tobacco plant is measured after topping in a pool of three or more leaves with leaf numbers selected from the group consisting of between 1 and 5, between 6 and 10, between 11 and 15, between 16 and 20, between 21 and 25, and between 26 and 30.

Alkaloid levels can be assayed by methods known in the art, for example by quantification based on gas-liquid chromatography, high performance liquid chromatography, radio-immunoassays, and enzyme-linked immunosorbent assays.

As used herein, leaf numbering is based on the leaf position on a tobacco stalk with leaf number 1 being the oldest leaf (at the base) after topping and the highest leaf number assigned to the youngest leaf (at the tip).

A population of tobacco plants or a collection of tobacco leaves for determining an average measurement (e.g., alkaloid or nicotine level or leaf grading) can be of any size, for example, 5, 10, 15, 20, 25, 30, 35, 40, or 50. Industry-accepted standard protocols are followed for determining average measurements or grad index values.

As used herein, "topping" refers to the removal of the stalk apex, including the SAM, flowers, and up to several adjacent leaves, when a tobacco plant is near vegetative maturity and around the start of reproductive growth. Typically, tobacco plants are topped in the button stage (soon after the flower begins to appear). For example, greenhouse or field-grown tobacco plants can be topped when 50% of the plants have at least one open flower. Topping a tobacco plant results in the loss of apical dominance and also induce increased alkaloid production.

Typically, the nicotine, alkaloid, or polyamine level (or another leaf chemistry or property characterization) of a tobacco plant is measured about 2 weeks after topping. Other time points can also be used. In an aspect, the nicotine, alkaloid, or polyamine level (or another leaf chemistry or property characterization) of a tobacco plant is measured about 1, 2, 3, 4, or 5 weeks after topping. In another aspect, the nicotine, alkaloid, or polyamine level (or another leaf chemistry or property characterization) of a tobacco plant is measured about 3, 5, 7, 10, 12, 14, 17, 19, or 21 days after topping.

As used herein, "similar growth conditions" refer to similar environmental conditions and/or agronomic practices for growing and making meaningful comparisons between two or more plant genotypes so that neither environmental conditions nor agronomic practices would contribute to or explain any difference observed between the two or more plant genotypes. Environmental conditions include, for example, light, temperature, water (humidity), and nutrition (e.g., nitrogen and phosphorus). Agronomic practices include, for example, seeding, clipping, undercutting, transplanting, topping, and suckering. See Chapters 4B and 4C of Tobacco, Production, Chemistry and Technology, Davis & Nielsen, eds., Blackwell Publishing, Oxford (1999), pp 70-103.

As used herein, "comparable leaves" refer to leaves having similar size, shape, age, and/or stalk position.

In an aspect, the present disclosure provides tobacco plants, or part thereof, comprising an inducible promoter operably linked to a transcribable DNA sequence encoding a non-coding RNA for suppression of an ornithine decarboxylase (ODC) gene. In one aspect, an inducible promoter is a topping-inducible promoter. In an aspect, an inducible promoter is also a tissue-specific or tissue-preferred promoter. In one aspect, a tissue-specific or tissue-preferred promoter is specific or preferred for one or more tissues or organs selected from the group consisting of shoot, root, leaf, stem, flower, sucker, root tip, mesophyll cells, epidermal cells, and vasculature. In a further aspect, a topping inducible promoter comprises a promoter sequence from a tobacco nicotine demethylase gene, for example, CYP82E4, CYP82E5, or CYP82E10.

Various types of promoters can be used here, which are classified according to a variety of criteria relating to the pattern of expression of a coding sequence or gene (including a transgene) operably linked to the promoter, such as constitutive, developmental, tissue-specific, tissue-preferred, inducible, etc. Promoters that initiate transcription in all or most tissues of the plant are referred to as "constitutive" promoters. Promoters that initiate transcription during certain periods or stages of development are referred to as "developmental" promoters. Promoters whose expression is enhanced in certain tissues of the plant relative to other plant tissues are referred to as "tissue-enhanced" or "tissue-preferred" promoters. Thus, a "tissue-preferred" promoter causes relatively higher or preferential expression in a specific tissue(s) of the plant, but with lower levels of expression in other tissue(s) of the plant. Promoters that express within a specific tissue(s) of the plant, with little or no expression in other plant tissues, are referred to as "tissue-specific" promoters. A promoter that expresses in a certain cell type of the plant is referred to as a "cell type specific" promoter. An "inducible" promoter is a promoter that initiates transcription in response to an environmental stimulus such as cold, drought, heat or light, or other stimuli, such as wounding or chemical application. A promoter may also be classified in terms of its origin, such as being heterologous, homologous, chimeric, synthetic, etc. A "heterologous" promoter is a promoter sequence having a different origin relative to its associated transcribable sequence, coding sequence, or gene (or transgene), and/or not naturally occurring in the plant species to be transformed. The term "heterologous" more broadly includes a combination of two or more DNA molecules or sequences when such a combination is not normally found in nature. For example, two or more DNA molecules or sequences would be heterologous with respect to each other if they are normally found in different genomes or at different loci in the same genome, or if they are not identically combined in nature.

In an aspect, an inducible promoter provides root specific or preferred expression. In one aspect, a root specific or preferred inducible promoter comprises a sequence selected from the group consisting of SEQ ID Nos: 1-11 and a functional fragment thereof. Table 1 provides a comparison of estimated leaf versus root specific expression level driven by SEQ ID Nos: 1-11.

In an aspect, an inducible promoter provides leaf specific or preferred expression. In one aspect, a leaf specific or preferred inducible promoter comprises a sequence selected from the group consisting of SEQ ID Nos: 12-21 and a functional fragment thereof. Table 2 provides a comparison of estimated leaf versus root specific expression level driven by SEQ ID Nos: 12-21.

TABLE 1

Exemplary inducible promoters for topping-responsive root specific or preferred expression

| | | Leaf | | | | | Root | | | |
|---|---|---|---|---|---|---|---|---|---|---|
| SEQ Id | Gene Id | Layby stage | Before Topping | 3 days after Topping | 4 wks after Topping | Senescence | Layby stage | Flowering time | 3 days after Topping | 3 days after topping (nitrogen deficient) |
| NO: 1 | g78655 | | | | | | | | | |
| NO: 2 | g72021 | | | | | | | | | |
| NO: 3 | g78252 | | | | | | | | | |
| NO: 4 | g65720 | | | | | | | | | |

TABLE 1-continued

Exemplary inducible promoters for topping-responsive root specific or preferred expression

| | | Leaf | | | | | Root | | | |
|---|---|---|---|---|---|---|---|---|---|---|
| SEQ Id | Gene Id | Layby stage | Before Topping | 3 days after Topping | 4 wks after Topping | Senescence | Layby stage | Flowering time | 3 days after Topping | 3 days after topping (nitrogen deficient) |
| NO: 5 | g74108 | | | | | | | | | |
| NO: 6 | g47466 | | | | | | | | | |
| NO: 7 | g102868 | | | | | | | | | |
| NO: 8 | g23057 | | | | | | | | | |
| NO: 9 | g34684 | | | | | | | | | |
| NO: 10 | g105948 | | | | | | | | | |
| NO: 11 | g81261 | | | | | | | | | |

TABLE 2

Exemplary inducible promoters for topping-responsive leaf specific or preferred expression

| SEQ Id | Gene | Before Topping | 1 day after Topping | 3 days after Topping | 1 week after Topping | 2 weeks after Topping | 3 weeks after Topping | Harvest time |
|---|---|---|---|---|---|---|---|---|
| | g2237 | | | | | | | |
| | g31142 | | | | | | | |
| | g75488 | | | | | | | |
| | g94193 | | | | | | | |
| | g34756 | | | | | | | |
| | g104299 | | | | | | | |
| | g44810 | | | | | | | |
| | g71671 | | | | | | | |
| | g29427 | | | | | | | |
| | g49024 | | | | | | | |

In an aspect, an inducible promoter is a heterologous to the operably linked transcribable DNA sequence. In one aspect, a transcribable DNA sequence encodes a non-coding RNA selected from the group consisting of microRNA (miRNA), anti-sense RNA, small interfering RNA (siRNA), a trans-acting siRNA (ta-siRNA), and hairpin RNA (hpRNA). In an aspect, a non-coding RNA comprises a nucleotide sequence having at least 99.9%, at least 99.5%, at least 99%, at least 98%, at least 97%, at least 96%, at least 95%, at least 94%, at least 93%, at least 92%, at least 91%, at least 90%, at least 85%, at least 80%, or at least 75% identity to a sequence selected from the group consisting of SEQ ID Nos: 35 and 36, and any portions thereof. In one aspect, a non-coding RNA is provided in an ODC RNAi construct comprising a nucleotide sequence having at least 99%, at least 97%, at least 95%, at least 90%, at least 85%, at least 80%, or at least 75% identity to SEQ ID No: 22.

"Alkaloids" are complex, nitrogen-containing compounds that naturally occur in plants, and have pharmacological effects in humans and animals. "Nicotine" is the primary natural alkaloid in commercialized cigarette tobacco and accounts for about 90 percent of the alkaloid content in *Nicotiana tabacum*. Other major alkaloids in tobacco include cotinine, nornicotine, myosmine, nicotyrine, anabasine and anatabine. Minor tobacco alkaloids include nicotine-n-oxide, N-methyl anatabine, N-methyl anabasine, pseudooxynicotine, 2,3 dipyridyl and others.

In an aspect, tobacco plants provided herein comprise a lower level of total alkaloid or an individual alkaloid compared to a control tobacco plant without a nic1 mutation and/or a nic2 mutation when grown in similar growth conditions. In another aspect, tobacco plants provided herein comprise a lower level of one or more alkaloids selected from the group consisting of cotinine, nornicotine, myosmine, nicotyrine, anabasine and anatabine, compared to a control tobacco plant when grown in similar growth conditions. In an aspect, a lower alkaloid or nicotine level refers to an alkaloid or nicotine level of below 1%, below 2%, below 5%, below 8%, below 10%, below 12%, below 15%, below 20%, below 25%, below 30%, below 40%, below 50%, below 60%, below 70%, or below 80% of the alkaloid or nicotine level of a control tobacco plant. In another aspect, a lower alkaloid or nicotine level refers to an alkaloid or nicotine level of about between 0.5% and 1%, between 1% and 2%, between 2% and 3%, between 3% and 4%, between 4% and 5%, between 5% and 6%, between 6% and 7%, between 7% and 8%, between 8% and 9%, between 9% and 10%, between 11% and 12%, between 12% and 13%, between 13% and 14%, between 14% and 15%, between 15% and 16%, between 16% and 17%, between 17% and 18%, between 18% and 19%, between 19% and 20%, between 21% and 22%, between 22% and 23%, between 23% and 24%, between 24% and 25%, between 25% and 26%, between 26% and 27%, between 27% and 28%, between 28% and 29%, or between 29% and 30% of the alkaloid or nicotine level of a control tobacco plant. In a further aspect, a lower alkaloid or nicotine level refers to an alkaloid or nicotine level of about between 0.5% and 5%, between 5% and 10%, between 10% and 20%, between 20% and 30% of the alkaloid or nicotine level of a control tobacco plant.

Alkaloid levels can be assayed by methods known in the art, for example by quantification based on gas-liquid chromatography, high performance liquid chromatography, radio-immunoassays, and enzyme-linked immunosorbent assays. For example, nicotinic alkaloid levels can be measured by a GC-FID method based on CORESTA Recommended Method No. 7, 1987 and ISO Standards (ISO TC 126N 394 E. See also Hibi et al., *Plant Physiology* 100: 826-35 (1992) for a method using gas-liquid chromatography equipped with a capillary column and an FID detector. Unless specified otherwise, all alkaloid levels described here are measured using a method in accordance with CORESTA Method No 62, *Determination of Nicotine in Tobacco and Tobacco Products by Gas Chromatographic Analysis*, February 2005, and those defined in the Centers for Disease Control and Prevention's *Protocol for Analysis of Nicotine, Total Moisture and pH in Smokeless Tobacco Products*, as published in the Federal Register Vol. 64, No. 55 Mar. 23, 1999 (and as amended in Vol. 74, No. 4, Jan. 7, 2009).

Alternatively, tobacco total alkaloids can be measured using a segmented-flow colorimetric method developed for analysis of tobacco samples as adapted by Skalar Instrument Co (West Chester, Pa.) and described by Collins et al., *Tobacco Science* 13:79-81 (1969). In short, samples of tobacco are dried, ground, and extracted prior to analysis of total alkaloids and reducing sugars. The method then employs an acetic acid/methanol/water extraction and charcoal for decolorization. Determination of total alkaloids was based on the reaction of cyanogen chloride with nicotine alkaloids in the presence of an aromatic amine to form a colored complex which is measured at 460 nm. Unless specified otherwise, total alkaloid levels or nicotine levels shown herein are on a dry weight basis (e.g., percent total alkaloid or percent nicotine).

In an aspect, tobacco plants provided herein comprise a lower level of nicotine compared to a control tobacco plant without a nic1 mutation and/or a nic2 mutation when grown in similar growth conditions. In an aspect, a lower nicotine level refers to an average nicotine level of below 1%, below 2%, below 5%, below 8%, below 10%, below 12%, below 15%, below 20%, below 25%, below 30%, below 40%, below 50%, below 60%, below 70%, or below 80% of the average nicotine level of a control tobacco plant. In another aspect, a lower nicotine level refers to an average nicotine level of about between 0.5% and 1%, between 1% and 2%, between 2% and 3%, between 3% and 4%, between 4% and 5%, between 5% and 6%, between 6% and 7%, between 7% and 8%, between 8% and 9%, between 9% and 10%, between 11% and 12%, between 12° 4 and 13%, between 13% and 14%, between 14% and 15%, between 15% and 16%, between 16° 4 and 17%, between 17% and 18%, between 18% and 19%, between 19% and 20%, between 21° 4 and 22%, between 22% and 23%, between 23% and 24%, between 24% and 25%, between 25° 4 and 26%, between 26% and 27%, between 27% and 28%, between 28% and 29%, or between 29° 4 and 30% of the average nicotine level of a control tobacco plant. In a further aspect, a lower nicotine level refers to an average nicotine level of about between 0.5% and 5%, between 5% and 10%, between 10% and 20%, between 20% and 30% of the average nicotine level of a control tobacco plant.

In an aspect, tobacco plants provided herein comprise an average nicotine or total alkaloid level selected from the group consisting of about 0.01%, 0.02%, 0.05%, 0.75%, 0.1%, 0.15%, 0.2%, 0.3%, 0.35%, 0.4%, 0.5%, 0.6%, 0.7%, 0.8%, 0.9%, 1%, 1.1%, 1.2%, 1.3%, 1.4%, 1.5%, 1.6%, 1.7%, 1.8%, 1.9%, 2%, 2.1%, 2.2%, 2.3%, 2.4%, 2.5%, 2.6%, 2.7%, 2.8%, 2.9%, 3%, 3.1%, 3.2%, 3.3%, 3.4%, 3.5%, 3.6%, 3.7%, 3.8%, 3.9%, 4%, 5%, 6%, 7%, 8%, and 9% on a dry weight basis. In another aspect, tobacco plants provided herein comprise an average nicotine or total alkaloid level selected from the group consisting of about between 0.01% and 0.02%, between 0.02% and 0.05%, between 0.05% and 0.75%, between 0.75% and 0.1%, between 0.1% and 0.15%, between 0.15% and 0.2%, between 0.2% and 0.3%, between 0.3% and 0.35%, between 0.35% and 0.4%, between 0.4% and 0.5%, between 0.5% and 0.6%, between 0.6% and 0.7%, between 0.7% and 0.8%, between 0.8% and 0.9%, between 0.9% and 1%, between 1% and 1.1%, between 1.1% and 1.2%, between 1.2% and 1.3%, between 1.3% and 1.4%, between 1.4% and 1.5%, between 1.5% and 1.6%, between 1.6% and 1.7%, between 1.7% and 1.8%, between 1.8° 4 and 1.9%, between 1.9% and 2%, between 2% and 2.1%, between 2.1% and 2.2%, between 2.2° 4 and 2.3%, between 2.3% and 2.4%, between 2.4% and 2.5%, between 2.5% and 2.6%, between 2.6% and 2.7%, between 2.7% and 2.8%, between 2.8% and 2.9%, between 2.9% and 3%, between 3% and 3.1%, between 3.1% and 3.2%, between 3.2% and 3.3%, between 3.3% and 3.4%, between 3.4% and 3.5%, and between 3.5% and 3.6% on a dry weight basis. In a further aspect, tobacco plants provided herein comprise an average nicotine or total alkaloid level selected from the group consisting of about between 0.01% and 0.1%, between 0.02% and 0.2%, between 0.03% and 0.3%, between 0.04% and 0.4%, between 0.05% and 0.5%, between 0.75% and 1%, between 0.1% and 1.5%, between 0.15% and 2%, between 0.2% and 3%, and between 0.3% and 3.5% on a dry weight basis.

The present disclosure also provides tobacco plants having altered nicotine levels without negative impacts over other tobacco traits, e.g., leaf grade index value. In an aspect, a low-nicotine or nicotine-free tobacco variety provides cured tobacco of commercially acceptable grade. Tobacco grades are evaluated based on factors including, but not limited to, the leaf stalk position, leaf size, leaf color, leaf uniformity and integrity, ripeness, texture, elasticity, sheen (related to the intensity and the depth of coloration of the leaf as well as the shine), hygroscopicity (the faculty of the tobacco leaves to absorb and to retain the ambient moisture), and green nuance or cast. Leaf grade can be determined, for example, using an Official Standard Grade published by the Agricultural Marketing Service of the US Department of Agriculture (7 U.S.C. § 511). See, e.g., Official Standard Grades for Burley Tobacco (U.S. Type 31 and Foreign Type 93), effective Nov. 5, 1990 (55 F.R. 40645); Official Standard Grades for Flue-Cured Tobacco (U.S. Types 11, 12, 13, 14 and Foreign Type 92), effective Mar. 27, 1989 (54 F.R. 7925); Official Standard Grades for Pennsylvania Seedleaf Tobacco (U.S. Type 41), effective Jan. 8, 1965 (29 F.R. 16854); Official Standard Grades for Ohio Cigar-Leaf Tobacco (U.S. Types 42, 43, and 44), effective Dec. 8, 1963 (28 F.R. 11719 and 28 F.R. 11926); Official Standard Grades for Wisconsin Cigar-Binder Tobacco (U.S. Types 54 and 55), effective Nov. 20, 1969 (34 F.R. 17061); Official Standard Grades for Wisconsin Cigar-Binder Tobacco (U.S. Types 54 and 55), effective Nov. 20, 1969 (34 F.R. 17061); Official Standard Grades for Georgia and Florida Shade-Grown Cigar-Wrapper Tobacco (U.S. Type 62), Effective April 1971. A USDA grade index value can be determined according to an industry accepted grade index. See, e.g., Bowman et al, *Tobacco Science,* 32:39-40(1988); Legacy Tobacco Document Library (Bates Document #523267826-523267833, Jul. 1, 1988, Memorandum on the Proposed Burley Tobacco Grade Index); and Miller et al., 1990, Tobacco Intern., 192:55-57 (all foregoing references are incorporated by inference in their entirety). In an aspect, a USDA grade index is a 0-100 numerical representation of federal grade received and is a weighted average of all stalk positions. A higher grade index indicates higher quality. Alternatively, leaf grade can be determined via hyper-spectral imaging. See e.g., WO 2011/027315 (published on Mar. 10, 2011, and incorporated by inference in its entirety). A comparable leaf grade index indicates a leaf grade index that does not vary more than 30% above or below an appropriate control or comparator when comparing leaves from similar stalk positions. In an aspect, a comparable leaf grade index does not vary more than 25%, 20%, 15%, 10%, 9%, 8%, 7%, 6%, 5%, 4%, 3%, 2%, or 1% above or below an appropriate control or comparator when comparing leaves from similar stalk positions.

In an aspect, tobacco plants provided herein comprise a similar level of one or more tobacco aroma compounds selected from the group consisting of 3-methylvaleric acid, valeric acid, isovaleric acid, a labdenoid, a cembrenoid, a sugar ester, and a reducing sugar, compared to control tobacco plants when grown in similar growth conditions. In another aspect, tobacco plants provided herein comprise a nic1 mutation, a nic2 mutation, or a combination thereof having no impact over the level of one or more tobacco aroma compounds selected from the group consisting of 3-methylvaleric acid, valeric acid, isovaleric acid, a labdenoid, a cembrenoid, a sugar ester, and a reducing sugar.

As used herein, tobacco aroma compounds are compounds associated with the flavor and aroma of tobacco smoke. These compounds include, but are not limited to, 3-methylvaleric acid, valeric acid, isovaleric acid, cembrenoid and labdenoid diterpenes, and sugar esters. Concentrations of tobacco aroma compounds can be measured by any known metabolite profiling methods in the art including, without limitation, gas chromatography mass spectrometry (GC-MS), Nuclear Magnetic Resonance Spectroscopy, liquid chromatography-linked mass spectrometry. See The Handbook of Plant Metabolomics, edited by Weckwerth and Kahl, (Wiley-Blackwell) (May 28, 2013).

As used herein, "reducing sugar(s)" are any sugar (monosaccharide or polysaccharide) that has a free or potentially free aldehdye or ketone group. Glucose and fructose act as nicotine buffers in cigarette smoke by reducing smoke pH and effectively reducing the amount of "free" unprotonated nicotine. Reducing sugars balances smoke flavor, for example, by modifying the sensory impact of nicotine and other tobacco alkaloids. An inverse relationship between sugar content and alkaloid content has been reported across tobacco varieties, within the same variety, and within the same plant line caused by planting conditions. Reducing sugar levels can be measured using a segmented-flow colorimetric method developed for analysis of tobacco samples as adapted by Skalar Instrument Co (West Chester, Pa.) and described by Davis, *Tobacco Science* 20:139-144 (1976). For example, a sample is dialyzed against a sodium carbonate solution. Copper neocuproin is added to the sample and the solution is heated. The copper neocuproin chelate is reduced in the presence of sugars resulting in a colored complex which is measured at 460 nm.

In an aspect, tobacco plants provided herein comprise one or more non-naturally existing mutant alleles at nic1 and/or nic2 locus which reduce or eliminate one or more gene activity from nic1 and/or nic2 locus. In an aspect, these mutant alleles result in lower nicotine levels. Mutant nic1 and/or nic2 alleles can be introduced by any method known in the art including random or targeted mutagenesis approaches.

Such mutagenesis methods include, without limitation, treatment of seeds with ethyl methylsulfate (EMS) (Hildering and Verkerk, In, The use of induced mutations in plant breeding. Pergamon press, pp 317-320, 1965) or UV-irradiation, X-rays, and fast neutron irradiation (see, for example, Verkerk, *Neth. J. Agric. Sci.* 19:197-203, 1971; and Poehlman, Breeding Field Crops, Van Nostrand Reinhold, New York (3.sup.rd ed), 1987), transposon tagging (Fedoroff et al., 1984; U.S. Pat. Nos. 4,732,856 and 5,013,658), as well as T-DNA insertion methodologies (Hoekema et al., 1983; U.S. Pat. No. 5,149,645). EMS-induced mutagenesis consists of chemically inducing random point mutations over the length of the genome. Fast neutron mutagenesis consists of exposing seeds to neutron bombardment which causes large deletions through double stranded DNA breakage. Transposon tagging comprises inserting a transposon within an endogenous gene to reduce or eliminate expression of the gene. The types of mutations that may be present in a tobacco gene include, for example, point mutations, deletions, insertions, duplications, and inversions. Such mutations desirably are present in the coding region of a tobacco gene; however mutations in the promoter region, and intron, or an untranslated region of a tobacco gene may also be desirable.

In addition, a fast and automatable method for screening for chemically induced mutations, TILLING (Targeting Induced Local Lesions In Genomes), using denaturing HPLC or selective endonuclease digestion of selected PCR products is also applicable to the present disclosure. See, McCallum et al. (2000) *Nat. Biotechnol.* 18:455-457. Mutations that impact gene expression or that interfere with the function of genes can be determined using methods that are well known in the art. Insertional mutations in gene exons usually result in null-mutants. Mutations in conserved residues can be particularly effective in inhibiting the function of a protein. In an aspect, tobacco plants comprise a nonsense (e.g., stop codon) mutation in one or more NCG genes described in U.S. Provisional Application Nos. 62/616,959 and 62/625,878, both of which are incorporated by reference in their entirety.

In an aspect, the present disclosure also provides tobacco lines with altered nicotine levels while maintaining commercially acceptable leaf quality. These lines can be produced by introducing mutations into one or more genes at nic1 and/or nic2 locus via precise genome engineering technologies, for example, Transcription activator-like effector nucleases (TALENs), meganuclease, zinc finger nuclease, and a clustered regularly-interspaced short palindromic repeats (CRISPR)/Cas9 system, a CRISPR/Cpf1 system, a CRISPR/Csm1 system, and a combination thereof (see, for example, U.S. Patent Application publication 2017/0233756). See, e.g., Gaj et al., *Trends in Biotechnology,* 31(7):397-405 (2013).

The screening and selection of mutagenized tobacco plants can be through any methodologies known to those having ordinary skill in the art. Examples of screening and selection methodologies include, but are not limited to, Southern analysis, PCR amplification for detection of a polynucleotide, Northern blots, RNase protection, primer-extension, RT-PCR amplification for detecting RNA transcripts, Sanger sequencing, Next Generation sequencing technologies (e.g., Illumina, PacBio, Ion Torrent, 454), enzymatic assays for detecting enzyme or ribozyme activity of polypeptides and polynucleotides, and protein gel electrophoresis, Western blots, immunoprecipitation, and enzyme-linked immunoassays to detect polypeptides. Other techniques such as in situ hybridization, enzyme staining, and immunostaining also can be used to detect the presence or expression of polypeptides and/or polynucleotides. Methods for performing all of the referenced techniques are known.

In an aspect, a tobacco plant or plant genome provided herein is mutated or edited by a nuclease selected from the group consisting of a meganuclease, a zinc-finger nuclease (ZFN), a transcription activator-like effector nuclease (TALEN), a CRISPR/Cas9 nuclease, a CRISPR/Cpf1 nuclease, or a CRISPR/Csm1 nuclease.

In an aspect, tobacco plants provided herein comprising a nic1 mutation, a nic2 mutation, or both, further comprises a transgene or mutation providing an early-senescence trait. In one aspect, a mutation providing an early-senescence trait is yellow burley1 (−yb1). In an aspect, a mutation providing an early-senescence trait is yellow burley2 (−yb2). In one aspect, a mutation providing an early-senescence trait is pale yellow (PY).

In an aspect, a tobacco plant, or part thereof, comprises relative to a control tobacco plant: a first genome modification providing a lower level of nicotine or total alkaloid, and a second genome modification providing a comparable level of one or more traits selected from the group consisting of total leaf polyamine level, total root polyamine level, total leaf chlorophyll level, mesophyll cell number per leaf area unit, and leaf epidermal cell size; and where the control plant does not have both the first and the second genome modifications. In one aspect, a tobacco plant, or part thereof, comprises relative to a control tobacco plant: a first genome modification providing a lower level of nicotine or total alkaloid, and a second genome modification providing a comparable level of total leaf polyamine level, where the control plant does not have both the first and the second genome modifications. In an aspect, a tobacco plant, or part thereof, comprises relative to a control tobacco plant: a first genome modification providing a lower level of nicotine or total alkaloid, and a second genome modification providing a comparable level of total root polyamine level, where the control plant does not have both the first and the second genome modifications. In one aspect, a tobacco plant, or part thereof, comprises relative to a control tobacco plant: a first genome modification providing a lower level of nicotine or total alkaloid, and a second genome modification providing a comparable level of total leaf chlorophyll level, where the control plant does not have both the first and the second genome modifications. In an aspect, a tobacco plant, or part thereof, comprises relative to a control tobacco plant: a first genome modification providing a lower level of nicotine or total alkaloid, and a second genome modification providing a comparable level of mesophyll cell number per leaf area unit, where the control plant does not have both the first and the second genome modifications. In one aspect, a tobacco plant, or part thereof, comprises relative to a control tobacco plant: a first genome modification providing a lower level of nicotine or total alkaloid, and a second genome modification providing a comparable level of leaf epidermal cell size, where the control plant does not have both the first and the second genome modifications.

In an aspect, a first genome modification, a second genome modification, or both comprise a transgene, a mutation, or both. In one aspect, a genome modification, a second genome modification, or both comprise a transgene. In an aspect, a first genome modification, a second genome modification, or both comprise a mutation. In one aspect, a first genome modification, a second genome modification, or both are not transgene-based. In an aspect, a first genome modification, a second genome modification, or both are not mutation-based.

In an aspect, tobacco plants provided herein comprise a first genome modification providing a lower level of nicotine compared to a control tobacco plant. In one aspect, tobacco plants provided herein comprise a first genome modification comprising a nic1 mutation, a nic2 mutation, or both. In an aspect, tobacco plants provided herein comprise a transgene targeting the Nic1 locus, a transgene targeting the Nic2 locus, or both.

In an aspect, tobacco plants provided herein comprise a first genome modification comprising a mutation in a gene or locus encoding a protein selected from the group consisting of aspartate oxidase, agmatine deiminase (AIC), arginase, diamine oxidase, arginine decarboxylase (ADC), methylputrescine oxidase (MPO), NADH dehydrogenase, ornithine decarboxylase (ODC), phosphoribosylanthranilate isomerase (PRAI), putrescine N-methyltransferase (PMT), quinolate phosphoribosyl transferase (QPT), and S-adenosyl-methionine synthetase (SAMS), A622, NBB1, BBL, MYC2, Nic1, Nic2, ethylene response factor (ERF) transcription factor, nicotine uptake permease (NUP), and MATE transporter. In one aspect, tobacco plants provided herein comprise a first genome modification comprises a transgene targeting and suppressing a gene or locus encoding a protein selected from the group consisting of aspartate oxidase, agmatine deiminase (AIC), arginase, diamine oxidase, arginine decarboxylase (ADC), methylputrescine oxidase (MPO), NADH dehydrogenase, ornithine decarboxylase (ODC), phosphoribosylanthranilate isomerase (PRAI), putrescine N-methyltransferase (PMT), quinolate phosphoribosyl transferase (QPT), and S-adenosyl-methionine synthetase (SAMS), A622, NBB1, BBL, MYC2, Nic1, Nic2, ethylene response factor (ERF) transcription factor, nicotine uptake permease (NUP), and MATE transporter.

In an aspect, tobacco plants provided herein comprise a first genome modification comprising a mutation in a gene or locus encoding a protein selected from the group consisting of ERF32, ERF34, ERF39, ERF189, ERF115, ERF221, ERF104, ERF179, ERF17, and ERF168. In one aspect, tobacco plants provided herein comprise a first genome modification comprises a transgene targeting and suppressing a gene or locus encoding a protein selected from the group consisting of ERF32, ERF34, ERF39, ERF189, ERF115, ERF221, ERF104, ERF179, ERF17, and ERF168.

In an aspect, a tobacco plant or plant genome provided is mutated or edited to have one or more mutations in one or more NCG genes selected from the group consisting of NCG1 to NCG35, where the one or more mutations reduce or eliminate the activity or expression of the one or more NCG genes. In an aspect, a tobacco plant or plant genome provided is mutated or edited to have one or more mutations in one or more NCG genes selected from the group consisting of NCG1, NCG2, NCG11, NCG12, NCG13, NCG15, NCG16, NCG17, NCG21, NCG22, NCG24, NCG26, NCG29, NCG30, and NCG35, where the one or more mutations reduce or eliminate the activity or expression of the one or more NCG genes. In an aspect, a tobacco plant or plant genome provided is mutated or edited to have one or more mutations in one or more NCG genes selected from the group consisting of NCG1 to NCG21, where the one or more mutations reduce or eliminate the activity or expression of the one or more NCG genes. In an aspect, a tobacco plant or plant genome provided is mutated or edited to have one or more mutations in one or more NCG genes selected from the group consisting of NCG1, NCG2, NCG11, NCG12, NCG15, NCG16, and NCG17, where the one or more mutations reduce or eliminate the activity or expression of the one or more NCG genes. In an aspect, a tobacco plant or plant genome provided is mutated or edited to have one or more mutations in one or more NCG genes selected from the group consisting of NCG2, NCG12, NCG15, NCG16, and NCG17, where the one or more mutations reduce or eliminate the activity or expression of the one or more NCG genes. In an aspect, a tobacco plant or plant genome provided is mutated or edited to have one or more mutations in one or more NCG genes selected from the group consisting of NCG12, NCG15, NCG16, and NCG17, where the one or more mutations reduce or eliminate the activity or expression of the one or more NCG genes. In another aspect, an edited or mutated tobacco plant having one or more, two or more, three or more, four or more, or five or more NCG mutations further comprises one or more mutations in one or more, two or more, three or more, four or more, or five or more ERF genes selected from the group consisting of ERF189, ERF115, ERF221, ERF104, ERF179, ERF17, and ERF168, where the one or more mutations reduce or eliminate the activity or expression of the one or more ERF genes.

In an aspect, a tobacco plant or plant genome provided is mutated or edited to have two or more mutations in two or more NCG genes selected from the group consisting of NCG1 to NCG35, where the two or more mutations reduce or eliminate the activity or expression of the two or more NCG genes. In an aspect, a tobacco plant or plant genome provided is mutated or edited to have two or more mutations in two or more NCG genes selected from the group consisting of NCG1, NCG2, NCG11, NCG12, NCG13, NCG15, NCG16, NCG17, NCG21, NCG22, NCG24, NCG26, NCG29, NCG30, and NCG35, where the two or more mutations reduce or eliminate the activity or expression of the two or more NCG genes. In an aspect, a tobacco plant or plant genome provided is mutated or edited to have two or more mutations in two or more NCG genes selected from the group consisting of NCG1 to NCG21, where the two or more mutations reduce or eliminate the activity or expression of the one or more NCG genes. In an aspect, a tobacco plant or plant genome provided is mutated or edited to have two or more mutations in two or more NCG genes selected from the group consisting of NCG1, NCG2, NCG11, NCG12, NCG15, NCG16, and NCG17, where the two or more mutations reduce or eliminate the activity or expression of the one or more NCG genes. In an aspect, a tobacco plant or plant genome provided is mutated or edited to have two or more mutations in two or more NCG genes selected from the group consisting of NCG2, NCG12, NCG15, NCG16, and NCG17, where the two or more mutations reduce or eliminate the activity or expression of the two or more NCG genes. In an aspect, a tobacco plant or plant genome provided is mutated or edited to have two or more mutations in two or more NCG genes selected from the group consisting of NCG12, NCG15, NCG16, and NCG17, where the two or more mutations reduce or eliminate the activity or expression of the two or more NCG genes. In another aspect, an edited or mutated tobacco plant having two or more NCG mutations further comprises two or more mutations in two or more ERF genes selected from the group consisting of ERF189, ERF115, ERF221, ERF104, ERF179, ERF17, and ERF168, where the two or more mutations reduce or eliminate the activity or expression of the two or more ERF genes.

In an aspect, a tobacco plant or plant genome provided is mutated or edited to have three or more mutations in three or more NCG genes selected from the group consisting of NCG1 to NCG35, where the three or more mutations reduce or eliminate the activity or expression of the three or more NCG genes. In an aspect, a tobacco plant or plant genome provided is mutated or edited to have three or more mutations in three or more NCG genes selected from the group consisting of NCG1, NCG2, NCG11, NCG12, NCG13, NCG15, NCG16, NCG17, NCG21, NCG22, NCG24, NCG26, NCG29, NCG30, and NCG35, where the three or more mutations reduce or eliminate the activity or expression of the three or more NCG genes. In an aspect, a tobacco plant or plant genome provided is mutated or edited to have three or more mutations in three or more NCG genes selected from the group consisting of NCG1 to NCG21, where the three or more mutations reduce or eliminate the activity or expression of the three or more NCG genes. In an aspect, a tobacco plant or plant genome provided is mutated or edited to have three or more mutations in three or more NCG genes selected from the group consisting of NCG1, NCG2, NCG11, NCG12, NCG15, NCG16, and NCG17, where the three or more mutations reduce or eliminate the activity or expression of the three or more NCG genes. In an aspect, a tobacco plant or plant genome provided is mutated or edited to have three or more mutations in three or more NCG genes selected from the group consisting of NCG2, NCG12, NCG15, NCG16, and NCG17, where the three or more mutations reduce or eliminate the activity or expression of the three or more NCG genes. In an aspect, a tobacco plant or plant genome provided is mutated or edited to have three or more mutations in three or more NCG genes selected from the group consisting of NCG12, NCG15, NCG16, and NCG17, where the three or more mutations reduce or eliminate the activity or expression of the three or more NCG genes. In another aspect, an edited or mutated tobacco plant having three or more NCG mutations further comprises three or more mutations in three or more ERF genes selected from the group consisting of ERF189, ERF115, ERF221, ERF104, ERF179, ERF17, and ERF168, where the three or more mutations reduce or eliminate the activity or expression of the three or more ERF genes.

In an aspect, a tobacco plant or plant genome provided is mutated or edited to have four or more mutations in four or more NCG genes selected from the group consisting of NCG1 to NCG35, where the four or more mutations reduce or eliminate the activity or expression of the four or more NCG genes. In an aspect, a tobacco plant or plant genome provided is mutated or edited to have four or more mutations in four or more NCG genes selected from the group consisting of NCG1, NCG2, NCG11, NCG12, NCG13, NCG15, NCG16, NCG17, NCG21, NCG22, NCG24, NCG26, NCG29, NCG30, and NCG35, where the four or more mutations reduce or eliminate the activity or expression of the four or more NCG genes. In an aspect, a tobacco plant or plant genome provided is mutated or edited to have four or more mutations in four or more NCG genes selected from the group consisting of NCG1 to NCG21, where the four or more mutations reduce or eliminate the activity or expression of the four or more NCG genes. In an aspect, a tobacco plant or plant genome provided is mutated or edited to have four or more mutations in four or more NCG genes selected from the group consisting of NCG1, NCG2, NCG11, NCG12, NCG15, NCG16, and NCG17, where the four or more mutations reduce or eliminate the activity or expression of the four or more NCG genes. In an aspect, a tobacco plant or plant genome provided is mutated or edited to have four or more mutations in four or more NCG genes selected from the group consisting of NCG2, NCG12, NCG15, NCG16, and NCG17, where the four or more mutations reduce or eliminate the activity or expression of the four or more NCG genes. In an aspect, a tobacco plant or plant genome provided is mutated or edited to have four or more mutations in four or more NCG genes selected from the group consisting of NCG12, NCG15, NCG16, and NCG17, where the four or more mutations reduce or eliminate the activity or expression of the four or more NCG genes. In another aspect, an edited or mutated tobacco plant having four or more NCG mutations further comprises four or more mutations in four or more ERF genes selected from the group consisting of ERF189, ERF115, ERF221, ERF104, ERF179, ERF17, and ERF168, where the four or more mutations reduce or eliminate the activity or expression of the four or more ERF genes.

In an aspect, a tobacco plant or plant genome provided comprises one or more transgenes targeting one or more NCG genes selected from the group consisting of NCG1 to NCG3S, where the one or more transgenes reduce or eliminate the activity or expression of the one or more NCG genes. In an aspect, a tobacco plant or plant genome provided comprises one or more transgenes targeting one or more NCG genes selected from the group consisting of NCG1, NCG2, NCG11, NCG12, NCG13, NCG15, NCG16, NCG17, NCG21, NCG22, NCG24, NCG26, NCG29, NCG30, and NCG3S, where the one or more transgenes reduce or eliminate the activity or expression of the one or more NCG genes. In an aspect, a tobacco plant or plant genome provided comprises one or more transgenes targeting one or more NCG genes selected from the group consisting of NCG1 to NCG21, where the one or more transgenes reduce or eliminate the activity or expression of the one or more NCG genes. In an aspect, a tobacco plant or plant genome provided comprises one or more transgenes targeting one or more NCG genes selected from the group consisting of NCG1, NCG2, NCG11, NCG12, NCG15, NCG16, and NCG17, where the one or more transgenes reduce or eliminate the activity or expression of the one or more NCG genes. In an aspect, a tobacco plant or plant genome provided comprises one or more transgenes targeting one or more NCG genes selected from the group consisting of NCG2, NCG12, NCG15, NCG16, and NCG17, where the one or more transgenes reduce or eliminate the activity or expression of the one or more NCG genes. In an aspect, a tobacco plant or plant genome provided comprises one or more transgenes targeting one or more NCG genes selected from the group consisting of NCG12, NCG15, NCG16, and NCG17, where the one or more transgenes reduce or eliminate the activity or expression of the one or more NCG genes. In another aspect, a tobacco plant having one or more, two or more, three or more, four or more, or five or more NCG-targeting transgenes further comprises one or more mutations in one or more, two or more, three or more, four or more, or five or more ERF genes selected from the group consisting of ERF189, ERF115, ERF221, ERF104, ERF179, ERF17, and ERF168, where the one or more mutations reduce or eliminate the activity or expression of the one or more ERF genes. In another aspect, a tobacco plant having one or more, two or more, three or more, four or more, or five or more NCG-targeting transgenes further comprises one or more transgenes targeting one or more, two or more, three or more, four or more, or five or more ERF genes selected from the group consisting of ERF189, ERF115, ERF221, ERF104, ERF179, ERF17, and ERF168, where the one or more ERF-targeting transgenes reduce or eliminate the activity or expression of the one or more ERF genes.

In an aspect, a tobacco plant or plant genome provided comprises two or more transgenes targeting two or more NCG genes selected from the group consisting of NCG1 to NCG35, where the two or more transgenes reduce or eliminate the activity or expression of the two or more NCG genes. In an aspect, a tobacco plant or plant genome provided comprises two or more transgenes targeting two or more NCG genes selected from the group consisting of NCG1, NCG2, NCG11, NCG12, NCG13, NCG15, NCG16, NCG17, NCG21, NCG22, NCG24, NCG26, NCG29, NCG30, and NCG35, where the two or more transgenes reduce or eliminate the activity or expression of the two or more NCG genes. In an aspect, a tobacco plant or plant genome provided comprises two or more transgenes targeting two or more NCG genes selected from the group consisting of NCG1 to NCG21, where the two or more transgenes reduce or eliminate the activity or expression of the one or more NCG genes. In an aspect, a tobacco plant or plant genome provided comprises two or more transgenes targeting two or more NCG genes selected from the group consisting of NCG1, NCG2, NCG11, NCG12, NCG15, NCG16, and NCG17, where the two or more transgenes reduce or eliminate the activity or expression of the one or more NCG genes. In an aspect, a tobacco plant or plant genome provided comprises two or more transgenes targeting two or more NCG genes selected from the group consisting of NCG2, NCG12, NCG15, NCG16, and NCG17, where the two or more transgenes reduce or eliminate the activity or expression of the two or more NCG genes. In an aspect, a tobacco plant or plant genome provided comprises two or more transgenes targeting two or more NCG genes selected from the group consisting of NCG12, NCG15, NCG16, and NCG17, where the two or more transgenes reduce or eliminate the activity or expression of the two or more NCG genes. In another aspect, a tobacco plant having two or more NCG-targeting transgenes further comprises two or more mutations in two or more ERF genes selected from the group consisting of ERF189, ERF115, ERF221, ERF104, ERF179, ERF17, and ERF168, where the two or more mutations reduce or eliminate the activity or expression of the two or more ERF genes. In another aspect, a tobacco plant having two or more NCG-targeting transgenes further comprises two or more transgenes targeting two or more ERF genes selected from the group consisting of ERF189, ERF115, ERF221, ERF104, ERF179, ERF17, and ERF168, where the two or more ERF-targeting transgenes reduce or eliminate the activity or expression of the two or more ERF genes.

In an aspect, a tobacco plant or plant genome provided comprises three or more transgenes targeting three or more NCG genes selected from the group consisting of NCG1 to NCG35, where the three or more transgenes reduce or eliminate the activity or expression of the three or more NCG genes. In an aspect, a tobacco plant or plant genome provided comprises three or more transgenes targeting three or more NCG genes selected from the group consisting of NCG1, NCG2, NCG11, NCG12, NCG13, NCG15, NCG16, NCG17, NCG21, NCG22, NCG24, NCG26, NCG29, NCG30, and NCG35, where the three or more transgenes reduce or eliminate the activity or expression of the three or more NCG genes. In an aspect, a tobacco plant or plant genome provided comprises three or more transgenes targeting three or more NCG genes selected from the group consisting of NCG1 to NCG21, where the three or more transgenes reduce or eliminate the activity or expression of the three or more NCG genes. In an aspect, a tobacco plant or plant genome provided comprises three or more transgenes targeting three or more NCG genes selected from the group consisting of NCG1, NCG2, NCG11, NCG12, NCG15, NCG16, and NCG17, where the three or more transgenes reduce or eliminate the activity or expression of the three or more NCG genes. In an aspect, a tobacco plant or plant genome provided comprises three or more transgenes targeting three or more NCG genes selected from the group consisting of NCG2, NCG12, NCG15, NCG16, and NCG17, where the three or more transgenes reduce or eliminate the activity or expression of the three or more NCG genes. In an aspect, a tobacco plant or plant genome provided comprises three or more transgenes targeting three or more NCG genes selected from the group consisting of NCG12, NCG15, NCG16, and NCG17, where the three or more transgenes reduce or eliminate the activity or expression of the three or more NCG genes. In another aspect, a tobacco plant having three or more NCG-targeting transgenes further comprises three or more mutations in three or more ERF genes selected from the group consisting of ERF189, ERF115, ERF221, ERF104, ERF179, ERF17, and ERF168, where the three or more mutations reduce or eliminate the activity or expression of the three or more ERF genes. In another aspect, a tobacco plant having three or more NCG-targeting transgenes further comprises three or more transgenes targeting three or more ERF genes selected from the group consisting of ERF189, ERF115, ERF221, ERF104, ERF179, ERF17, and ERF168, where the three or more ERF-targeting transgenes reduce or eliminate the activity or expression of the three or more ERF genes.

In an aspect, a tobacco plant or plant genome provided comprises four or more transgenes targeting four or more NCG genes selected from the group consisting of NCG1 to NCG35, where the four or more transgenes reduce or eliminate the activity or expression of the four or more NCG genes. In an aspect, a tobacco plant or plant genome provided comprises four or more transgenes targeting four or more NCG genes selected from the group consisting of NCG1, NCG2, NCG11, NCG12, NCG13, NCG15, NCG16, NCG17, NCG21, NCG22, NCG24, NCG26, NCG29, NCG30, and NCG35, where the four or more transgenes reduce or eliminate the activity or expression of the four or more NCG genes. In an aspect, a tobacco plant or plant genome provided comprises four or more transgenes targeting four or more NCG genes selected from the group consisting of NCG1 to NCG21, where the four or more transgenes reduce or eliminate the activity or expression of the four or more NCG genes. In an aspect, a tobacco plant or plant genome provided comprises four or more transgenes targeting four or more NCG genes selected from the group consisting of NCG1, NCG2, NCG11, NCG12, NCG15, NCG16, and NCG17, where the four or more transgenes reduce or eliminate the activity or expression of the four or more NCG genes. In an aspect, a tobacco plant or plant genome provided comprises four or more transgenes targeting four or more NCG genes selected from the group consisting of NCG2, NCG12, NCG15, NCG16, and NCG17, where the four or more transgenes reduce or eliminate the activity or expression of the four or more NCG genes. In an aspect, a tobacco plant or plant genome provided comprises four or more transgenes targeting four or more NCG genes selected from the group consisting of NCG12, NCG15, NCG16, and NCG17, where the four or more transgenes reduce or eliminate the activity or expression of the four or more NCG genes. In another aspect, a tobacco plant having four or more NCG-targeting transgenes further comprises four or more mutations in four or more ERF genes selected from the group consisting of ERF189, ERF115, ERF221, ERF104, ERF179, ERF17, and ERF168, where the four or more mutations reduce or eliminate the activity or expression of the four or more ERF genes. In another aspect, a tobacco plant having four or more NCG-targeting transgenes further comprises four or more transgenes targeting four or more ERF genes selected from the group consisting of ERF189, ERF115, ERF221, ERF104, ERF179, ERF17, and ERF168, where the four or more ERF-targeting transgenes reduce or eliminate the activity or expression of the four or more ERF genes.

In an aspect, tobacco plants provided herein comprise second genome modification comprising an inducible promoter operably linked to a transcribable DNA sequence encoding a non-coding RNA for suppression of an ornithine decarboxylase (ODC) gene. In another aspect, a tobacco plant is provided having suppressed MYB8 activity via either transgene suppression, mutagenesis, or targeted genome editing. For simplicity, every instance here mentioning ODC suppression (e.g., operably linked to any particular type of promoters) is equally applicable to MYB8 suppression.

In an aspect, tobacco plants provided herein comprise a reduced amount of total conjugated polyamines in leaves relative to the control tobacco plant. In one aspect, tobacco plants provided herein comprise a reduced amount of total conjugated polyamines in roots relative to the control tobacco plant. Used here, conjugated polyamines include, but are not limited to, soluble conjugated polyamines such as phenolamides containing a backbone consisting of a free polyamine (e.g., putrescine, spermine, and/or spermidine) conjugated with one or more phenylpropanoids such as ferulic, caffeic and courmaric acids. Conjugated polyamines also include, but are not limited to, insoluble conjugated polyamines incorporated into structural polymers such as lignin. In an aspect, tobacco plants provided herein comprise a reduced amount of total free polyamines (e.g., putrescine, spermine, and spermidine) in leaves relative to the control tobacco plant. In one aspect, tobacco plants provided herein comprise a reduced amount of total conjugated polyamines in roots relative to the control tobacco plant. In an aspect, tobacco plants provided herein comprise a reduced amount of total conjugated form of one or more polyamines selected from the group consisting of putrescine, spermidine and spermine in leaves relative to the control tobacco plant. In one aspect, tobacco plants provided herein comprise a reduced amount of total conjugated form of one or more polyamines selected from the group consisting of putrescine, spermidine and spermine in roots relative to the control tobacco plant. In an aspect, tobacco plants provided herein comprise a reduced amount of total free form of one or more polyamines selected from the group consisting of putrescine, spermidine and spermine in leaves relative to the control tobacco plant. In one aspect, tobacco plants provided herein comprise a reduced amount of total conjugated form of one or more polyamines selected from the group consisting of putrescine, spermidine and spermine in roots relative to the control tobacco plant.

In an aspect, a characteristic or a trait of a tobacco plant described here are measured at a time selected from the group consisting of immediately before flowering, at topping, 1 week-post-topping (WPT), 2 WPT, 3 WPT, 4 WPT, 5 WPT, 6 WPT, 7 WPT, 8 WPT, and at harvest. In one aspect, tobacco plants provided herein comprising a first and a second genome modification are capable of producing a leaf with a leaf grade comparable to that of a leaf from a control plant. In an aspect, tobacco plants provided herein comprising a first and a second genome modification have a total leaf yield comparable to a control plant.

As used herein, "editing" or "genome editing" refers to targeted mutagenesis of at least 1, at least 2, at least 3, at least 4, at least 5, at least 6, at least 7, at least 8, at least 9, or at least 10 nucleotides of an endogenous plant genome nucleic acid sequence, or removal or replacement of an endogenous plant genome nucleic acid sequence. In an aspect, an edited nucleic acid sequence provided has at least 99.9%, at least 99.5%, at least 99%, at least 98%, at least 97%, at least 96%, at least 95%, at least 94%, at least 93%, at least 92%, at least 91%, at least 90%, at least 85%, at least 80%, or at least 75% sequence identity with an endogenous nucleic acid sequence. In an aspect, an edited nucleic acid sequence provided has at least 99.9%, at least 99.5%, at least 99%, at least 98%, at least 97%, at least 96%, at least 95%, at least 94%, at least 93%, at least 92%, at least 91%, at least 90%, at least 85%, at least 80%, or at least 75% sequence identity with SEQ ID Nos: 23-28, and fragments thereof. In another aspect, an edited nucleic acid sequence provided has at least 99.9%, at least 99.5%, at least 99%, at least 98%, at least 97%, at least 96%, at least 95%, at least 94%, at least 93%, at least 92%, at least 91%, at least 90%, at least 85%, at least 80%, or at least 75% sequence identity with a polynucleotide encoding a polypeptide selected from the group consisting of SEQ ID NOs:29-34.

Meganucleases, ZFNs, TALENs, CRISPR/Cas9, CRISPR/Csm1 and CRISPR/Cpf1 induce a double-strand DNA break at a target site of a genomic sequence that is then repaired by the natural processes of homologous recombination (HR) or non-homologous end-joining (NHEJ). Sequence modifications then occur at the cleaved sites, which can include deletions or insertions that result in gene disruption in the case of NHEJ, or integration of donor nucleic acid sequences by HR. In an aspect, a method provided comprises editing a plant genome with a nuclease provided to mutate at least 1, at least 2, at least 3, at least 4, at least 5, at least 6, at least 7, at least 8, at least 9, at least 10, or more than 10 nucleotides in the plant genome via HR with a donor polynucleotide. In an aspect, a mutation provided is caused by genome editing using a nuclease. In another aspect, a mutation provided is caused by non-homologous end-joining or homologous recombination.

In an aspect, a mutation provided here provides a dominant mutant that activates the expression or activity of a gene of interest, e.g., a gene selected from the group consisting of a biosynthetic enzyme, a regulatory transcription factor, a transporter, a catabolic enzyme, or a combination thereof, for one or more antioxidants.

Meganucleases, which are commonly identified in microbes, are unique enzymes with high activity and long recognition sequences (>14 bp) resulting in site-specific digestion of target DNA. Engineered versions of naturally occurring meganucleases typically have extended DNA recognition sequences (for example, 14 to 40 bp). The engineering of meganucleases can be more challenging than that of ZFNs and TALENs because the DNA recognition and cleavage functions of meganucleases are intertwined in a single domain. Specialized methods of mutagenesis and high-throughput screening have been used to create novel meganuclease variants that recognize unique sequences and possess improved nuclease activity.

ZFNs are synthetic proteins consisting of an engineered zinc finger DNA-binding domain fused to the cleavage domain of the FokI restriction endonuclease. ZFNs can be designed to cleave almost any long stretch of double-stranded DNA for modification of the zinc finger DNA-binding domain. ZFNs form dimers from monomers composed of a non-specific DNA cleavage domain of FokI endonuclease fused to a zinc finger array engineered to bind a target DNA sequence.

The DNA-binding domain of a ZFN is typically composed of 3-4 zinc-finger arrays. The amino acids at positions −1, +2, +3, and +6 relative to the start of the zinc finger Go-helix, which contribute to site-specific binding to the target DNA, can be changed and customized to fit specific target sequences. The other amino acids form the consensus backbone to generate ZFNs with different sequence specificities. Rules for selecting target sequences for ZFNs are known in the art.

The FokI nuclease domain requires dimerization to cleave DNA and therefore two ZFNs with their C-terminal regions are needed to bind opposite DNA strands of the cleavage site (separated by 5-7 bp). The ZFN monomer can cute the target site if the two-ZF-binding sites are palindromic. The term ZFN, as used herein, is broad and includes a monomeric ZFN that can cleave double stranded DNA without assistance from another ZFN. The term ZFN is also used to refer to one or both members of a pair of ZFNs that are engineered to work together to cleave DNA at the same site.

Without being limited by any scientific theory, because the DNA-binding specificities of zinc finger domains can in principle be re-engineered using one of various methods, customized ZFNs can theoretically be constructed to target nearly any gene sequence. Publicly available methods for engineering zinc finger domains include Context-dependent Assembly (CoDA), Oligomerized Pool Engineering (OPEN), and Modular Assembly.

TALENs are artificial restriction enzymes generated by fusing the transcription activator-like effector (TALE) DNA binding domain to a FokI nuclease domain. When each member of a TALEN pair binds to the DNA sites flanking a target site, the FokI monomers dimerize and cause a double-stranded DNA break at the target site. The term TALEN, as used herein, is broad and includes a monomeric TALEN that can cleave double stranded DNA without assistance from another TALEN. The term TALEN is also used to refer to one or both members of a pair of TALENs that work together to cleave DNA at the same site.

Transcription activator-like effectors (TALEs) can be engineered to bind practically any DNA sequence. TALE proteins are DNA-binding domains derived from various plant bacterial pathogens of the genus *Xanthomonas*. The *Xanthomonas* pathogens secrete TALEs into the host plant cell during infection. The TALE moves to the nucleus, where it recognizes and binds to a specific DNA sequence in the promoter region of a specific DNA sequence in the promoter region of a specific gene in the host genome. TALE has a central DNA-binding domain composed of 13-28 repeat monomers of 33-34 amino acids. The amino acids of each monomer are highly conserved, except for hypervariable amino acid residues at positions 12 and 13. The two variable amino acids are called repeat-variable diresidues (RVDs). The amino acid pairs NI, NG, HD, and NN of RVDs preferentially recognize adenine, thymine, cytosine, and guanine/adenine, respectively, and modulation of RVDs can recognize consecutive DNA bases. This simple relationship between amino acid sequence and DNA recognition has allowed for the engineering of specific DNA binding domains by selecting a combination of repeat segments containing the appropriate RVDs.

Besides the wild-type FokI cleavage domain, variants of the FokI cleavage domain with mutations have been designed to improve cleavage specificity and cleavage activity. The FokI domain functions as a dimer, requiring two constructs with unique DNA binding domains for sites in the target genome with proper orientation and spacing. Both the number of amino acid residues between the TALEN DNA binding domain and the FokI cleavage domain and the number of bases between the two individual TALEN binding sites are parameters for achieving high levels of activity.

A relationship between amino acid sequence and DNA recognition of the TALE binding domain allows for designable proteins. Software programs such as DNA Works can be used to design TALE constructs. Other methods of designing TALE constructs are known to those of skill in the art. See Doyle et al., Nucleic Acids Research (2012) 40: W117-122; Cermak et al., Nucleic Acids Research (2011). 39:e82; and tale-nt.cac.cornell.edu/about.

A CRISPR/Cas9 system, CRISPR/Csm1, or a CRISPR/Cpf1 system are alternatives to the FokI-based methods ZFN and TALEN. The CRISPR systems are based on RNA-guided engineered nucleases that use complementary base pairing to recognize DNA sequences at target sites.

CRISPR/Cas9, CRISPR/Csm1, and a CRISPR/Cpf1 systems are part of the adaptive immune system of bacteria and archaea, protecting them against invading nucleic acids such as viruses by cleaving the foreign DNA in a sequence-dependent manner. The immunity is acquired by the integration of short fragments of the invading DNA known as spacers between two adjacent repeats at the proximal end of a CRISPR locus. The CRISPR arrays, including the spacers, are transcribed during subsequent encounters with invasive DNA and are processed into small interfering CRISPR RNAs (crRNAs) approximately 40 nt in length, which combine with the trans-activating CRISPR RNA (tracrRNA) to activate and guide the Cas9 nuclease. This cleaves homologous double-stranded DNA sequences known as protospacers in the invading DNA. A prerequisite for cleavage is the presence of a conserved protospacer-adjacent motif (PAM) downstream of the target DNA, which usually has the sequence 5-NGG-3 but less frequently NAG. Specificity is provided by the so-called "seed sequence" approximately 12 bases upstream of the PAM, which must match between the RNA and target DNA. Cpf1 and Csm1 act in a similar manner to Cas9, but Cpf1 and Csm1 do not require a tracrRNA.

In still another aspect, a tobacco plant provided further comprises one or more mutations in one or more loci encoding a nicotine demethylase (e.g., CYP82E4, CYP82E5, CYP82E10) that confer reduced amounts of nornicotine (See U.S. Pat. Nos. 8,319,011; 8,124,851; 9,187,759; 9,228,194; 9,228,195; 9,247,706) compared to control plant lacking one or more mutations in one or more loci encoding a nicotine demethylase. In an aspect, a modified tobacco plant described further comprises reduced nicotine demethylase activity compared to a control plant when grown and cured under comparable conditions. In a further aspect, a tobacco plant provided further comprises one or more mutations or transgenes providing an elevated level of one or more antioxidants (See U.S. patent application Ser. No. 15/727,523 and PCT Application No. PCT/US2017/055618). In another aspect, a tobacco plant provided further comprises one or more mutations or transgenes providing a reduced level of one or more TSNAs (such as N'-nitrosonornicotine (NNN), 4-methylnitrosoamino-1-(3-pyridyl)-1-butanone (NNK), N'-nitrosoanatabine (NAT) N'-nitrosoanabasine (NAB)).

The present disclosure also provides compositions and methods for inhibiting the expression or function of one or more genes involved in polyamine biosynthesis or regulation thereof, in a plant, particularly plants of the *Nicotiana* genus, including tobacco plants of the various commercial varieties.

In an aspect, the present disclosure provides tobacco plants, or part thereof, comprising a heterologous expression cassette comprising an ODC inhibitory sequence. In another aspect, tobacco plants, or part thereof, comprise a heterologous expression cassette comprising an inhibitory sequence of a gene comprising a sequence having at least 80%, at least 85%, at least 90%, at least 95%, at least 97%, at least 98%, at least 99%, or 100% identity to a sequence selected from the group consisting of SEQ ID NOs: 23-28, and fragments thereof, where the inhibitory sequence is operably linked to a promoter that is functional in a plant cell, and where the inhibitory sequence has at least 90% sequence identity to a fragment of at least 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, or 80 nucleotides of the sequence having at least 80%, at least 85%, at least 90%, at least 95%, at least 97%, at least 98%, at least 99%, or 100% identity to a sequence selected from the group consisting of SEQ ID NOs: 23-28, and fragments thereof.

As used herein, the terms "inhibit," "inhibition," and "inhibiting" are defined as any method known in the art or described herein that decreases the expression or function of a gene product of interest (e.g., a target gene product) "Inhibition" can be in the context of a comparison between two plants, for example, a genetically altered plant versus a wild-type plant. Alternatively, inhibition of expression or function of a target gene product can be in the context of a comparison between plant cells, organelles, organs, tissues, or plant parts within the same plant or between different plants, and includes comparisons between developmental or temporal stages within the same plant or plant part or between plants or plant parts. "Inhibition" includes any relative decrement of function or production of a gene product of interest, up to and including complete elimination of function or production of that gene product. The term "inhibition" encompasses any method or composition that down-regulates translation and/or transcription of the target gene product or functional activity of the target gene product. In an aspect, the mRNA or protein level of one or more genes in a modified plant is less than 95%, less than 90%, less than 80%, less than 70%, less than 60%, less than 50%, less than 40%, less than 30%, less than 20%, less than 10%, less than 5%, less than 4%, less than 3%, less than 2%, or less than 1% of the mRNA or protein level of the same gene in a plant that is not a mutant or that has not been genetically modified to inhibit the expression of that gene.

The term "inhibitory sequence" encompasses any polynucleotide or polypeptide sequence capable of inhibiting the expression or function of a gene involved in nicotine biosynthesis regulation from Nic1b locus in a plant, such as full-length polynucleotide or polypeptide sequences, truncated polynucleotide or polypeptide sequences, fragments of polynucleotide or polypeptide sequences, variants of polynucleotide or polypeptide sequences, sense-oriented nucleotide sequences, antisense-oriented nucleotide sequences, the complement of a sense- or antisense-oriented nucleotide sequence, inverted regions of nucleotide sequences, hairpins of nucleotide sequences, double-stranded nucleotide sequences, single-stranded nucleotide sequences, combinations thereof, and the like. The term "polynucleotide sequence" includes sequences of RNA, DNA, chemically modified nucleic acids, nucleic acid analogs, combinations thereof, and the like.

Inhibitory sequences are designated by the name of the target gene product. Thus, a "ODC inhibitory sequence" refers to an inhibitory sequence that is capable of inhibiting the expression of an ODC gene involved in polyamine biosynthesis regulation in a plant, for example, at the level of transcription and/or translation, or which is capable of inhibiting the function of a gene product. When the phrase "capable of inhibiting" is used in the context of a polynucleotide inhibitory sequence, it is intended to mean that the inhibitory sequence itself exerts the inhibitory effect; or, where the inhibitory sequence encodes an inhibitory nucleotide molecule (for example, hairpin RNA, miRNA, or double-stranded RNA polynucleotides), or encodes an inhibitory polypeptide (e.g., a polypeptide that inhibits expression or function of the target gene product), following its transcription (for example, in the case of an inhibitory sequence encoding a hairpin RNA, miRNA, or double-stranded RNA polynucleotide) or its transcription and translation (in the case of an inhibitory sequence encoding an inhibitory polypeptide), the transcribed or translated product, respectively, exerts the inhibitory effect on the target gene product (e.g., inhibits expression or function of the target gene product).

A ODC inhibitory sequence disclosed can be a sequence triggering gene silencing via any silencing pathway or mechanism known in the art, including, but not limited to, sense suppression/cosuppression, antisense suppression, double-stranded RNA (dsRNA) interference, hairpin RNA interference and intron-containing hairpin RNA interference, amplicon-mediated interference, ribozymes, small interfering RNA, artificial or synthetic microRNA, and artificial trans-acting siRNA. An ODC inhibitory sequence may range from at least about 20 nucleotides, about 50 nucleotides, about 70 nucleotides, about 100 nucleotides, about 150 nucleotides, about 200 nucleotides, about 250 nucleotides, about 300 nucleotides, about 350 nucleotides, about 400 nucleotides, and up to the full-length polynucleotide encoding the proteins of the present disclosure, depending upon the desired outcome. In an aspect, a ODC inhibitory sequence can be a fragment of between about 50 and about 400 nucleotides, between about 70 and about 350 nucleotides, between about 90 and about 325 nucleotides, between about 90 and about 300 nucleotides, between about 90 and about 275 nucleotides, between about 100 and about 400 nucleotides, between about 100 and about 350 nucleotides, between about 100 and about 325 nucleotides, between about 100 and about 300 nucleotides, between about 125 and about 300 nucleotides, or between about 125 and about 275 nucleotides in length.

The use of the term "polynucleotide" is not intended to limit the present disclosure to polynucleotides comprising DNA. Those of ordinary skill in the art will recognize that polynucleotides can comprise ribonucleotides and combinations of ribonucleotides and deoxyribonucleotides. Such deoxyribonucleotides and ribonucleotides include both naturally occurring molecules and synthetic analogues. The polynucleotides of the present disclosure also encompass all forms of sequences including, but not limited to, single-stranded forms, double-stranded forms, hairpins, stem-and-loop structures, and the like.

In an aspect, the present disclosure provides recombinant DNA constructs comprising a promoter that is functional in a tobacco cell and operably linked to a polynucleotide that encodes an RNA molecule capable of binding to an RNA encoding a polypeptide having an amino acid sequence at least 80%, at least 85%, at least 90%, at least 95%, at least 97%, at least 98%, at least 99% identical to an amino acid sequence selected from the group consisting of SEQ ID NOs: 23 to 28, and fragments thereof, and where the RNA molecule suppresses the expression of the polypeptide. In an aspect, the RNA molecule is selected from the group consisting of a microRNA, an siRNA, and a trans-acting siRNA. In another aspect, the recombinant DNA construct encodes a double stranded RNA. Also provided are transgenic tobacco plants or part thereof, cured tobacco material, or tobacco products comprising these recombinant DNA constructs. In an aspect, these transgenic plants, cured tobacco material, or tobacco products comprise a lower level of nicotine compared to a control tobacco plant without the recombinant DNA construct. Further provided are methods of reducing the nicotine level of a tobacco plant, the method comprising transforming a tobacco plant with any of these recombinant DNA constructs.

As used herein, "operably linked" refers to a functional linkage between two or more elements. For example, an operable linkage between a polynucleotide of interest and a regulatory sequence (e.g., a promoter) is a functional link that allows for expression of the polynucleotide of interest. Operably linked elements may be contiguous or non-contiguous.

As used herein and when used in reference to a sequence, "heterologous" refers to a sequence that originates from a foreign species, or, if from the same species, is substantially modified from its native form in composition and/or genomic location by deliberate human intervention. The term also is applicable to nucleic acid constructs, also referred to herein as "polynucleotide constructs" or "nucleotide constructs." In this manner, a "heterologous" nucleic acid construct is intended to mean a construct that originates from a foreign species, or, if from the same species, is substantially modified from its native form in composition and/or genomic location by deliberate human intervention. Heterologous nucleic acid constructs include, but are not limited to, recombinant nucleotide constructs that have been introduced into a plant or plant part thereof, for example, via transformation methods or subsequent breeding of a transgenic plant with another plant of interest. In an aspect, a promoter used is heterologous to the sequence driven by the promoter. In another aspect, a promoter used is heterologous to tobacco. In a further aspect, a promoter used is native to tobacco.

In an aspect, a modified tobacco plant described is a cisgenic plant. As used herein, "cisgenesis" or "cisgenic" refers to genetic modification of a plant, plant cell, or plant genome in which all components (e.g., promoter, donor nucleic acid, selection gene) have only plant origins (i.e., no non-plant origin components are used). In an aspect, a modified plant, plant cell, or plant genome provided is cisgenic. Cisgenic plants, plant cells, and plant genomes provided can lead to ready-to-use tobacco lines. In another aspect, a modified tobacco plant provided comprises no non-tobacco genetic material or sequences.

As used herein, "gene expression" refers to the biosynthesis or production of a gene product, including the transcription and/or translation of the gene product.

In an aspect, recombinant DNA constructs or expression cassettes can also comprise a selectable marker gene for the selection of transgenic cells. Selectable marker genes include, but are not limited to, genes encoding antibiotic resistance, such as those encoding neomycin phosphotransferase II (NEO) and hygromycin phosphotransferase (HPT), as well as genes conferring resistance to herbicidal compounds, such as glufosinate ammonium, bromoxynil, imidazolinones, and 2,4-dichlorophenoxyacetate (2,4-D). Additional selectable markers include phenotypic markers such as β-galactosidase and fluorescent proteins such as green fluorescent protein (GFP).

In an aspect, recombinant DNA constructs or expression cassettes comprise a promoter selected from the group consisting of a constitutive promoter, an inducible promoter, and a tissue-preferred promoter (for example, a leaf-specific or root-specific promoter). Exemplary constitutive promoters include the core promoter of the Rsyn7 promoter and other constitutive promoters disclosed in U.S. Pat. No. 6,072,050; the core CaMV 35S promoter (Odell et al. (1985) Nature 313:810-812); ubiquitin (Christensen et al. (1989) Plant Mol. Biol. 12:619-632 and Christensen et al. (1992) Plant Mol. Biol. 18:675-689); pEMU (Last et al. (1991) Theor. Appl. Genet. 81:581-588); MAS (Velten et al. (1984) EMBO J 3:2723-2730); ALS promoter (U.S. Pat. No. 5,659, 026), and the like. Exemplary chemical-inducible promoters include the tobacco PR-1a promoter, which is activated by salicylic acid. Other chemical-inducible promoters of interest include steroid-responsive promoters (see, for example, the glucocorticoid-inducible promoter in Schena et al. (1991) Proc. Natl. Acad. Sci. USA 88:10421-10425 and McNellis et al. (1998) Plant J. 14(2):247-257) and tetracycline-inducible promoters (see, for example, Gatz et al. (1991) Mol. Gen. Genet. 227:229-237, and U.S. Pat. Nos. 5,814,618 and 5,789,156). Additional exemplary promoters that can be used are those responsible for heat-regulated gene expression, light-regulated gene expression (for example, the pea rbcS-3A; the maize rbcS promoter; the chlorophyll alb-binding protein gene found in pea; or the Arabssu promoter), hormone-regulated gene expression (for example, the abscisic acid (ABA) responsive sequences from the Em gene of wheat; the ABA-inducible HVA1 and HVA22, and rd29A promoters of barley and *Arabidopsis*; and wound-induced gene expression (for example, of wunl), organ specific gene expression (for example, of the tuber-specific storage protein gene; the 23-kDa zein gene from maize described by; or the French bean (β-phaseolin gene), or pathogen-inducible promoters (for example, the PR-1, prp-1, or (β-1,3 glucanase promoters, the fungal-inducible wirla promoter of wheat, and the nematode-inducible promoters, TobRB7-5A and Hmg-1, of tobacco arid parsley, respectively).

In an aspect, a tobacco plant provided further comprises increased or reduced expression of activity of genes involved in nicotine biosynthesis or transport. Genes involved in nicotine biosynthesis include, but are not limited to, arginine decarboxylase (ADC), methylputrescine oxidase (MPO), NADH dehydrogenase, ornithine decarboxylase (ODC), phosphoribosylanthranilate isomerase (PRAI), putrescine N-methyltransferase (PMT), quinolate phosphoribosyl transferase (QPT), and S-adenosyl-methionine synthetase (SAMS). Nicotine Synthase, which catalyzes the condensation step between a nicotinic acid derivative and methylpyrrolinium cation, has not been elucidated although two candidate genes (A622 and NBB1) have been proposed. See US 2007/0240728 A1 and US 2008/0120737A1. A622 encodes an isoflavone reductase-like protein. In addition, several transporters may be involved in the translocation of nicotine. A transporter gene, named MATE, has been cloned and characterized (Morita et al., *PNAS* 106:2447-52 (2009)).

In an aspect, a tobacco plant provided further comprises an increased or reduced level of mRNA, protein, or both of one or more genes encoding a product selected from the group consisting of PMT, MPO, QPT, ADC, ODC, PRAI, SAMS, BBL, MATE, A622, and NBB1, compared to a control tobacco plant. In another aspect, a tobacco plants provided further comprises a transgene directly suppressing the expression of one or more genes encoding a product selected from the group consisting of PMT, MPO, QPT, ADC, ODC, PRAI, SAMS, BBL, MATE, A622, and NBB1. In another aspect, a tobacco plant provided further comprises a transgene or mutation suppressing the expression or activity of one or more genes encoding a product selected from the group consisting of PMT, MPO, QPT, ADC, ODC, PRAI, SAMS, BBL, MATE, A622, and NBB1. In another aspect, a tobacco plant provided further comprises a transgene overexpressing one or more genes encoding a product selected from the group consisting of PMT, MPO, QPT, ADC, ODC, PRAI, SAMS, BBL, MATE, A622, and NBB1.

Also disclosed are the transformation of tobacco plants with recombinant constructs or expression cassettes described using any suitable transformation methods known in the art. Methods for introducing polynucleotide sequences into tobacco plants are known in the art and include, but are not limited to, stable transformation methods, transient transformation methods, and virus-mediated methods. "Stable transformation" refers to transformation where the nucleotide construct of interest introduced into a plant integrates into the genome of the plant and is capable of being inherited by the progeny thereof "Transient transformation" is intended to mean that a sequence is introduced into the plant and is only temporally expressed or is only transiently present in the plant.

Suitable methods of introducing polynucleotides into plant cells of the present disclosure include microinjection (Crossway et al. (1986) *Biotechniques* 4:320-334), electroporation (Shillito et al. (1987) *Meth. Enzymol.* 153:313-336; Riggs et al. (1986) *Proc. Natl. Acad. Sci. USA* 83:5602-5606), *Agrobacterium*-mediated transformation (U.S. Pat. Nos. 5,104,310, 5,149,645, 5,177,010, 5,231,019, 5,463, 174, 5,464,763, 5,469,976, 4,762,785, 5,004,863, 5,159,135, 5,563,055, and 5,981,840), direct gene transfer (Paszkowski et al. (1984) *EMBO J.* 3:2717-2722), and ballistic particle acceleration (see, for example, U.S. Pat. Nos. 4,945,050, 5,141,131, 5,886,244, 5,879,918, and 5,932,782; Tomes et al. (1995) in *Plant Cell, Tissue, and Organ Culture Fundamental Methods*, ed. Gamborg and Phillips (Springer-Verlag, Berlin); McCabe et al. (1988) *Biotechnology* 6:923-926). Also see Weissinger et al. (1988) *Ann. Rev. Genet.* 22:421-477; Christou et al. (1988) *Plant Physiol.* 87:671-674 (soybean); McCabe et al. (1988) *Bio/Technology* 6:923-926 (soybean); Finer and McMullen (1991) *In Vitro Cell Dev. Biol.* 27P: 175-182 (soybean); Singh et al. (1998) *Theor. Appl. Genet.* 96:319-324 (soybean); De Wet et al. (1985) in *The Experimental Manipulation of Ovule Tissues*, ed. Chapman et al. (Longman, N.Y.), pp. 197-209 (pollen); Kaeppler et al. (1990) *Plant Cell Reports* 9:415-418 and Kaeppler et al. (1992) *Theor. Appl. Genet.* 84:560-566 (whisker-mediated transformation); D'Halluin et al. (1992) *Plant Cell* 4:1495-1505 (electroporation).

In another aspect, recombinant constructs or expression cassettes may be introduced into plants by contacting plants with a virus or viral nucleic acids. Generally, such methods involve incorporating an expression cassette of the present disclosure within a viral DNA or RNA molecule. It is recognized that promoters for use in expression cassettes also encompass promoters utilized for transcription by viral RNA polymerases. Methods for introducing polynucleotides into plants and expressing a protein encoded therein, involving viral DNA or RNA molecules, are known in the art. See, for example, U.S. Pat. Nos. 5,889,191, 5,889,190, 5,866,785, 5,589,367, 5,316,931, and Porta et al. (1996) *Molecular Biotechnology* 5:209-221.

Any plant tissue that can be subsequently propagated using clonal methods, whether by organogenesis or embryogenesis, may be transformed with a recombinant construct or an expression cassette. By "organogenesis" in intended the process by which shoots and roots are developed sequentially from meristematic centers. By "embryogenesis" is intended the process by which shoots and roots develop together in a concerted fashion (not sequentially), whether from somatic cells or gametes. Exemplary tissues that are suitable for various transformation protocols described include, but are not limited to, callus tissue, existing meristematic tissue (e.g., apical meristems, axillary buds, and root meristems) and induced meristem tissue (e.g., cotyledon meristem and hypocotyl meristem), hypocotyls, cotyledons, leaf disks, pollen, embryos, and the like.

In an aspect, a tobacco plant provided is from a tobacco type selected from the group consisting of flue-cured tobacco, air-cured tobacco, dark air-cured tobacco, dark fire-cured tobacco, Galpao tobacco, and Oriental tobacco. In another aspect, a tobacco plant provided is from a tobacco type selected from the group consisting of Burley tobacco, Maryland tobacco, and dark tobacco.

In an aspect, a tobacco plant provided is in a flue-cured tobacco background or exhibits one or more flue-cured tobacco characteristic described here. Flue-cured tobaccos (also called Virginia or bright tobaccos) amount to approximately 40% of world tobacco production. Flue-cured tobaccos are often also referred to as "bright tobacco" because of the golden-yellow to deep-orange color it reaches during curing. Flue-cured tobaccos have a light, bright aroma and taste. Flue-cured tobaccos are generally high in sugar and low in oils. Major flue-cured tobacco growing countries are Argentina, Brazil, China, India, Tanzania and the U.S. In an aspect, a low-alkaloid or low-nicotine tobacco plant or seed provided is in a flue-cured tobacco background selected from the group consisting of CC 13, CC 27, CC 33, CC 37, CC 65, CC 67, CC 700, GF 318, GL 338, GL 368, GL 939, K 346, K 399, K326, NC 102, NC 196, NC 291, NC 297, NC 299, NC 471, NC 55, NC 606, NC 71, NC 72, NC 92, PVH 1118, PVH 1452, PVH 2110, SPEIGHT 168, SPEIGHT 220, SPEIGHT 225, SPEIGHT 227, SPEIGHT 236, and any variety essentially derived from any one of the foregoing varieties. In another aspect, a low-alkaloid or low-nicotine tobacco plant or seed provided is in a flue-cured tobacco background selected from the group consisting of Coker 48, Coker 176, Coker 371-Gold, Coker 319, Coker 347, GL 939, K 149, K326, K 340, K 346, K 358, K 394, K 399, K 730, NC 27NF, NC 37NF, NC 55, NC 60, NC 71, NC 72, NC 82, NC 95, NC 297, NC 606, NC 729, NC 2326, McNair 373, McNair 944, Ox 207, Ox 414 NF, Reams 126, Reams 713, Reams 744, RG 8, RG 11, RG 13, RG 17, RG 22, RG 81, RG H4, RG H51, Speight H-20, Speight G-28, Speight G-58, Speight G-70, Speight G-108, Speight G-111, Speight G-117, Speight 168, Speight 179, Speight NF-3, Va 116, Va 182, and any variety essentially derived from any one of the foregoing varieties. See WO 2004/041006 A1. In a further aspect, low-alkaloid or low-nicotine tobacco plants, seeds, hybrids, varieties, or lines are in any flue cured background selected from the group consisting of K326, K346, and NC196.

In an aspect, a tobacco plant provided is in an air-cured tobacco background or exhibits one or more air-cured tobacco characteristic described here. Air-cured tobaccos include Burley, Maryland, and dark tobaccos. The common factor is that curing is primarily without artificial sources of heat and humidity. Burley tobaccos are light to dark brown in color, high in oil, and low in sugar. Burley tobaccos are air-cured in barns. Major Burley growing countries are Argentina, Brazil, Italy, Malawi, and the U.S. Maryland tobaccos are extremely fluffy, have good burning properties, low nicotine and a neutral aroma. Major Maryland growing countries include the U.S. and Italy. In an aspect, a low-alkaloid or low-nicotine tobacco plant or seed provided is in a Burley tobacco background selected from the group consisting of Clay 402, Clay 403, Clay 502, Ky 14, Ky 907, Ky 910, Ky 8959, NC 2, NC 3, NC 4, NC 5, NC 2000, TN 86, TN 90, TN 97, R 610, R 630, R 711, R 712, NCBH 129, Bu 21 xKy 10, HBO4P, Ky 14×L 8, Kt 200, Newton 98, Pedigo 561, Pf561 and Va 509. In a further aspect, low-alkaloid or low-nicotine tobacco plants, seeds, hybrids, varieties, or lines are in any Burley background selected from the group consisting of TN 90, KT 209, KT 206, KT212, and HB 4488. In another aspect, a low-alkaloid or low-nicotine tobacco plant or seed provided is in a Maryland tobacco background selected from the group consisting of Md 10, Md 40, Md 201, Md 609, Md 872 and Md 341.

In an aspect, a tobacco plant provided is in a dark air-cured tobacco background or exhibits one or more dark air-cured tobacco characteristic described here. Dark air-cured tobaccos are distinguished from other types primarily by its curing process which gives dark air-cured tobacco its medium- to dark-brown color and distinct aroma. Dark air-cured tobaccos are mainly used in the production of chewing tobacco and snuff. In an aspect, a low-alkaloid or low-nicotine tobacco plant or seed provided is in a dark air-cured tobacco background selected from the group consisting of Sumatra, Jatim, Dominican Cubano, Besuki, One sucker, Green River, Virginia sun-cured, and Paraguan Passado.

In an aspect, a tobacco plant provided is in a dark fire-cured tobacco background or exhibits one or more dark fire-cured tobacco characteristic described here. Dark fire-cured tobaccos are generally cured with low-burning wood fires on the floors of closed curing barns. Their leaves have low sugar content but high nicotine content. Dark fire-cured tobaccos are used for making pipe blends, cigarettes, chewing tobacco, snuff and strong-tasting cigars. Major growing regions for dark fire-cured tobaccos are Tennessee, Kentucky, and Virginia, USA. In an aspect, a low-alkaloid or low-nicotine tobacco plant or seed provided is in a dark fire-cured tobacco background selected from the group consisting of Narrow Leaf Madole, Improved Madole, Tom Rosson Madole, Newton's VH Madole, Little Crittenden, Green Wood, Little Wood, Small Stalk Black Mammoth, DT 508, DT 518, DT 592, KY 171, DF 911, DF 485, TN D94, TN D950, VA 309, and VA 359.

In an aspect, a tobacco plant provided is in an Oriental tobacco background or exhibits one or more Oriental tobacco characteristic described here. Oriental tobaccos are also referred to as Greek, aroma and Turkish tobaccos due to the fact that they are typically grown in eastern Mediterranean regions such as Turkey, Greece, Bulgaria, Macedonia, Syria, Lebanon, Italy, and Romania. The small plant and leaf size, characteristic of today's Oriental varieties, as well as its unique aroma properties are a result of the plant's adaptation to the poor soil and stressful climatic conditions in which it develop over many past centuries. In an aspect, a low-alkaloid or low-nicotine tobacco plant or seed provided is in an Oriental tobacco background selected from the group consisting of Izmir, Katerini, Samsun, Basma and Krumovgrad, Trabzon, Thesalian, Tasova, Sinop, Izmit, Hendek, Edirne, Semdinli, Adiyanman, Yayladag, Iskenderun, Duzce, Macedonian, Mavra, Prilep, Bafra, Bursa, Bucak, Bitlis, Balikesir, and any variety essentially derived from any one of the foregoing varieties.

In an aspect, low-alkaloid or low-nicotine tobacco plants, seeds, hybrids, varieties, or lines are essentially derived from or in the genetic background of BU 64, CC 101, CC 200, CC 27, CC 301, CC 400, CC 500, CC 600, CC 700, CC 800, CC 900, Coker 176, Coker 319, Coker 371 Gold, Coker 48, CU 263, DF911, Galpao tobacco, GL 26H, GL 350, GL 600, GL 737, GL 939, GL 973, HB 04P, K 149, K 326, K 346, K 358, K394, K 399, K 730, KDH 959, KT 200, KT204LC, KY 10, KY 14, KY 160, KY 17, KY 171, KY 907, KY907LC, KTY14×L8 LC, Little Crittenden, McNair 373, McNair 944, msKY 14×L8, Narrow Leaf Madole, NC 100, NC 102, NC 2000, NC 291, NC 297, NC 299, NC 3, NC 4, NC 5, NC 6, NC7, NC 606, NC 71, NC 72, NC 810, NC BH 129, NC 2002, Neal Smith Madole, OXFORD 207, 'Perique' tobacco, PVH03, PVH09, PVH19, PVH50, PVH51, R 610, R 630, R 7-11, R 7-12, RG 17, RG 81, RG H51, RGH 4, RGH 51, RS 1410, Speight 168, Speight 172, Speight 179, Speight 210, Speight 220, Speight 225, Speight 227, Speight 234, Speight G-28, Speight G-70, Speight H-6, Speight H20, Speight NF3, TI 1406, TI 1269, TN 86, TN86LC, TN 90, TN 97, TN97LC, TN D94, TN D950, TR (Tom Rosson) Madole, VA 309, or VA359, Maryland 609, HB3307PLC, HB4488PLC, KT206LC, KT209LC, KT210LC, KT212LC, R610LC, PVH2310, NC196, KTD14LC, KTD6LC, KTD8LC, PD7302LC, PD7305LC, PD7309LC, PD7318LC, PD7319LC, PD7312LC, ShireyLC, or any commercial tobacco variety according to standard tobacco breeding techniques known in the art.

All foregoing mentioned specific varieties of dark air-cured, Burley, Maryland, dark fire-cured, or Oriental type are listed only for exemplary purposes. Any additional dark air-cured, Burley, Maryland, dark fire-cured, Oriental varieties are also contemplated in the present application.

Also provided are populations of tobacco plants described. In an aspect, a population of tobacco plants has a planting density of between about 5,000 and about 8000, between about 5,000 and about 7,600, between about 5,000 and about 7,200, between about 5,000 and about 6,800, between about 5,000 and about 6,400, between about 5,000 and about 6,000, between about 5,000 and about 5,600, between about 5,000 and about 5,200, between about 5,200 and about 8,000, between about 5,600 and about 8,000, between about 6,000 and about 8,000, between about 6,400 and about 8,000, between about 6,800 and about 8,000, between about 7,200 and about 8,000, or between about 7,600 and about 8,000 plants per acre. In another aspect, a population of tobacco plants is in a soil type with low to medium fertility.

Also provided are containers of seeds from tobacco plants described. A container of tobacco seeds of the present disclosure may contain any number, weight, or volume of seeds. For example, a container can contain at least, or greater than, about 100, 200, 300, 400, 500, 600, 700, 800, 900, 1000, 1500, 2000, 2500, 3000, 3500, 4000 or more seeds. Alternatively, the container can contain at least, or greater than, about 1 ounce, 5 ounces, 10 ounces, 1 pound, 2 pounds, 3 pounds, 4 pounds, 5 pounds or more seeds. Containers of tobacco seeds may be any container available in the art. By way of non-limiting example, a container may be a box, a bag, a packet, a pouch, a tape roll, a tube, or a bottle.

Also provided is cured tobacco material made from a low-alkaloid or low-nicotine tobacco plant described. Further provided is cured tobacco material made from a tobacco plant described with higher levels of total alkaloid or nicotine.

"Curing" is the aging process that reduces moisture and brings about the destruction of chlorophyll giving tobacco leaves a golden color and by which starch is converted to sugar. Cured tobacco therefore has a higher reducing sugar content and a lower starch content compared to harvested green leaf. In an aspect, green leaf tobacco provided can be cured using conventional means, e.g., flue-cured, barn-cured, fire-cured, air-cured or sun-cured. See, for example, Tso (1999, Chapter 1 in Tobacco, Production, Chemistry and Technology, Davis & Nielsen, eds., Blackwell Publishing, Oxford) for a description of different types of curing methods. Cured tobacco is usually aged in a wooden drum (e.g., a hogshead) or cardboard cartons in compressed conditions for several years (e.g., two to five years), at a moisture content ranging from 10% to about 25%. See, U.S. Pat. Nos. 4,516,590 and 5,372,149. Cured and aged tobacco then can be further processed. Further processing includes conditioning the tobacco under vacuum with or without the introduction of steam at various temperatures, pasteurization, and fermentation. Fermentation typically is characterized by high initial moisture content, heat generation, and a 10 to 20% loss of dry weight. See, e.g., U.S. Pat. Nos. 4,528,993, 4,660,577, 4,848,373, 5,372,149; U.S. Publication No. 2005/0178398; and Tso (1999, Chapter 1 in Tobacco, Production, Chemistry and Technology, Davis & Nielsen, eds., Blackwell Publishing, Oxford). Cure, aged, and fermented tobacco can be further processed (e.g., cut, shredded, expanded, or blended). See, for example, U.S. Pat. Nos. 4,528,993; 4,660,577; and 4,987,907. In an aspect, the cured tobacco material of the present disclosure is sun-cured. In another aspect, the cured tobacco material of the present disclosure is flue-cured, air-cured, or fire-cured.

Tobacco material obtained from the tobacco lines, varieties or hybrids of the present disclosure can be used to make tobacco products. As used herein, "tobacco product" is defined as any product made or derived from tobacco that is intended for human use or consumption.

Tobacco products provided include, without limitation, cigarette products (e.g., cigarettes and bidi cigarettes), cigar products (e.g., cigar wrapping tobacco and cigarillos), pipe tobacco products, products derived from tobacco, tobacco-derived nicotine products, smokeless tobacco products (e.g., moist snuff, dry snuff, and chewing tobacco), films, chewables, tabs, shaped parts, gels, consumable units, insoluble matrices, hollow shapes, reconstituted tobacco, expanded tobacco, and the like. See, e.g., U.S. Patent Publication No. US 2006/0191548.

As used herein, "cigarette" refers a tobacco product having a "rod" and "filler". The cigarette "rod" includes the cigarette paper, filter, plug wrap (used to contain filtration materials), tipping paper that holds the cigarette paper (including the filler) to the filter, and all glues that hold these components together. The "filler" includes (1) all tobaccos, including but not limited to reconstituted and expanded tobacco, (2) non-tobacco substitutes (including but not limited to herbs, non-tobacco plant materials and other spices that may accompany tobaccos rolled within the cigarette paper), (3) casings, (4) flavorings, and (5) all other additives (that are mixed into tobaccos and substitutes and rolled into the cigarette).

As used herein, "reconstituted tobacco" refers to a part of tobacco filler made from tobacco dust and other tobacco scrap material, processed into sheet form and cut into strips to resemble tobacco. In addition to the cost savings, reconstituted tobacco is very important for its contribution to cigarette taste from processing flavor development using reactions between ammonia and sugars.

As used herein, "expanded tobacco" refers to a part of tobacco filler which is processed through expansion of suitable gases so that the tobacco is "puffed" resulting in reduced density and greater filling capacity. It reduces the weight of tobacco used in cigarettes.

Tobacco products derived from plants of the present disclosure also include cigarettes and other smoking articles, particularly those smoking articles including filter elements, where the rod of smokable material includes cured tobacco within a tobacco blend. In an aspect, a tobacco product of the present disclosure is selected from the group consisting of a cigarillo, a non-ventilated recess filter cigarette, a vented recess filter cigarette, a cigar, snuff, pipe tobacco, cigar tobacco, cigarette tobacco, chewing tobacco, leaf tobacco, hookah tobacco, shredded tobacco, and cut tobacco. In another aspect, a tobacco product of the present disclosure is a smokeless tobacco product. Smokeless tobacco products are not combusted and include, but not limited to, chewing tobacco, moist smokeless tobacco, snus, and dry snuff Chewing tobacco is coarsely divided tobacco leaf that is typically packaged in a large pouch-like package and used in a plug or twist. Moist smokeless tobacco is a moist, more finely divided tobacco that is provided in loose form or in pouch form and is typically packaged in round cans and used as a pinch or in a pouch placed between an adult tobacco consumer's cheek and gum. Snus is a heat treated smokeless tobacco. Dry snuff is finely ground tobacco that is placed in the mouth or used nasally. In a further aspect, a tobacco product of the present disclosure is selected from the group consisting of loose leaf chewing tobacco, plug chewing tobacco, moist snuff, and nasal snuff. In yet another aspect, a tobacco product of the present disclosure is selected from the group consisting of an electronically heated cigarette, an e-cigarette, an electronic vaporing device.

In an aspect, a tobacco product of the present disclosure can be a blended tobacco product. In one aspect, a blended tobacco product comprises cured tobacco materials. In an aspect, a cured tobacco material constitutes about at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, or at least 95% of cured tobacco in a tobacco blend by weight. In one aspect, a cured tobacco material constitutes about at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, or at least 95% of cured tobacco in a tobacco blend by volume.

In an aspect, a tobacco product of the present disclosure can be a low nicotine tobacco product. In a further aspect, a tobacco product of the present disclosure may comprise nornicotine at a level of less than about 3 mg/g. For example, the nornicotine content in such a product can be about 3.0 mg/g, 2.5 mg/g, 2.0 mg/g, 1.5 mg/g, 1.0 mg/g, 750 μg/g, 500 pg/g, 250 pg/g, 100 pg/g, 75 pg/g, 50 pg/g, 25 pg/g, 10 pg/g, 7.0 pg/g, 5.0 pg/g, 4.0 pg/g, 2.0 pg/g, 1.0 pg/g, 0.5 pg/g, 0.4 pg/g, 0.2 pg/g, 0.1 pg/g, 0.05 pg/g, 0.01 pg/g, or undetectable.

In an aspect, cured tobacco material or tobacco products provided comprise an average nicotine or total alkaloid level selected from the group consisting of about 0.01%, 0.02%, 0.05%, 0.75%, 0.1%, 0.15%, 0.2%, 0.3%, 0.35%, 0.4%, 0.5%, 0.6%, 0.7%, 0.8%, 0.9%, 1%, 1.1%, 1.2%, 1.3%, 1.4%, 1.5%, 1.6%, 1.7%, 1.8%, 1.9%, 2%, 2.1%, 2.2%, 2.3%, 2.4%, 2.5%, 2.6%, 2.7%, 2.8%, 2.9%, 3%, 3.1%, 3.2%, 3.3%, 3.4%, 3.5%, 3.6%, 3.7%, 3.8%, 3.9%, 4%, 5%, 6%, 7%, 8%, and 9% on a dry weight basis. In another aspect, cured tobacco material or tobacco products provided comprise an average nicotine or total alkaloid level selected from the group consisting of about between 0.01% and 0.02%, between 0.02% and 0.05%, between 0.05% and 0.75%, between 0.75% and 0.1%, between 0.1% and 0.15%, between 0.15% and 0.2%, between 0.2% and 0.3%, between 0.3% and 0.35%, between 0.35% and 0.4%, between 0.4% and 0.5%, between 0.5% and 0.6%, between 0.6% and 0.7%, between 0.7% and 0.8%, between 0.8% and 0.9%, between 0.9% and 1%, between 1% and 1.1%, between 1.1% and 1.2%, between 1.2% and 1.3%, between 1.3% and 1.4%, between 1.4% and 1.5%, between 1.5% and 1.6%, between 1.6% and 1.7%, between 1.7% and 1.8%, between 1.8% and 1.9%, between 1.9% and 2%, between 2% and 2.1%, between 2.1% and 2.2%, between 2.2% and 2.3%, between 2.3% and 2.4%, between 2.4% and 2.5%, between 2.5% and 2.6%, between 2.6% and 2.7%, between 2.7% and 2.8%, between 2.8% and 2.9%, between 2.9% and 3%, between 3% and 3.1%, between 3.1% and 3.2%, between 3.2% and 3.3%, between 3.3% and 3.4%, between 3.4% and 3.5%, and between 3.5% and 3.6% on a dry weight basis. In a further aspect, cured tobacco material or tobacco products provided comprise an average nicotine or total alkaloid level selected from the group consisting of about between 0.01° 4 and 0.1%, between 0.02% and 0.2%, between 0.03% and 0.3%, between 0.04% and 0.4%, between 0.05% and 0.5%, between 0.75% and 1%, between 0.1% and 1.5%, between 0.15% and 2%, between 0.2% and 3%, and between 0.3% and 3.5% on a dry weight basis.

The present disclosure also provides methods for breeding tobacco lines, cultivars, or varieties comprising a desirable level of total alkaloid or nicotine, e.g., low nicotine or nicotine free. Breeding can be carried out via any known procedures. DNA fingerprinting, SNP mapping, haplotype mapping or similar technologies may be used in a marker-assisted selection (MAS) breeding program to transfer or breed a desirable trait or allele into a tobacco plant. For example, a breeder can create segregating populations in a $F_2$ or backcross generation using F1 hybrid plants or further crossing the F1 hybrid plants with other donor plants with an agronomically desirable genotype. Plants in the $F_2$ or back-cross generations can be screened for a desired agronomic trait or a desirable chemical profile using one of the techniques known in the art or listed herein. Depending on the expected inheritance pattern or the MAS technology used, self-pollination of selected plants before each cycle of backcrossing to aid identification of the desired individual plants can be performed. Backcrossing or other breeding procedure can be repeated until the desired phenotype of the recurrent parent is recovered. A recurrent parent in the present disclosure can be a flue-cured variety, a Burley variety, a dark air-cured variety, a dark fire-cured variety, or an Oriental variety. Other breeding techniques can be found, for example, in Wernsman, E. A., and Rufty, R. C. 1987. Chapter Seventeen. Tobacco. Pages 669-698 In: Cultivar Development. Crop Species. W. H. Fehr (ed.), MacMillan Publishing Go., Inc., New York, N.Y., incorporated herein by reference in their entirety.

Results of a plant breeding program using the tobacco plants described includes useful lines, cultivars, varieties, progeny, inbreds, and hybrids of the present disclosure. As used herein, the term "variety" refers to a population of plants that share constant characteristics which separate them from other plants of the same species. A variety is often, although not always, sold commercially. While possessing one or more distinctive traits, a variety is further characterized by a very small overall variation between individuals within that variety. A "pure line" variety may be created by several generations of self-pollination and selection, or vegetative propagation from a single parent using tissue or cell culture techniques. A variety can be essentially derived from another line or variety. As defined by the International Convention for the Protection of New Varieties of Plants (Dec. 2, 1961, as revised at Geneva on Nov. 10, 1972; on Oct. 23, 1978; and on Mar. 19, 1991), a variety is "essentially derived" from an initial variety if: a) it is predominantly derived from the initial variety, or from a variety that is predominantly derived from the initial variety, while retaining the expression of the essential characteristics that result from the genotype or combination of genotypes of the initial variety; b) it is clearly distinguishable from the initial variety; and c) except for the differences which result from the act of derivation, it conforms to the initial variety in the expression of the essential characteristics that result from the genotype or combination of genotypes of the initial variety. Essentially derived varieties can be obtained, for example, by the selection of a natural or induced mutant, a somaclonal variant, a variant individual from plants of the initial variety, backcrossing, or transformation. A first tobacco variety and a second tobacco variety from which the first variety is essentially derived, are considered as having essentially identical genetic background. A "line" as distinguished from a variety most often denotes a group of plants used non-commercially, for example in plant research. A line typically displays little overall variation between individuals for one or more traits of interest, although there may be some variation between individuals for other traits.

As used herein, "locus" is a chromosome region where a polymorphic nucleic acid, trait determinant, gene, or marker is located. The loci of this disclosure comprise one or more polymorphisms in a population; e.g., alternative alleles are present in some individuals. As used herein, "allele" refers to an alternative nucleic acid sequence at a particular locus. The length of an allele can be as small as 1 nucleotide base, but is typically larger. For example, a first allele can occur on one chromosome, while a second allele occurs on a second homologous chromosome, e.g., as occurs for different chromosomes of a heterozygous individual, or between different homozygous or heterozygous individuals in a population. As used herein, the term "chromosome interval" designates a contiguous linear span of genomic DNA that resides on a single chromosome.

As used herein, "introgression" or "introgress" refers to the transmission of a desired allele of a genetic locus from one genetic background to another.

As used herein, "crossed" or "cross" means to produce progeny via fertilization (e.g. cells, seeds or plants) and includes crosses between plants (sexual) and self fertilization (selfing).

As used herein, "backcross" and "backcrossing" refer to the process whereby a progeny plant is repeatedly crossed back to one of its parents. In a backcrossing scheme, the "donor" parent refers to the parental plant with the desired gene or locus to be introgressed. The "recipient" parent (used one or more times) or "recurrent" parent (used two or more times) refers to the parental plant into which the gene or locus is being introgressed. The initial cross gives rise to the F1 generation. The term "BC1" refers to the second use of the recurrent parent, "BC2" refers to the third use of the recurrent parent, and so on. In an aspect, a backcross is performed repeatedly, with a progeny individual of each successive backcross generation being itself backcrossed to the same parental genotype.

As used herein, "single gene converted" or "single gene conversion" refers to plants that are developed using a plant breeding technique known as backcrossing, or via genetic engineering, where essentially all of the desired morphological and physiological characteristics of a variety are recovered in addition to the single gene transferred into the variety via the backcrossing technique or via genetic engineering.

As used herein, "elite variety" means any variety that has resulted from breeding and selection for superior agronomic performance.

As used herein, "selecting" or "selection" in the context of marker-assisted selection or breeding refer to the act of picking or choosing desired individuals, normally from a population, based on certain pre-determined criteria.

As used herein, the term "trait" refers to one or more detectable characteristics of a cell or organism which can be influenced by genotype. The phenotype can be observable to the naked eye, or by any other means of evaluation known in the art, e.g., microscopy, biochemical analysis, genomic analysis, an assay for a particular disease tolerance, etc. In some cases, a phenotype is directly controlled by a single gene or genetic locus, e.g., a "single gene trait." In other cases, a phenotype is the result of several genes.

It is understood that any tobacco plant of the present disclosure can further comprise additional agronomically desirable traits, for example, by transformation with a genetic construct or transgene using a technique known in the art. Without limitation, an example of a desired trait is herbicide resistance, pest resistance, disease resistance; high yield; high grade index value; curability; curing quality; mechanical harvestability; holding ability; leaf quality; height, plant maturation (e.g., early maturing, early to medium maturing, medium maturing, medium to late maturing, or late maturing); stalk size (e.g., a small, medium, or a large stalk); or leaf number per plant (e.g., a small (e.g., 5-10 leaves), medium (e.g., 11-15 leaves), or large (e.g., 16-21) number of leaves), or any combination. In an aspect, low-nicotine or nicotine-free tobacco plants or seeds disclosed comprise one or more transgenes expressing one or more insecticidal proteins, such as, for example, a crystal protein of *Bacillus thuringiensis* or a vegetative insecticidal protein from *Bacillus cereus*, such as VIP3 (see, for example, Estruch et al. (1997) *Nat. Biotechnol.* 15:137). In another aspect, tobacco plants further comprise an introgressed trait conferring resistance to brown stem rot (U.S. Pat. No. 5,689,035) or resistance to cyst nematodes (U.S. Pat. No. 5,491,081).

The present disclosure also provides tobacco plants comprising an altered nicotine or total alkaloid level but having a yield comparable to the yield of corresponding initial tobacco plants without such a nicotine level alternation. In an aspect, a low-nicotine or nicotine-free tobacco variety provides a yield selected from the group consisting of about between 1200 and 3500, between 1300 and 3400, between 1400 and 3300, between 1500 and 3200, between 1600 and 3100, between 1700 and 3000, between 1800 and 2900, between 1900 and 2800, between 2000 and 2700, between 2100 and 2600, between 2200 and 2500, and between 2300 and 2400 lbs/acre. In another aspect, a low-nicotine or nicotine-free tobacco variety provides a yield selected from the group consisting of about between 1200 and 3500, between 1300 and 3500, between 1400 and 3500, between 1500 and 3500, between 1600 and 3500, between 1700 and 3500, between 1800 and 3500, between 1900 and 3500, between 2000 and 3500, between 2100 and 3500, between 2200 and 3500, between 2300 and 3500, between 2400 and 3500, between 2500 and 3500, between 2600 and 3500, between 2700 and 3500, between 2800 and 3500, between 2900 and 3500, between 3000 and 3500, and between 3100 and 3500 lbs/acre. In a further aspect, low-nicotine or nicotine-free tobacco plants provide a yield between 65% and 130%, between 70% and 130%, between 75% and 130%, between 80% and 130%, between 85% and 130%, between 90% and 130%, between 95% and 130%, between 100% and 130%, between 105% and 130%, between 110% and 130%, between 115% and 130%, or between 120% and 130% of the yield of a control plant having essentially identical genetic background except a nic1b mutation, a nic2 mutation, a Nic1b transgene, a Nic2 transgene, or combinations thereof. In a further aspect, low-nicotine or nicotine-free tobacco plants provide a yield between 70% and 125%, between 75% and 120%, between 80% and 115%, between 85% and 110%, or between 90% and 100% of the yield of a control plant having essentially identical genetic background except a nic1 mutation, a nic2 mutation, a Nic1 transgene, a Nic2 transgene, or combinations thereof.

In an aspect, a tobacco plant (e.g., a low-nicotine, nicotine-free, or low-alkaloid tobacco variety) does not exhibit one or more, two or more, three or more, or all of the LA BU21 traits selected from the group consisting of lower yield, delayed ripening and senescence, higher susceptibility to insect herbivory, increased polyamine content after topping, higher chlorophyll, more mesophyll cells per unit leaf area, and poor end-product quality after curing. In an aspect, a tobacco plant disclosed (e.g., a low-nicotine, nicotine-free, or low-alkaloid tobacco variety) does not exhibit two or more of the LA BU21 traits selected from the group consisting of lower yield, delayed ripening and senescence, higher susceptibility to insect herbivory, increased polyamine content after topping, higher chlorophyll, more mesophyll cells per unit leaf area, and poor end-product quality after curing. In an aspect, a tobacco plant disclosed (e.g., a low-nicotine, nicotine-free, or low-alkaloid tobacco variety) does not exhibit three or more of the LA BU21 traits selected from the group consisting of lower yield, delayed ripening and senescence, higher susceptibility to insect herbivory, increased polyamine content after topping, higher chlorophyll, more mesophyll cells per unit leaf area, and poor end-product quality after curing. In an aspect, a tobacco plant disclosed (e.g., a low-nicotine, nicotine-free, or low-alkaloid tobacco variety) exhibits at a lower level compared to LA BU21, LAFC53, or LN KY171, one or more, two or more, three or more, or all of the LA BU21 traits selected from the group consisting of lower yield, delayed ripening and senescence, higher susceptibility to insect herbivory, increased polyamine content after topping, higher chlorophyll, more mesophyll cells per unit leaf area, and poor end-product quality after curing. In an aspect, a tobacco plant disclosed (e.g., a low-nicotine, nicotine-free, or low-alkaloid tobacco variety) exhibits at a lower level compared to LA BU21, LAFC53, or LN KY171, two or more of the LA BU21 traits selected from the group consisting of lower yield, delayed ripening and senescence, higher susceptibility to insect herbivory, increased polyamine content after topping, higher chlorophyll, more mesophyll cells per unit leaf area, and poor end-product quality after curing. In an aspect, a tobacco plant disclosed (e.g., a low-nicotine, nicotine-free, or low-alkaloid tobacco variety) exhibits at a lower level compared to LA BU21, LAFC53, or LN KY171, three or more, or all of the LA BU21 traits selected from the group consisting of lower yield, delayed ripening and senescence, higher susceptibility to insect herbivory, increased polyamine content after topping, higher chlorophyll, more mesophyll cells per unit leaf area, and poor end-product quality after curing.

In an aspect, a modified tobacco plant (e.g., a low-nicotine, nicotine-free, or low-alkaloid tobacco variety) comprises a modification conferring a desired trait (e.g., low-nicotine, nicotine-free, or low-alkaloid) without substantially impacting a trait selected from the group consisting of yield, ripening and senescence, susceptibility to insect herbivory, polyamine content after topping, chlorophyll level, mesophyll cell number per unit leaf area, and end-product quality after curing.

In an aspect, a modified tobacco plant comprises a modification conferring a desired trait (e.g., low-nicotine, nicotine-free, or low-alkaloid) and further comprises a trait substantially comparable to an unmodified control plant, where the trait is selected from the group consisting of yield, ripening and senescence, susceptibility to insect herbivory, polyamine content after topping, chlorophyll level, mesophyll cell number per unit leaf area, and end-product quality after curing.

In an aspect, a modified tobacco plant comprises a modification conferring a desired trait (e.g., low-nicotine, nicotine-free, or low-alkaloid) and further comprises a yield which is more than 80%, more than 85%, more than 90%, more than 95%, more than 100%, more than 105%, more than 110%, more than 115%, more than 120%, more than 125%, more than 130%, more than 135%, or more than 140% relative to the yield of an unmodified control plant. In an aspect, a modified tobacco plant disclosed comprises a modification conferring a desired trait (e.g., low-nicotine, nicotine-free, or low-alkaloid) and further comprises a yield which is between 70% and 140%, between 75% and 135%, between 80% and 130%, between 85% and 125%, between 90% and 120%, between 95% and 115%, or between 100% and 110% relative to the yield of an unmodified control plant. In an aspect, a modified tobacco plant disclosed comprises a modification conferring a desired trait (e.g., low-nicotine, nicotine-free, or low-alkaloid) and further comprises a yield which is between 70% and 80%, between 75% and 85%, between 80% and 90%, between 85% and 95%, between 90% and 100%, between 95% and 105%, between 105% and 115%, between 110% and 120%, between 115% to 125%, between 120% and 130%, between 125 and 135%, or between 130% and 140% relative to the yield of an unmodified control plant.

In an aspect, a modified tobacco plant comprises a modification conferring a desired trait (e.g., low-nicotine, nicotine-free, or low-alkaloid) and further comprises a polyamine content after topping which is more than 80%, more than 85%, more than 90%, more than 95%, more than 100%, more than 105%, more than 110%, more than 115%, more than 120%, more than 125%, more than 130%, more than 135%, or more than 140% relative to the polyamine content after topping of an unmodified control plant. In an aspect, a modified tobacco plant disclosed comprises a modification conferring a desired trait (e.g., low-nicotine, nicotine-free, or low-alkaloid) and further comprises a polyamine content after topping which is between 70% and 140%, between 75% and 135%, between 80% and 130%, between 85% and 125%, between 90% and 120%, between 95% and 115%, or between 100% and 110% relative to the polyamine content after topping of an unmodified control plant. In an aspect, a modified tobacco plant disclosed comprises a modification conferring a desired trait (e.g., low-nicotine, nicotine-free, or low-alkaloid) and further comprises a polyamine content after topping which is between 70% and 80%, between 75% and 85%, between 80% and 90%, between 85% and 95%, between 90% and 100%, between 95% and 105%, between 105% and 115%, between 110% and 120%, between 115% to 125%, between 120% and 130%, between 125 and 135%, or between 130% and 140% relative to the polyamine content after topping of an unmodified control plant.

In an aspect, a modified tobacco plant comprises a modification conferring a desired trait (e.g., low-nicotine, nicotine-free, or low-alkaloid) and further comprises a chlorophyll level which is more than 80%, more than 85%, more than 90%, more than 95%, more than 100%, more than 105%, more than 110%, more than 115%, more than 120%, more than 125%, more than 130%, more than 135%, or more than 140% relative to the chlorophyll level of an unmodified control plant. In an aspect, a modified tobacco plant disclosed comprises a modification conferring a desired trait (e.g., low-nicotine, nicotine-free, or low-alkaloid) and further comprises a chlorophyll level which is between 70% and 140%, between 75% and 135%, between 80% and 130%, between 85% and 125%, between 90% and 120%, between 95% and 115%, or between 100% and 110% relative to the chlorophyll level of an unmodified control plant. In an aspect, a modified tobacco plant disclosed comprises a modification conferring a desired trait (e.g., low-nicotine, nicotine-free, or low-alkaloid) and further comprises a chlorophyll level which is between 70% and 80%, between 75% and 85%, between 80% and 90%, between 85% and 95%, between 90% and 100%, between 95% and 105%, between 105% and 115%, between 110% and 120%, between 115% to 125%, between 120% and 130%, between 125 and 135%, or between 130% and 140% relative to the chlorophyll level of an unmodified control plant.

In an aspect, a modified tobacco plant comprises a modification conferring a desired trait (e.g., low-nicotine, nicotine-free, or low-alkaloid) and further comprises a mesophyll cell number per unit leaf area which is more than 80%, more than 85%, more than 90%, more than 95%, more than 100%, more than 105%, more than 110%, more than 115%, more than 120%, more than 125%, more than 130%, more than 135%, or more than 140% relative to the mesophyll cell number per unit leaf area of an unmodified control plant. In an aspect, a modified tobacco plant disclosed comprises a modification conferring a desired trait (e.g., low-nicotine, nicotine-free, or low-alkaloid) and further comprises a mesophyll cell number per unit leaf area which is between 70% and 140%, between 75% and 135%, between 80% and 130%, between 85% and 125%, between 90% and 120%, between 95% and 115%, or between 100% and 110% relative to the mesophyll cell number per unit leaf area of an unmodified control plant. In an aspect, a modified tobacco plant disclosed comprises a modification conferring a desired trait (e.g., low-nicotine, nicotine-free, or low-alkaloid) and further comprises a mesophyll cell number per unit leaf area which is between 70% and 80%, between 75% and 85%, between 80% and 90%, between 85% and 95%, between 90% and 100%, between 95% and 105%, between 105% and 115%, between 110% and 120%, between 115% to 125%, between 120% and 130%, between 125 and 135%, or between 130% and 140% relative to the mesophyll cell number per unit leaf area of an unmodified control plant.

In an aspect, a low-nicotine or nicotine-free tobacco variety is adapted for machine harvesting. In another aspect, a low-nicotine or nicotine-free tobacco variety disclosed is harvested mechanically.

In an aspect, a method for improving leaf quality in a reduced-alkaloid tobacco plant is provided, the method comprising: growing a tobacco plant; reducing the level of putrescine in the tobacco plant, and harvesting leaves from the tobacco plant.

In an aspect, a method for improving leaf quality in a reduced-alkaloid tobacco plant is provided, the method comprising: growing a tobacco plant; suppressing the expression or activity of an ornithine decarboxylase (ODC) gene in the tobacco plant, and harvesting leaves from the tobacco plant. In one aspect, the suppressing step is within 2, 4, 6, or 8 WPT. In an aspect, the suppressing step comprises suppressing a ODC gene both prior to and after topping a tobacco plant. In one aspect, the suppressing step does not include the use of a chemical inhibitor. In an aspect, the suppressing step is accomplished by inducing the expression of a non-coding RNA for suppression of an ornithine decarboxylase (ODC) gene. In one aspect, the suppressing step comprises applying an ODC inhibitor to the tobacco plant. In an aspect, the suppressing is accomplished by applying an ODC inhibitor to a tobacco plant. In one aspect, an ODC inhibitor is DFMO.

In an aspect, tobacco plants provided are hybrid plants. Hybrids can be produced by preventing self-pollination of female parent plants (e.g., seed parents) of a first variety, permitting pollen from male parent plants of a second variety to fertilize the female parent plants, and allowing F1 hybrid seeds to form on the female plants. Self-pollination of female plants can be prevented by emasculating the flowers at an early stage of flower development. Alternatively, pollen formation can be prevented on the female parent plants using a form of male sterility. For example, male sterility can be produced by male sterility (MS), or transgenic male sterility where a transgene inhibits microsporogenesis and/or pollen formation, or self-incompatibility. Female parent plants containing MS are particularly useful. In aspects in which the female parent plants are MS, pollen may be harvested from male fertile plants and applied manually to the stigmas of MS female parent plants, and the resulting F1 seed is harvested.

Plants can be used to form single-cross tobacco F1 hybrids. Pollen from a male parent plant is manually transferred to an emasculated female parent plant or a female parent plant that is male sterile to form F1 seed. Alternatively, three-way crosses can be carried out where a single-cross F1 hybrid is used as a female parent and is crossed with a different male parent. As another alternative, double-cross hybrids can be created where the F1 progeny of two different single-crosses are themselves crossed. Self-incompatibility can be used to particular advantage to prevent self-pollination of female parents when forming a double-cross hybrid.

In an aspect, a low-nicotine or nicotine-free tobacco variety is male sterile. In another aspect, a low-nicotine or nicotine-free tobacco variety is cytoplasmic male sterile. Male sterile tobacco plants may be produced by any method known in the art. Methods of producing male sterile tobacco are described in Wernsman, E. A., and Rufty, R. C. 1987. Chapter Seventeen. Tobacco. Pages 669-698 In: Cultivar Development. Crop Species. W. H. Fehr (ed.), MacMillan Publishing Go., Inc., New York, N.Y. 761 pp.

In a further aspect, tobacco parts provided include, but are not limited to, a leaf, a stem, a root, a seed, a flower, pollen, an anther, an ovule, a pedicel, a fruit, a meristem, a cotyledon, a hypocotyl, a pod, an embryo, endosperm, an explant, a callus, a tissue culture, a shoot, a cell, and a protoplast. In an aspect, tobacco part provided does not include seed. In an aspect, this disclosure provides tobacco plant cells, tissues, and organs that are not reproductive material and do not mediate the natural reproduction of the plant. In another aspect, this disclosure also provides tobacco plant cells, tissues, and organs that are reproductive material and mediate the natural reproduction of the plant. In another aspect, this disclosure provides tobacco plant cells, tissues, and organs that cannot maintain themselves via photosynthesis. In another aspect, this disclosure provides somatic tobacco plant cells. Somatic cells, contrary to germline cells, do not mediate plant reproduction.

The provided cells, tissues and organs may be from seed, fruit, leaf, cotyledon, hypocotyl, meristem, embryos, endosperm, root, shoot, stem, pod, flower, infloresence, stalk, pedicel, style, stigma, receptacle, petal, sepal, pollen, anther, filament, ovary, ovule, pericarp, phloem, vascular tissue. In another aspect, this disclosure provides a tobacco plant chloroplast. In a further aspect, this disclosure provides epidermal cells, stomata cell, leaf or root hairs, a storage root, or a tuber. In another aspect, this disclosure provides a tobacco protoplast.

Skilled artisans understand that tobacco plants naturally reproduce via seeds, not via asexual reproduction or vegetative propagation. In an aspect, this disclosure provides tobacco endosperm. In another aspect, this disclosure provides tobacco endosperm cells. In a further aspect, this disclosure provides a male or female sterile tobacco plant, which cannot reproduce without human intervention.

In an aspect, the present disclosure provides a nucleic acid molecule comprising at least about 40%, 45%, 50%, 55%, 60%, 65%, 70%, 75%, 80%, 85%, 90%, 91%, 92%, 93%, 94%, 95%, 96%, 97%, 98%, 99%, or 100% identity to a sequence selected from the group consisting of SEQ ID NOs: 23-28, and fragments thereof. In an aspect, the present disclosure provides a polypeptide or protein comprising at least about 40%, 45%, 50%, 55%, 60%, 65%, 70%, 75%, 80%, 85%, 90%, 91%, 92%, 93%, 94%, 95%, 96%, 97%, 98%, 99%, or 100% identity to an amino acid sequence selected from the group consisting of SEQ ID NOs: 29-34. In another aspect, the present disclosure provides a biologically active variant of a protein having an amino acid sequence selected from the group consisting of SEQ ID NOs: 29-34. A biologically active variant of a protein of the present disclosure may differ from that protein by as few as 1-15 amino acid residues, as few as 10, as few as 9, as few as 8, as few as 7, as few as 6, as few as 5, as few as 4, as few as 3, as few as 2, or as few as 1 amino acid residue. Also provided are orthologous genes or proteins of genes or proteins from the ODC pathway. "Orthologs" are genes derived from a common ancestral gene and which are found in different species as a result of speciation. Orthologs may share at least 60%, 70%, 75%, 80%, 85%, 90%, 91%, 92%, 93%, 94%, 95%, 96%, 97%, 98%, 99%, or greater sequence identity or similarity at the nucleotide sequence and/or the protein sequence level. Functions of orthologs are often highly conserved among species.

As used herein, the term "sequence identity" or "identity" in the context of two polynucleotides or polypeptide sequences makes reference to the residues in the two sequences that are the same when aligned for maximum correspondence over a specified comparison window. When percentage of sequence identity is used in reference to proteins it is recognized that residue positions which are not identical often differ by conservative amino acid substitutions, where amino acid residues are substituted for other amino acid residues with similar chemical properties (e.g., charge or hydrophobicity) and therefore do not change the functional properties of the molecule. When sequences differ in conservative substitutions, the percent sequence identity may be adjusted upwards to correct for the conservative nature of the substitution. Sequences that differ by such conservative substitutions are deemed to have "sequence similarity" or "similarity."

Nucleic acid molecules, polypeptides, or proteins provided can be isolated or substantially purified. An "isolated" or "purified" nucleic acid molecule, polypeptide, protein, or biologically active portion thereof, is substantially or essentially free from components that normally accompany or interact with the polynucleotide or protein as found in its naturally occurring environment. For example, an isolated or purified polynucleotide or protein is substantially free of other cellular material, or culture medium when produced by recombinant techniques, or substantially free of chemical precursors or other chemicals when chemically synthesized.

The present disclosure further provides a method manufacturing a tobacco product comprising tobacco material from tobacco plants disclosed. In an aspect, methods comprise conditioning aged tobacco material made from tobacco plants to increase its moisture content from between about 12.5% and about 13.5% to about 21%, blending the conditioned tobacco material to produce a desirable blend. In an aspect, the method of manufacturing a tobacco product further comprises casing or flavoring the blend. Generally, during the casing process, casing or sauce materials are added to blends to enhance their quality by balancing the chemical composition and to develop certain desired flavor characteristics. Further details for the casing process can be found in *Tobacco Production, Chemistry and Technology*, Edited by L. Davis and M. Nielsen, Blackwell Science, 1999.

Tobacco material provided can be also processed using methods including, but not limited to, heat treatment (e.g., cooking, toasting), flavoring, enzyme treatment, expansion and/or curing. Both fermented and non-fermented tobaccos can be processed using these techniques. Examples of suitable processed tobaccos include dark air-cured, dark fire cured, burley, flue cured, and cigar filler or wrapper, as well as the products from the whole leaf stemming operation. In an aspect, tobacco fibers include up to 70% dark tobacco on a fresh weight basis. For example, tobacco can be conditioned by heating, sweating and/or pasteurizing steps as described in U.S. Publication Nos. 2004/0118422 or 2005/0178398.

Tobacco material provided can be subject to fermentation. Fermenting typically is characterized by high initial moisture content, heat generation, and a 10 to 20% loss of dry weight. See, e.g., U.S. Pat. Nos. 4,528,993; 4,660,577; 4,848,373; and 5,372,149. In addition to modifying the aroma of the leaf, fermentation can change either or both the color and texture of a leaf. Also during the fermentation process, evolution gases can be produced, oxygen can be taken up, the pH can change, and the amount of water retained can change. See, for example, U.S. Publication No. 2005/0178398 and Tso (1999, Chapter 1 in Tobacco, Production, Chemistry and Technology, Davis & Nielsen, eds., Blackwell Publishing, Oxford). Cured, or cured and fermented tobacco can be further processed (e.g., cut, expanded, blended, milled or comminuted) prior to incorporation into the oral product. The tobacco, in some cases, is long cut fermented cured moist tobacco having an oven volatiles content of between 48 and 50 weight percent prior to mixing with the copolymer and optionally flavorants and other additives.

In an aspect, tobacco material provided can be processed to a desired size. In an aspect, tobacco fibers can be processed to have an average fiber size of less than 200 micrometers. In an aspect, tobacco fibers are between 75 and 125 micrometers. In another aspect, tobacco fibers are processed to have a size of 75 micrometers or less. In an aspect, tobacco fibers include long cut tobacco, which can be cut or shredded into widths of about 10 cuts/inch up to about 110 cuts/inch and lengths of about 0.1 inches up to about 1 inch. Double cut tobacco fibers can have a range of particle sizes such that about 70% of the double cut tobacco fibers falls between the mesh sizes of −20 mesh and 80 mesh.

Tobacco material provided can be processed to have a total oven volatiles content of about 10% by weight or greater; about 20% by weight or greater; about 40% by weight or greater; about 15% by weight to about 25% by weight; about 20% by weight to about 30% by weight; about 30% by weight to about 50% by weight; about 45% by weight to about 65% by weight; or about 50% by weight to about 60% by weight. Those of skill in the art will appreciate that "moist" tobacco typically refers to tobacco that has an oven volatiles content of between about 40% by weight and about 60% by weight (e.g., about 45% by weight to about 55% by weight, or about 50% by weight). As used herein, "oven volatiles" are determined by calculating the percentage of weight loss for a sample after drying the sample in a pre-warmed forced draft oven at 110° C. for 3.25 hours. The oral product can have a different overall oven volatiles content than the oven volatiles content of the tobacco fibers used to make the oral product. The processing steps described can reduce or increase the oven volatiles content.

Having now generally described the disclosure, the same will be more readily understood through reference to the following examples that are provided by way of illustration, and are not intended to be limiting of the present disclosure, unless specified.

The following are exemplary embodiments of the present disclosure.

Embodiment 1

A tobacco plant comprising an inducible promoter operably linked to a transcribable DNA sequence encoding a non-coding RNA for suppression of an ornithine decarboxylase (ODC) gene.

Embodiment 2

The tobacco plant of Embodiment 1, wherein said tobacco plant comprises a mutation or a transgene conferring a reduced level of nicotine.

Embodiment 3

The tobacco plant of Embodiments 1 or 2, wherein said tobacco plant is a low-alkaloid tobacco plant.

Embodiment 4

The tobacco plant of any one of Embodiments 1-3, wherein said tobacco plant comprises a nic1 mutation, a nic2 mutation, or both.

Embodiment 5

The tobacco plant of any one of Embodiments 1-4, wherein said tobacco plant comprises a mutation in a gene or locus encoding a protein selected from the group consisting of aspartate oxidase, agmatine deiminase (AIC), arginase, diamine oxidase, arginine decarboxylase (ADC), methylputrescine oxidase (MPO), NADH dehydrogenase, ornithine decarboxylase (ODC), phosphoribosylanthranilate isomerase (PRAI), putrescine N-methyltransferase (PMT), quinolate phosphoribosyl transferase (QPT), S-adenosyl-methionine synthetase (SAMS), A622, NBB1, BBL, MYC2, Nic1, Nic2, ethylene response factor (ERF) transcription factor, nicotine uptake permease (NUP), and MATE transporter.

Embodiment 6

The tobacco plant of any one of Embodiments 1-5, wherein said tobacco plant comprises a mutation in a gene or locus encoding a protein selected from the group consisting of ERF32, ERF34, ERF39, ERF189, ERF115, ERF221, ERF104, ERF179, ERF17, and ERF168.

Embodiment 7

The tobacco plant of any one of Embodiments 1-6, wherein said tobacco plant comprises a transgene targeting and suppressing a gene encoding a protein selected from the group consisting of aspartate oxidase, agmatine deiminase (AIC), arginase, diamine oxidase, arginine decarboxylase (ADC), methylputrescine oxidase (MPO), NADH dehydrogenase, ornithine decarboxylase (ODC), phosphoribosylanthranilate isomerase (PRAI), putrescine N-methyltransferase (PMT), quinolate phosphoribosyl transferase (QPT), S-adenosyl-methionine synthetase (SAMS), A622, NBB1, BBL, MYC2, Nic1, Nic2, ethylene response factor (ERF) transcription factor, nicotine uptake permease (NUP), and MATE transporter.

Embodiment 8

The tobacco plant of any one of Embodiments 1-7, wherein said tobacco plant comprises a transgene targeting and suppressing a gene encoding a protein selected from the group consisting of ERF32, ERF34, ERF39, ERF189, ERF115, ERF221, ERF104, ERF179, ERF17, and ERF168.

Embodiment 9

The tobacco plant of any one of Embodiments 1-8, wherein said tobacco plant is capable of producing a leaf comprising a comparable level of one or more polyamines relative to a comparable leaf of a control plant not comprising said mutation or said transgene.

Embodiment 10

The tobacco plant of any one of Embodiments 1-9, wherein said comparable level is within 20%, 17.5%, 15%, 12.5%, 10%, 7.5%, 5%, 2.5%, or 1% of the level in said control.

Embodiment 11

The tobacco plant of any one of claims Embodiments 1-10, wherein said tobacco plant is capable of producing a leaf comprising a comparable chlorophyll level relative to a comparable leaf of a control plant not comprising said mutation or said transgene.

Embodiment 12

The tobacco plant of any one of Embodiments 1-11, wherein said comparable chlorophyll level is within 20%, 17.5%, 15%, 12.5%, 10%, 7.5%, 5%, 2.5%, or 1% of the level in said control.

Embodiment 13

The tobacco plant of any one of Embodiments 1-12, wherein said tobacco plant is capable of producing a leaf comprising a comparable number of mesophyll cell per unit of leaf area relative to a comparable leaf of a control plant not comprising said mutation or said transgene.

Embodiment 14

The tobacco plant of any one of Embodiments 1-13, wherein said comparable mesophyll cell per unit of leaf area is within 20%, 17.5%, 15%, 12.5%, 10%, 7.5%, 5%, 2.5%, or 1% of the level in said control.

Embodiment 15

The tobacco plant of any one of Embodiments 1-14, wherein said tobacco plant is capable of producing a leaf comprising a comparable epidermal cell size relative to a comparable leaf of a control plant not comprising said mutation or said transgene.

Embodiment 16

The tobacco plant of any one of Embodiments 1-15, wherein said comparable epidermal cell size is within 20%, 17.5%, 15%, 12.5%, 10%, 7.5%, 5%, 2.5%, or 1% of the level in said control.

Embodiment 17

The tobacco plant of any one of Embodiments 1-16, wherein said tobacco plant comprises a comparable leaf yield relative to a comparable leaf of a control plant not comprising said mutation or said transgene.

Embodiment 18

The tobacco plant of any one of Embodiments 1-17, wherein said comparable leaf yield is within 20%, 17.5%, 15%, 12.5%, 10%, 7.5%, 5%, 2.5%, or 1% of the level in said control.

Embodiment 19

The tobacco plant of any one of Embodiments 1-18, wherein said tobacco plant exhibits a comparable insect herbivory susceptibility relative to a comparable leaf of a control plant not comprising said mutation or said transgene.

Embodiment 20

The tobacco plant of any one of Embodiments 1-19, wherein said ornithine decarboxylase (ODC) gene encodes a polypeptide sequence having at least 80%, at least 85%, at least 90%, at least 95%, at least 97%, at least 99%, or 100% identity to a sequence selected from the group consisting of SEQ ID Nos: 29-34.

Embodiment 21

The tobacco plant of any one of Embodiments 1-20, wherein said ODC gene comprises a nucleotide sequence having at least 90%, at least 95%, at least 97%, at least 99%, or 100% identity to a sequence selected from the group consisting of SEQ ID Nos: 23-28.

Embodiment 22

The tobacco plant of any one of Embodiments 1-21, wherein said inducible promoter is a topping-inducible promoter.

Embodiment 23

The tobacco plant of any one of Embodiments 1-22, wherein said inducible promoter is also a tissue-specific or tissue-preferred promoter.

Embodiment 24

The tobacco plant of any one of Embodiments 1-23, wherein said tissue-specific or tissue-preferred promoter is specific or preferred for one or more tissues or organs selected from the group consisting of shoot, root, leaf, stem, flower, sucker, root tip, mesophyll cells, epidermal cells, and vasculature.

Embodiment 25

The tobacco plant of any one of Embodiments 1-24, wherein said inducible promoter regulates root specific or preferred expression.

Embodiment 26

The tobacco plant of any one of Embodiments 1-25, wherein said inducible promoter comprises a sequence selected from the group consisting of SEQ ID Nos: 1-11.

Embodiment 27

The tobacco plant of any one of Embodiments 1-26, wherein said inducible promoter regulates leaf specific or preferred expression.

Embodiment 28

The tobacco plant of any one of Embodiments 1-27, wherein said inducible promoter comprises a sequence selected from the group consisting of SEQ ID Nos: 12-21.

Embodiment 29

The tobacco plant of any one of Embodiments 1-28, wherein said inducible promoter is a heterologous to said transcribable DNA sequence.

Embodiment 30

The tobacco plant of any one of Embodiments 1-29, wherein said non-coding RNA is selected from the group consisting of microRNA (miRNA), anti-sense RNA, small interfering RNA (siRNA), a trans-acting siRNA (ta-siRNA), and hairpin RNA (hpRNA).

Embodiment 31

The tobacco plant of any one of Embodiments 1-30, wherein said non-coding RNA comprises a nucleotide sequence having at least 90%, at least 95%, at least 97%, at least 99%, or 100% identity to a sequence selected from the group consisting of SEQ ID Nos: 35 and 36.

Embodiment 32

The tobacco plant of any one of Embodiments 1-31, wherein said non-coding RNA is provided in an ODC RNAi construct comprising a nucleotide sequence having at least 90% identity to SEQ ID No: 22.

Embodiment 33

A tobacco plant, or part thereof, comprising a nic1 mutation, a nic2 mutation, or both, and further comprising a transgene or mutation providing an early-senescence trait.

Embodiment 34

The tobacco plant of Embodiment 33, wherein said mutation providing an early-senescence trait is yellow burley1 (−yb1).

Embodiment 35

The tobacco plant of Embodiments 33 or 34, wherein said mutation providing an early-senescence trait is yellow burley2 (−yb2).

Embodiment 36

The tobacco plant of any one of Embodiments 33-35, wherein said mutation providing an early-senescence trait is pale yellow (PY).

Embodiment 37

A tobacco plant, or part thereof, comprising relative to a control tobacco plant:

a. a first genome modification providing a lower level of nicotine or total alkaloid, and
b. a second genome modification providing a comparable level of one or more traits selected from the group consisting of
 i. total leaf polyamine level,
 ii. total root polyamine level,
 iii. total leaf chlorophyll level,
 iv. mesophyll cell number per leaf area unit, and
 v. leaf epidermal cell size; and wherein said control plant does not have both said first and said second genome modifications.

Embodiment 38

A tobacco plant, or part thereof, comprising relative to a control tobacco plant:

a. a first genome modification providing a lower level of nicotine or total alkaloid, and
b. a second genome modification providing a comparable level of total leaf polyamine level, wherein said control plant does not have both said first and said second genome modifications.

Embodiment 39

A tobacco plant, or part thereof, comprising relative to a control tobacco plant:

a. a first genome modification providing a lower level of nicotine or total alkaloid, and
b. a second genome modification providing a comparable level of total root polyamine level, wherein said control plant does not have both said first and said second genome modifications.

Embodiment 40

A tobacco plant, or part thereof, comprising relative to a control tobacco plant:

a. a first genome modification providing a lower level of nicotine or total alkaloid, and
b. a second genome modification providing a comparable level of total leaf chlorophyll level, wherein said control plant does not have both said first and said second genome modifications.

Embodiment 41

A tobacco plant, or part thereof, comprising relative to a control tobacco plant:

a. a first genome modification providing a lower level of nicotine or total alkaloid, and
b. a second genome modification providing a comparable level of mesophyll cell number per leaf area unit, wherein said control plant does not have both said first and said second genome modifications.

Embodiment 42

A tobacco plant, or part thereof, comprising relative to a control tobacco plant:

a. a first genome modification providing a lower level of nicotine or total alkaloid, and
b. a second genome modification providing a comparable level of leaf epidermal cell size, wherein said control plant does not have both said first and said second genome modifications.

Embodiment 43

The tobacco plant, or part thereof, of any one of Embodiments 37-42, wherein said tobacco plant comprises a reduced amount of total conjugated polyamines in leaves relative to said control tobacco plant.

Embodiment 44

The tobacco plant, or part thereof, of any one of Embodiments 37-43, wherein said tobacco plant comprises a reduced amount of total conjugated polyamines in roots relative to said control tobacco plant.

Embodiment 45

The tobacco plant, or part thereof, of any one of Embodiments 37-44, wherein said tobacco plant comprises a reduced amount of total free polyamines in leaves relative to said control tobacco plant.

Embodiment 46

The tobacco plant, or part thereof, of any one of Embodiments 37-45, wherein said tobacco plant comprises a reduced amount of total conjugated polyamines in roots relative to said control tobacco plant.

Embodiment 47

The tobacco plant, or part thereof, of any one of Embodiments 37-46, wherein said tobacco plant comprises a reduced amount of total conjugated form of one or more polyamines selected from the group consisting of putrescine, spermidine and spermine in leaves relative to said control tobacco plant.

Embodiment 48

The tobacco plant, or part thereof, of any one of Embodiments 37-47, wherein said tobacco plant comprises a reduced amount of total conjugated form of one or more polyamines selected from the group consisting of putrescine, spermidine and spermine in roots relative to said control tobacco plant.

Embodiment 49

The tobacco plant, or part thereof, of any one of Embodiments 37-48, wherein said tobacco plant comprises a reduced amount of total free form of one or more polyamines selected from the group consisting of putrescine, spermidine and spermine in leaves relative to said control tobacco plant.

Embodiment 50

The tobacco plant, or part thereof, of any one of Embodiments 37-49, wherein said tobacco plant comprises a reduced amount of total conjugated form of one or more polyamines selected from the group consisting of putrescine, spermidine and spermine in roots relative to said control tobacco plant.

Embodiment 51

The tobacco plant, or part thereof, of any one of Embodiments 37-50, wherein said first genome modification provides a lower level of nicotine compared to said control tobacco plant.

Embodiment 52

The tobacco plant, or part thereof, of any one of Embodiments 37-51, said first genome modification, said second genome modification, or both comprise a transgene, a mutation, or both.

Embodiment 53

The tobacco plant, or part thereof, of any one of Embodiments 37-52, said first genome modification, said second genome modification, or both comprise a transgene.

Embodiment 54

The tobacco plant, or part thereof, of any one of Embodiments 37-53, said first genome modification, said second genome modification, or both comprise a mutation.

Embodiment 55

The tobacco plant, or part thereof, of any one of Embodiments 37-54, said first genome modification, said second genome modification, or both are not transgene-based.

Embodiment 56

The tobacco plant, or part thereof, of any one of Embodiments 37-55, said first genome modification, said second genome modification, or both are not mutation-based.

Embodiment 57

The tobacco plant, or part thereof, of any one of Embodiments 37-56, wherein said first genome modification comprises a nic1 mutation, a nic2 mutation, or both.

Embodiment 58

The tobacco plant, or part thereof, of any one of Embodiments 37-57, wherein said first genome modification comprises a transgene targeting the Nic1 locus, a transgene targeting the Nic2 locus, or both.

Embodiment 59

The tobacco plant, or part thereof, of any one of Embodiments 37-58, wherein said second genome modification comprises a transcribable DNA sequence encoding a non-coding RNA for suppression of an ornithine decarboxylase (ODC) gene, a MYB8 gene, or both.

Embodiment 60

The tobacco plant, or part thereof, of any one of Embodiments 37-59, wherein said a transcribable DNA sequence is operably linked to an heterologous promoter selected from the group consisting of a constitutive promoter, a developmental promoter, a tissue-specific promoter, a tissue-preferred promoter, an inducible promoter, and any combination thereof.

Embodiment 61

The tobacco plant, or part thereof, of any one of Embodiments 37-60, wherein said second genome modification comprises overexpression of an diamine oxidase, suppression of an arginine decarboxylase, or both.

Embodiment 62

The tobacco plant, or part thereof, of any one of Embodiments 37-61, wherein said first genome modification comprises a mutation in a gene or locus encoding a protein selected from the group consisting of aspartate oxidase, agmatine deiminase (AIC), arginase, diamine oxidase, arginine decarboxylase (ADC), methylputrescine oxidase (MPO), NADH dehydrogenase, ornithine decarboxylase (ODC), phosphoribosylanthranilate isomerase (PRAI), putrescine N-methyltransferase (PMT), quinolate phosphoribosyl transferase (QPT), and S-adenosyl-methionine synthetase (SAMS), A622, NBB1, BBL, MYC2, Nic1, Nic2, ethylene response factor (ERF) transcription factor, nicotine uptake permease (NUP), and MATE transporter.

Embodiment 63

The tobacco plant, or part thereof, of any one of Embodiments 37-62, wherein said first genome modification comprises a mutation in a gene or locus encoding a protein selected from the group consisting of ERF32, ERF34, ERF39, ERF189, ERF115, ERF221, ERF104, ERF179, ERF17, and ERF168.

Embodiment 64

The tobacco plant, or part thereof, of any one of Embodiments 37-63, wherein said first genome modification comprises a transgene targeting and suppressing a gene or locus encoding a protein selected from the group consisting of aspartate oxidase, agmatine deiminase (AIC), arginase, diamine oxidase, arginine decarboxylase (ADC), methylputrescine oxidase (MPO), NADH dehydrogenase, ornithine decarboxylase (ODC), phosphoribosylanthranilate isomerase (PRAI), putrescine N-methyltransferase (PMT), quinolate phosphoribosyl transferase (QPT), and S-adenosyl-methionine synthetase (SAMS), A622, NBB1, BBL, MYC2, Nic1, Nic2, ethylene response factor (ERF) transcription factor, nicotine uptake permease (NUP), and MATE transporter.

Embodiment 65

The tobacco plant, or part thereof, of any one of Embodiments 37-64, wherein said first genome modification comprises a transgene targeting and suppressing a gene or locus encoding a protein selected from the group consisting of ERF32, ERF34, ERF39, ERF189, ERF115, ERF221, ERF104, ERF179, ERF17, and ERF168.

Embodiment 66

The tobacco plant, or part thereof, of any one of Embodiments 37-65, wherein said lower level is measured at a time selected from the group consisting of immediately before flowering, at topping, 1 week-post-topping (WPT), 2 WPT, 3 WPT, 4 WPT, 5 WPT, 6 WPT, 7 WPT, 8 WPT, and at harvest.

Embodiment 67

The tobacco plant, or part thereof, of any one of Embodiments 37-66, wherein said comparable level is measured at a time selected from the group consisting of immediately before flowering, at topping, 1 week-post-topping (WPT), 2 WPT, 3 WPT, 4 WPT, 5 WPT, 6 WPT, 7 WPT, 8 WPT, and at harvest.

Embodiment 68

The tobacco plant, or part thereof, of any one of Embodiments 37-67, wherein said tobacco plant is capable of producing a leaf with a leaf grade comparable to that of a leaf from said control plant.

Embodiment 69

The tobacco plant, or part thereof, of any one of Embodiments 37-68, wherein said tobacco plant has a total leaf yield comparable to said control plant.

Embodiment 70

The tobacco plant, or part thereof, of any one of the preceding Embodiments, wherein said tobacco plant comprises a nicotine level selected from the group consisting of less than 3%, less than 2.75%, less than 2.5%, less than 2.25%, less than 2.0%, less than 1.75%, less than 1.5%, less than 1.25%, less than 1%, less than 0.9%, less than 0.8%, less than 0.7%, less than 0.6%, less than 0.5%, less than 0.4%, less than 0.3%, less than 0.2%, less than 0.1%, and less than 0.05%.

Embodiment 71

The tobacco plant, or part thereof, of any one of Embodiments 37-70, wherein said tobacco plant comprises nicotine at a level below 1%, below 2%, below 5%, below 8%, below 10%, below 12%, below 15%, below 20%, below 25%, below 30%, below 40%, below 50%, below 60%, below 70%, or below 80% of the nicotine level of said control plant when grown in comparable growth conditions.

Embodiment 72

A population of the tobacco plants of any one of the preceding Embodiments.

Embodiment 73

Cured tobacco material from the tobacco plant of any one of the preceding Embodiments.

Embodiment 74

The cured tobacco material of Embodiment 73, wherein said cured tobacco material is made by a curing process selected from the group consisting of flue curing, air curing, fire curing, and sun curing.

Embodiment 75

A tobacco blend comprising said cured tobacco material of Embodiments 73 or 74.

Embodiment 76

The tobacco blend of any one of Embodiments 73-75, wherein said cured tobacco material constitutes about at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, or at least 95% of cured tobacco in said tobacco blend by weight.

Embodiment 77

The tobacco blend of any one of Embodiments 73-76, wherein said cured tobacco material constitutes about at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, or at least 95% of cured tobacco in said tobacco blend by volume.

Embodiment 78

A tobacco product comprising the cured tobacco material of any one of Embodiments 73-77.

Embodiment 79

The tobacco product of Embodiment 78, wherein said tobacco product is selected from the group consisting of a cigarette, a cigarillo, a non-ventilated recess filter cigarette, a vented recess filter cigarette, a cigar, snuff, pipe tobacco, cigar tobacco, cigarette tobacco, chewing tobacco, leaf tobacco, shredded tobacco, and cut tobacco.

Embodiment 80

The tobacco product of Embodiments 78 or 79, wherein said tobacco product is selected from the group consisting of loose leaf chewing tobacco, plug chewing tobacco, moist snuff, and nasal snuff.

Embodiment 81

A method for improving leaf quality in a reduced-alkaloid tobacco plant, said method comprising:

a. Growing a tobacco plant;

b. Reducing the level of putrescine in said tobacco plant, c. Harvesting leaves from said tobacco plant.

Embodiment 82

A method for improving leaf quality in a reduced-alkaloid tobacco plant, said method comprising:

a. Growing a tobacco plant;

b. Suppressing the expression or activity of an ornithine decarboxylase (ODC) gene in said tobacco plant, c. Harvesting leaves from said tobacco plant.

Embodiment 83

The method of Embodiment 81 or 82, wherein said suppressing is within 2, 4, 6, or 8 WPT.

Embodiment 84

The method of any one of Embodiments 81-83, wherein said suppressing comprises suppressing said ODC gene both prior to and after topping said tobacco plant.

Embodiment 85

The method of any one of Embodiments 82-84, wherein said suppressing does not include the use of a chemical inhibitor.

Embodiment 86

The method of any one of Embodiments 82-85, wherein said suppressing comprises applying an ODC inhibitor to said tobacco plant.

Embodiment 87

The method of any one of Embodiments 82-86, wherein said suppressing is by applying an ODC inhibitor to said tobacco plant.

Embodiment 88

The method of any one of Embodiments 82-87, wherein said ODC inhibitor is DFMO.

Embodiment 89

The method of any one of Embodiments 82-88, wherein said suppressing is by inducing the expression of a non-coding RNA for suppression of said ornithine decarboxylase (ODC) gene.

Embodiment 90

The method of any one of Embodiments 82-89, wherein said method further comprises reducing nitrogen fertilization or reducing nitrate.

EXAMPLES

Example 1: Plant Material and General Growth Conditions

Seeds of *Nicotiana tabacum* L. cv. Burley 21 wild-type NA, as well as HI (nic2), LI (nic1) and LA (nic1nic2) near-isogenic varieties were obtained from the US *Nicotiana* Germplasm Collection at North Carolina State University and used in all greenhouse experiments. Seeds were germinated in pots under greenhouse conditions at 27/23° C. day/night temperature and a 16-h photoperiod (~200 mmol $s^{-1}$ $m^{-2}$; λ=400-700 nm) at 70% relative humidity. Five week-old tobacco plantlets were transferred to 13-L pots with standard substrate (Einheitserde, Frondenberg, Germany). The plants were attached to a continuous drip irrigation system active every 4 h for ~5 min and were irrigated with 0.7% (w/v) Ferty 2 Mega containing 16% nitrogen, (Planta Diingemittel, Regenstauf, Germany) for 5 min $h^{-1}$ during the 16-h photoperiod and grown for 4 additional weeks. Greenhouse plants were topped when 50% of the plants had at least one open flower. After topping, plants grew for additional 4-7 weeks until harvest, 30 days post-topping. Tobacco leaves used for polyamine analysis were collected from greenhouse-grown plants at three time points: before flowering (6.5-week-old plants), just before topping, i.e. the removal of the floral apex (9-week-old plants) and at harvest (13-week-old plants, 4 weeks post-topping). Root samples were collected at topping and harvest. LA and NA tobacco plants were grown in the field under 135 units of nitrogen per acre and sampled at 1 week post-topping for polyamine analysis.

For treatment with polyamine biosynthesis inhibitors, 5 mM D-Arginine (AKos, Steinen, Germany), 2 mM DFMO (Synchem Ug & Co. KG, Felsberg, Germany) alone or in combination with 0.5 mM Ethephon®, or 0.5 mM Ethephon® alone (Merck KGaA, Darmstadt, Germany), were diluted in the same amount of water used for daily irrigation and applied to LA plants every 4 hours at 9 am, 12 am, 3 pm and 6 pm three times per week instead of the drip irrigation system. The treatment with D-arginine and DFMO started before flowering (~2.5 weeks before topping when plants were still in the vegetative growth stage) for a period of 6 weeks until harvest, whereas Ethephon® was applied from topping to harvest (4 weeks in total) to avoid early senescence in the LA plants. Twelve plants per inhibitor were treated. NA plants were used as controls and treated in the same way as the LA plants. More description of experimental procedures and data can be found at Nölke G, et al. Polyamines delay leaf maturation in low-alkaloid tobacco varieties. *Plant Direct.* 2018:2:1-12.

Example 2: Chlorophyll Measurements

Chlorophyll contents were determined by measuring leaf absorbance in the red and infrared regions using a SPAD- 502 Plus device (Minolta Camera Co., Osaka, Japan). Chlorophyll was measured twice in the same day at different positions in all fully expanded (length >15 cm) leaves (leaves 6-26) from six randomly-selected plants from each line at five growth stages: before flowering (6.5-week-old plants and 2.5 weeks before topping), at topping, 1 and 2.5 WPT and at harvest (30 days post topping) before flowering. The total chlorophyll content was calculated as an average of all measured leaf chlorophyll values per plant to minimize the influence of leaf position.

Example 3: Leaf Cell Microscopy

Four leaf discs (1 $cm^2$) cut form leaf 15 from six biological replicates at different development stages (before flowering, at topping, 1 WPT and at harvest) were mounted on slides and imaged using a Leica DM R microscope (Leica, Wetzlar, Germany) with a 10× air objective. Images were imported into ImageJ and Adobe Photoshop CS5.1 software and the cells per unit area were counted using Count Tool in the Photoshop CS5. A standard area was designated to use for cell counting three times across all images and care was taken to avoid counting any cell twice.

Example 4: Determination of ODC and ADC Activities

To determine enzymatic activities, 500 mg of tobacco leaf tissue collected from leaf 23 of three biological replicates of was ground in 1 ml HEPES extraction buffer (100 mM HEPES, 2 mM dithiothreitol (DTT), 1 mM EDTA, pH 7.5) and 100 mg of polyvinylpyrrolidone was added during grinding. Following centrifugation (13,000 g, 10 min, 4° C.), the enzyme activities were measured using an isotopic method as described by Capell et al. (1998) by measuring the release of $^{14}CO_2$. L-[1-$^{14}$C]Arg and L[1-$^{14}$C]Orn were used as radioactive substrates.

Example 5: Polyamine Extraction and Analysis

For polyamine analysis, 150 µg of leaf or root material was harvested from plants grown in the greenhouse at different stages of development: before flowering (leaves 6 and 12, numbered from base), at topping (leaves 19 and 23 and roots) and at harvest (leaves 23 and 24 and roots). Samples were collected after 4 h of illumination from three biological replicates and were flash frozen in liquid nitrogen. For field-grown plants, leaf material was collected from five well-expanded upper leaves from three biological replicates. Plant material was ground in 1.6 ml pre-chilled 10% (v/v) perchloric acid and incubated at 4° C. for 1 h. The extract was vortexed for 10 s and centrifuged (16,000 g, 15 min, 4° C.) before 800 µl of the supernatant was mixed with 100 µl 1 mM hexamethylenediamine. Then, 10 µl of the clear supernatant was transferred to a fresh 2-ml tube and polyamines were extracted with 200 µl of cyclohexane for the dansilation of free polyamines. For the extraction of conjugated polyamines, the pellet was resuspended in 1600 µl 1 M NaOH and 200 µl 1 mM hexamethylenediamine and centrifuged as above. The clear supernatant (200 µl) was transferred to a 2-ml glass ampule containing 12 M HCl, mixed and incubated for 16 h at 110° C. overnight for the hydrolysis of conjugated polyamines. The dansilation of free and conjugated polyamines was carried out with dansyl chloride as described by Flores and Galston (1982).

The dansylated polyamines were measured by LC-MS/MS. All experiments were carried out on a 3200 QTRAP™ mass spectrometer (Sciex, Darmstadt, Germany) coupled to an HPLC Agilent 1200 system (Waldbronn, Germany). The mass spectrometer was equipped with an electrospray ionization source. The sample was separated on a reversed-phase Synergi Fusion with 80 Å pore size, 4 µm particle size and dimensions of 50 mm×2.0 mm internal diameter (Phenomenex, Aschaffenburg, Germany) with the corresponding guard column at a flow rate of 800 µl/min. The column oven was heated to 30° C. For elution, solvent A comprised 94.9% (v/v) water, 5% (v/v) acetonitrile, 0.1% (v/v) formic acid and solvent B comprised 94.9% (v/v) acetonitrile, 5% (v/v) water, 0.1% (v/v) formic acid. The elution following elution profiles was used: 1 min, hold at 60% solvent A/40% solvent B; 3 min, linear increase to 100% solvent B, 3 min hold at 100% solvent B; rapid linear decrease to 60% solvent A/40% solvent B in 0.1 min; hold for 1 min. The total run time was 8 min and the sample volume injected in each run was 10 µl.

The mass spectrometer was set to unit resolution in Q1 and Q3. All measurements were captured in multiple reaction monitoring mode. For compound optimization, standards were prepared according to the dansylation protocol, diluted in 50:50 (v/v) methanol/water and infused with a flow rate of 10 µl/min with the syringe pump directly connected to the ion source. Declustering potential, collision energy, collision cell entrance potential, collision cell exit potential and entrance potential were optimized for all compounds using automated compound optimization (Table 3). The ion source parameters were set to: capillary voltage=5.5 kV, heater gas temperature=500° C., curtain gas=30 psi, nebulizing gas=70 psi, drying gas=70 psi, and collision gas=medium. For each analyte, one transition was used for quantification and another as a qualifier. The acquired data was processed using Analyst v1.6 (Sciex). The mass calibration of the 3200 QTRAP was achieved using polypropylene glycol standards (Standards Chemical Kit with Low/High Concentration PPGs, Sciex) according to the manufacturer's instructions.

TABLE 3

Compound parameter for polyamine quantification.

| Dansylated Compound | Quantifier/ Qualifier | Parent mass [m/z] | Product mass [m/z] | DP [eV] | EP [eV] | CEP [eV] | CE [eV] | CXP [eV] | RT [min] |
|---|---|---|---|---|---|---|---|---|---|
| Spermine | Quantifier | 1135.39 | 360.3 | 86 | 10 | 48 | 65 | 4 | 4.3 |
| Spermine | Qualifier | 1135.39 | 170.3 | 86 | 10 | 48 | 121 | 4 | 4.3 |
| Spermidine | Quantifier | 845.228 | 360.3 | 96 | 9.5 | 34 | 53 | 4 | 3.9 |
| Spermidine | Qualifier | 845.228 | 170.3 | 96 | 9.5 | 34 | 81 | 4 | 3.9 |
| Putrescine | Quantifier | 555.119 | 170.3 | 61 | 7.5 | 24 | 45 | 4 | 3.2 |
| Putrescine | Qualifier | 555.119 | 168.3 | 61 | 7.5 | 24 | 79 | 4 | 3.2 |

TABLE 3-continued

| Compound parameter for polyamine quantification. | | | | | | | | | |
|---|---|---|---|---|---|---|---|---|---|
| Dansylated Compound | Quantifier/ Qualifier | Parent mass [m/z] | Product mass [m/z] | DP [eV] | EP [eV] | CEP [eV] | CE [eV] | CXP [eV] | RT [min] |
| Hexamethyldiamine | Quantifier | 583.14 | 170.3 | 70 | 10 | 28.809 | 50 | 4 | 3.5 |
| Hexamethyldiamine | Qualifier | 583.14 | 169.2 | 70 | 10 | 28.809 | 50 | 4 | 3.5 |

DP = declustering potential,
CE = collision energy,
CEP = collision cell entrance potential,
CXP = collision cell exit potential,
EP = entrance potential.

Example 6: Statistical Analysis

Differences between the genotypes were determined by applying one-way analysis of variance (ANOVA) followed by post-hoc Bonferroni test using Excel software (Microsoft, Redmond, Wash., USA). Two-tailed t-tests were applied. A p-value <0.05 was considered statistically significant.

Figure 1B:
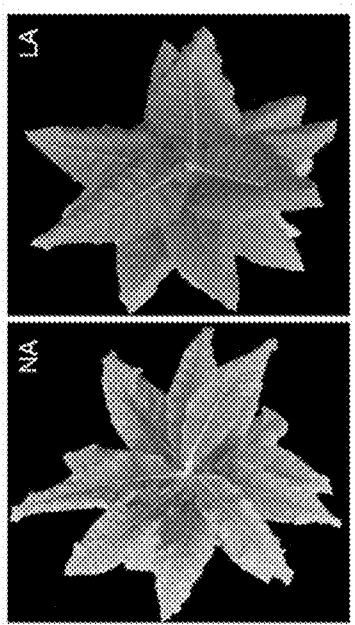
FIG. 1B: Representative photos of NA and LA plants at harvest.

Example 7: Biochemical and Morphological Differences Among the Four Varieties During Leaf Ripening Progression of senescence in the Burley 21 NA, HI, LI and LA lines was monitored by measuring the loss of chlorophyll a and b in the leaves. The chlorophyll levels had declined significantly ($p<0.01$) in all genotypes after 1 week post-topping (WPT) (FIG. 1A). However, the leaves of the LI and LA plants contained significantly ($p<0.001$) higher levels of chlorophyll than the NA controls at 2.5 WPT (22% more in both genotypes) and at harvest (36% and 44% more in the LI and LA leaves, respectively), indicating slower chlorophyll degradation compared to NA controls. Loss of chlorophyll was correlated with morphological changes in the leaves of NA plants, i.e. they became wrinkly and leathery with yellow patches, whereas the LA leaves remained smooth, shiny and green (FIG. 1B).

Figure 1C:
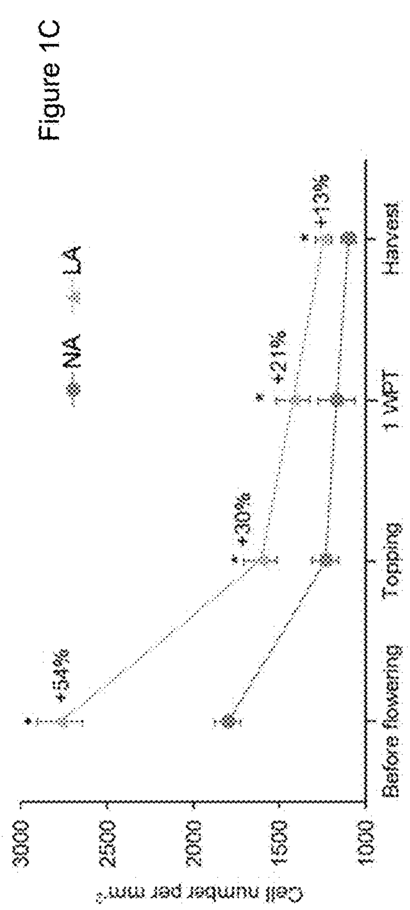
FIG. 1C: Time-course evaluation of mesophyll cell number in leaf 15.
Figure 1D:
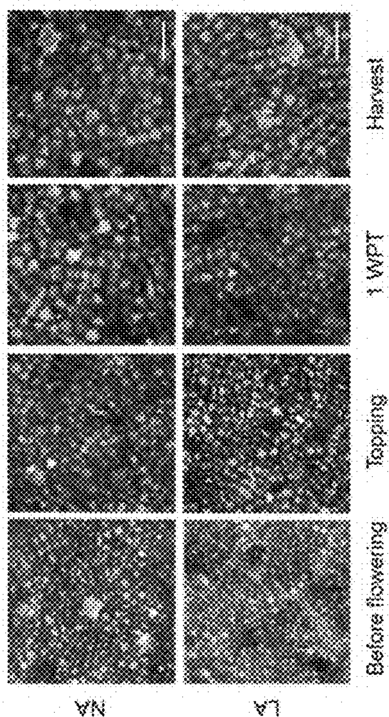
FIG. 1D: Microscopic images of mesophyll cells of leaf 15 from NA and LA plants at different plant developmental stages. Bar=100 μm. Values in A and C are means of six biological replicates. Error bars represent standard deviations of the mean. Statistical difference to NA is shown: *p<0.05.

Given the distinct leaf morphology in the LA and NA lines, the size and shape of the mesophyll cells were investigated at different time points. Before flowering, leaf 15 (numbered from the base) of the LA plants had smaller and more abundant mesophyll cells (more cells per unit leaf area) compared to the NA plants (FIG. 1C/D). From that time point until harvest, the number of leaf mesophyll cells per unit area declined at a similar rate in both the NA and LA lines, but the LA plants retained a significantly ($p<0.05$) greater number of mesophyll cells throughout ripening. The greatest difference in mesophyll cell number per unit area (54% more cells in the LA plants compared to NA controls) was observed at earlier stages of leaf development (before flowering). LI plants also contained more mesophyll cells than the NA plants but not to the degree observed in the LA plants, and there was no significant difference in mesophyll cell number between the HI and NA lines (data not shown).

Example 8: LA Plants Accumulate Higher Levels of Polyamines than NA Plants

Figure 2A:
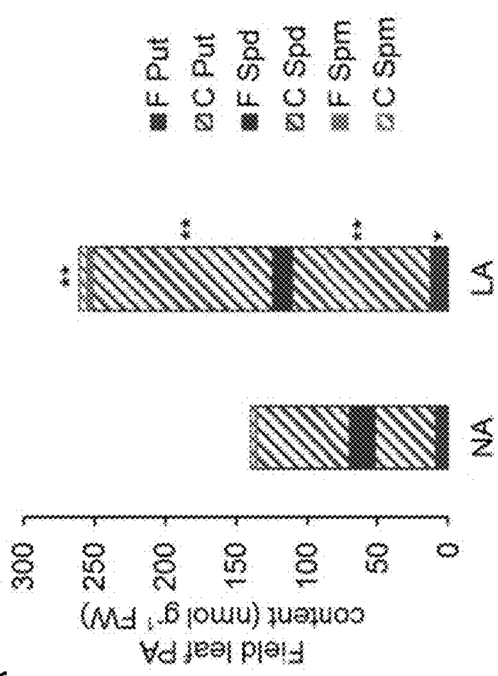
FIG. 2A: Free (F) and conjugated (C) putrescine (Put), spermidine (Spd) and spermine (Spm) content from five well-expanded upper leaves of NA and LA plants (three biological replicates grown in the field) 1 week after topping.

To investigate the impact of the nic1nic2 double mutation on polyamine biosynthesis, the levels of free and conjugated putrescine, spermidine and spermine in the NA and LA plants were compared by liquid chromatography tandem mass spectrometry (LC-MS/MS). First, the polyamine content were analyzed in leaves 16-18 of field-grown plants. At 1 WPT, the total polyamine content was significantly higher (1.9-fold, $p<0.001$) in the LA plants compared to the NA plants (FIG. 2A). Compositional analysis revealed significantly higher levels of free putrescine (1.4-fold, $p<0.05$), conjugated putrescine (2.3-fold, $p<0.005$) and conjugated spermidine (1.9-fold, ($p<0.005$) levels in the leaves of the LA plants, indicating that the polyamine biosynthesis pathway is strongly induced by the nic1nic2 double mutant or that the inability of the substrates to be further processed into nicotine results in a buildup of these materials. In contrast, the level of free spermidine in the LA plants was lower than in the NA plants, although the difference was not statistically significant ($p>0.05$).

Figure 2B:
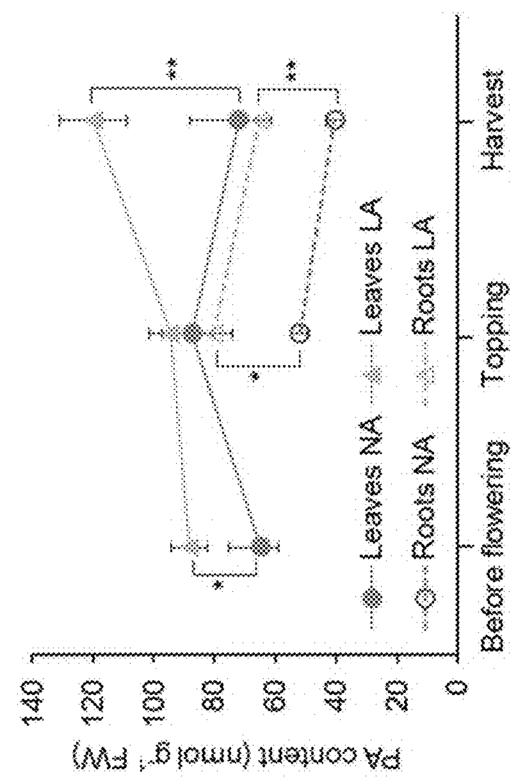
FIG. 2B: Time-course monitoring of total polyamine content in NA and LA plants grown in the greenhouse. Leaf samples were collected from leaves at the same stage of development: before flowering (leaf 12), at topping (leaf 19) and at harvest leaf (24). Root samples were collected at topping and harvest. Values are means of three (A)/four (B) biological replicates. Error bars represent standard deviations of the mean. Statistical difference to NA is shown: *p<0.05; **p<0.005. PA: polyamine; FW: fresh weight.

To minimize the effect of variable environmental factors on polyamine biosynthesis, further experiments were performed under controlled greenhouse conditions mirroring the average field conditions in terms of temperature, light and humidity (data not shown). The phenotypes of the NA and LA plants in the greenhouse at harvest (30 days post-topping) were similar to their counterparts grown in the field in terms of plant height, leaf number and leaf morphology (data not shown). The impact of wounding on polyamine biosynthesis was minimized by designing the experiments so that each leaf/root sample was collected only once per plant and time point. Time-course monitoring of the total polyamine content in leaves at the same developmental stage—i.e. leaf 12 before flowering, leaf 19 at topping and leaf 24 at harvest—revealed significantly ($p<0.05$) higher levels of polyamines in the LA plants before flowering (1.5-fold) and at harvest (2.1-fold) compared to the NA controls (FIG. 2B). The LA plants also accumulated significantly ($p<0.05$) higher levels of total polyamines in the roots at topping (2.4-fold) and at harvest (1.4-fold) compared to the NA controls (FIG. 2B)

Example 9: Effect of the nic1nic2 Double Mutation on Polyamine Biosynthesis

Figures 3A, 3B:
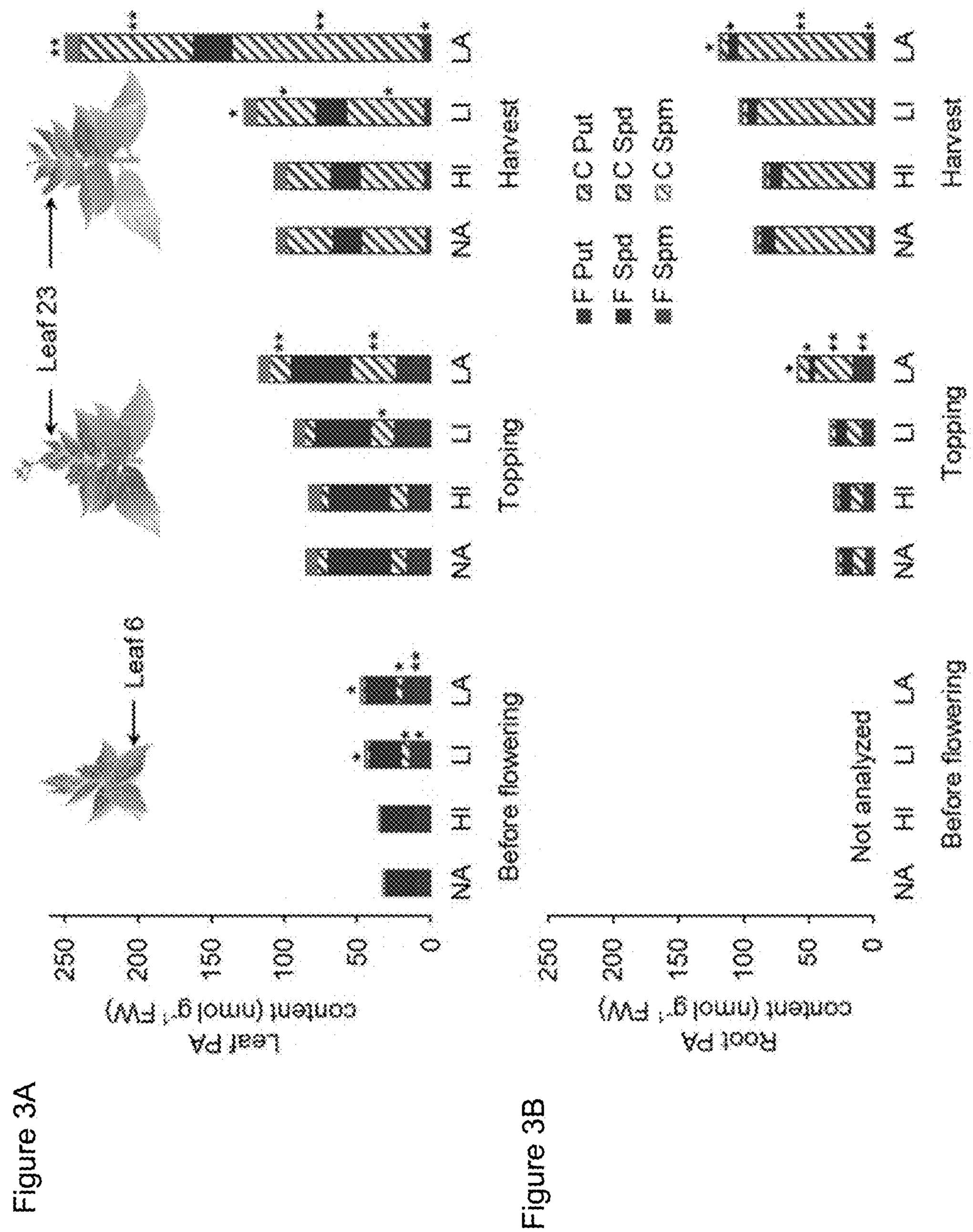
FIG. 3: Polyamine content in the leaves and roots of NA, HI, LI and LA plants grown in the greenhouse. Free (F) and conjugated (C) putrescine (Put), spermidine (Spd) and spermine (Spm) fractions in leaves (FIG. 3A) and roots (FIG. 3B) of NA, HI, LI and LA plants before flowering (leaf 6), at topping (young leaf 23, roots) and at harvest (matured leaf 23, roots) are shown. Samples were collected 4 h after illumination, frozen immediately in liquid nitrogen and analyzed by LC-MS/MS. Values are means of three biological replicates. Error bars represent standard deviations of the mean. Statistical difference is shown: *p<0.05; **p<0.001, indicating that the LI and LA plants are significantly different from NA plants under the same conditions. Only samples from topping and harvest were available for roots. FW: fresh weight.

Comparative analysis of the polyamine composition in selected leaves (leaf 6 before flowering, young leaf 23 at topping and mature leaf 23 at harvest) in the four varieties revealed that, before flowering, lines LI and LA contained significantly ($p<0.05$) higher levels of free putrescine than the NA controls (1.6-fold and 4.2-fold higher, respectively) and even higher levels of conjugated putrescine (2.1-fold and 5-fold higher, respectively) (FIG. 3A). The conjugated putrescine and spermidine fractions increased continuously during ripening in all four varieties, but remained significantly higher in LI and LA plants compared to NA controls (FIG. 3A). The greatest differential in polyamine content was observed in the LA leaves at harvest, with a 2.1-fold increase in the level of total polyamines compared to NA controls, including a 1.8-fold increase in free putrescine, a 2.9-fold increase in conjugated putrescine and a 2.4-fold increase in conjugated spermidine. However, there was no significant difference between the NA and HI varieties, indicating that the nic2 single mutation had a lower impact on polyamine accumulation.

At topping, the roots of the LA plants contained significantly ($p<0.05$) higher levels of free putrescine, conjugated putrescine and conjugated spermidine than the NA plants (2.6-fold, 2.9-fold and 2.5-fold increases, respectively) and such differences were also observed at harvest (1.6-fold, 1.4-fold and 2.5-fold increases, respectively) (FIG. 3B).

Figure 4A:
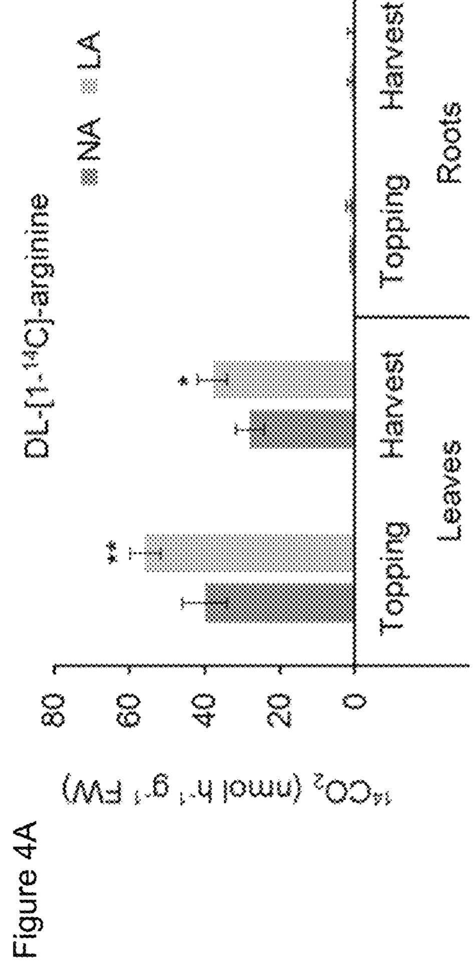
FIG. 4: Activity of polyamine biosynthesis enzymes. Analysis of arginine decarboxylase (ADC) (FIG. 4A) and ornithine decarboxylase (ODC) (FIG. 4B) activity in leaves and roots of NA and LA plants at topping (young leaf 23, roots) and harvest (matured leaf 23, roots). Values are means of three biological replicates. Error bars represent standard deviations of the mean. Statistical difference to NA is shown: *p<0.05; **p<0.001.
Figure 4B:
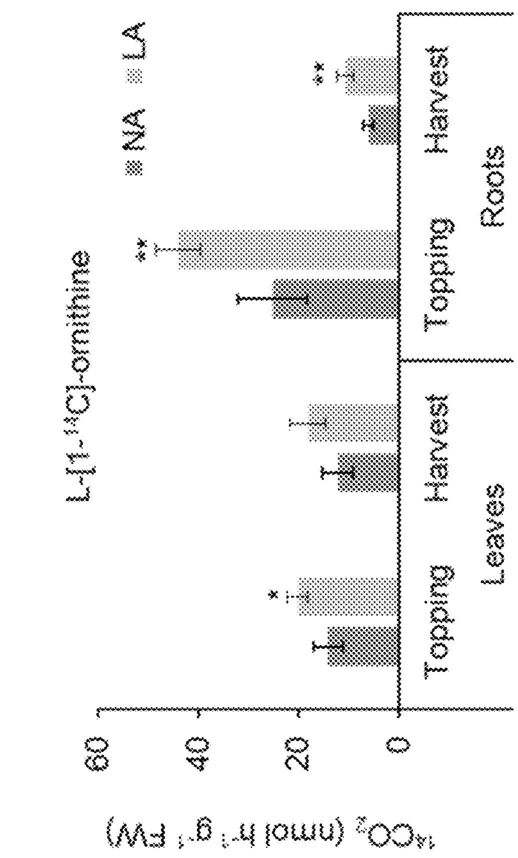

Example 10: The Polyamine Biosynthesis Pathway is More Active in the LA Plants The relative contribution of ADC and ODC to putrescine biosynthesis was evaluated by measuring the activity of each enzyme in the leaves (leaf 23) and roots of the NA and LA plants at topping and harvest. ADC and ODC activity varied in an organ-specific and developmental stage-specific manner in both lines (FIG. 4). Whereas ADC activity was high in the leaves but minimal in the roots of both lines, ODC activity was higher in the younger leaves and roots, indicating that ODC is mainly responsible for putrescine biosynthesis in the roots. ADC activity was significantly higher (1.4-fold, $p<0.05$) in the leaves of the LA plants compared to the NA controls at topping and harvest (FIG. 4A). Similarly, ODC activity was significantly higher ($p<0.05$) in the LA plants compared to the NA controls in the roots at topping (1.8-fold) and at harvest (1.7-fold), and in young leaves at topping (1.5-fold) (FIG. 4B).

Example 11: Inhibition of Polyamine Biosynthesis in the LA Variety

Given the correlation between the higher polyamine levels in the LA variety and the undesirable leaf morphology, the effect of treating the plants with chemicals that inhibit ADC and ODC was evaluated. Preliminary experiments defined the appropriate inhibitor concentration, application time, treatment intensity and duration (data not shown). The levels of free and conjugated putrescine were significantly higher in the LA plants than the NA controls before flowering and at harvest (FIG. 3), so the ADC inhibitor D-arginine and the ODC inhibitor difluoromethylornithine (DFMO) were applied beginning 2.5 weeks before topping and continued the treatment until harvest. In addition, the plant growth regulator Ethephon® was used alone or in combination with DFMO to accelerate ripening via the liberation of ethylene. To avoid the early induction of senescence, Ethephon® was applied from topping until harvest.

Figure 5:
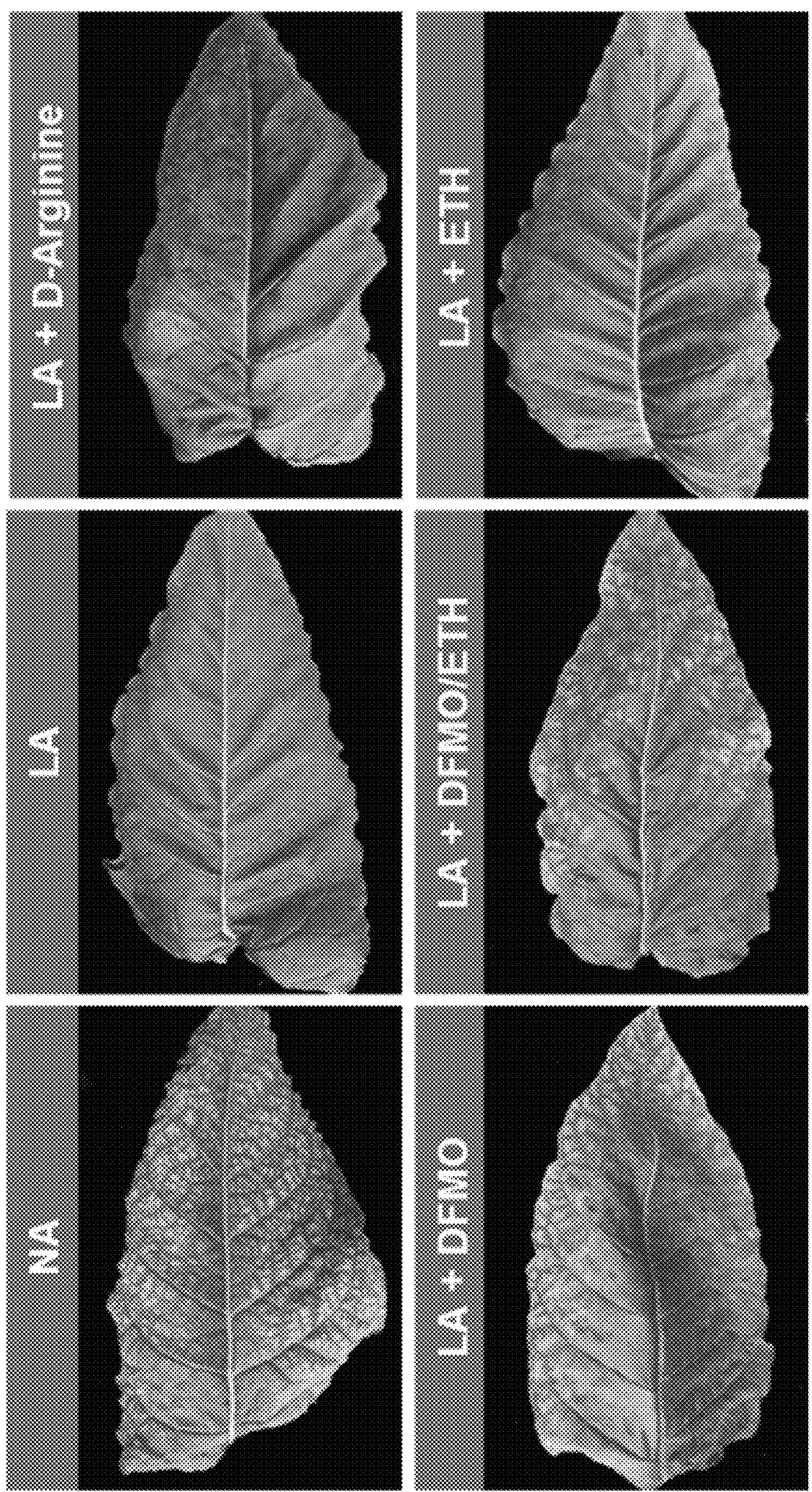
FIG. 5: Representative photos of leaf 23 from untreated NA and LA plants and LA plants treated with polyamine biosynthesis inhibitors and/or plant growth regulator at harvest. D-arginine (5 mM) is an inhibitor of ADC; DFMO (difluoromethylornithine, 2 mM) is an inhibitor of ODC, ETH (Ethephon®, 0.5 mM) is a growth regulator.

The DFMO and DFMO/Ethephon® treatments achieved a partial amelioration of the morphological phenotype, such that the leaves of the LA plants took on some of the characteristics of the NA leaves (wrinkling and chlorophyll degradation), whereas treatment with Ethephon® alone reduced the chlorophyll content but did not affect leaf morphology (FIG. 5). Starting the DFMO treatment before flowering resulted in growth arrest, which was not observed when the treatment was started at topping (data not shown). The D-arginine treatment had no effect on the chlorophyll level or morphology of the LA plants.

Figure 6A:
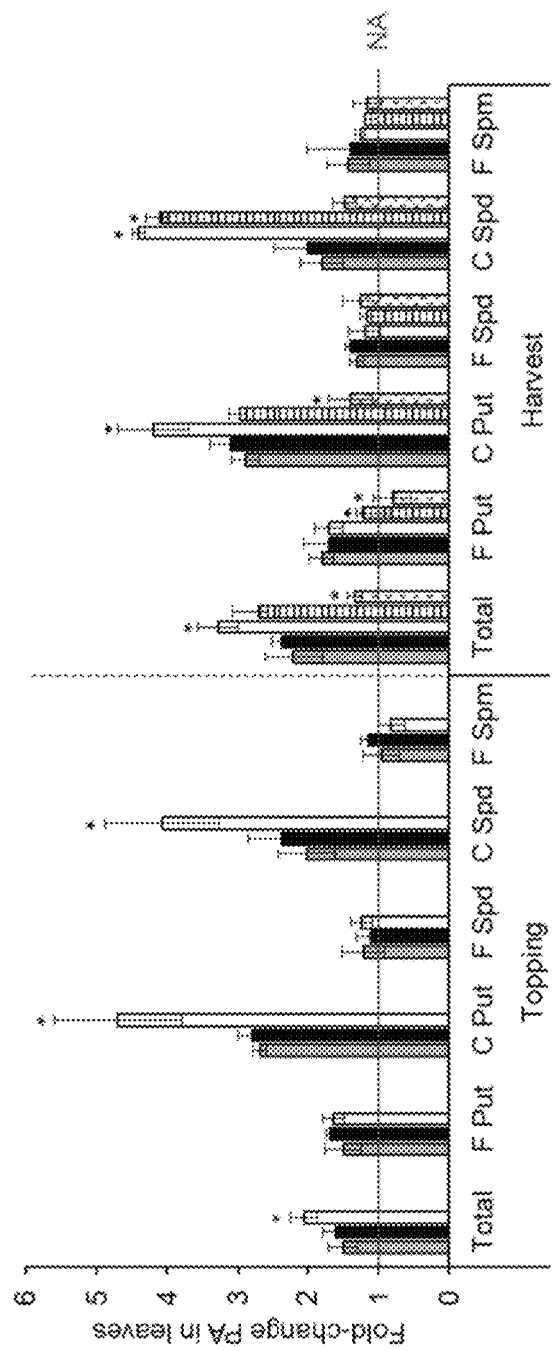
FIG. 6: Treatment of LA plants with polyamine biosynthesis inhibitors and/or Ethephon®. Comparative total, free and conjugated polyamine in leaves (FIG. 6A) and roots (FIG. 6B) of untreated and treated LA plants at topping and harvest. Tobacco plants were grown in the greenhouse in the absence (NA and LA) or presence (LA) of polyamine biosynthesis inhibitors and/or Ethephon® (5 mM D-arginine, 2 mM DFMO, 2 mM DFMO/0.5 mM Ethephon® or 0.5 mM Ethephon® alone). D-arginine and DFMO were applied three times per week from before flowering to harvest for a period of 6 weeks, whereas Ethephon® treatment started after topping (2.5 weeks later) until harvest. Samples were collected 4 h after illumination from leaf 23 or roots of four biological replicates per genotype or treatment. The fold change between the mean polyamine content from untreated LA plants (gray bars), or plants treated with D-arginine (black bars), DFMO (white bars), DFMO/Ethephon® (horizontal lined bars), and Ethephon® (divot bars) are plotted. Error bars represent standard deviations of the mean (n=4). Statistical difference to the mean of LA/NA is indicated: *p<0.05. The red line represents polyamine content in NA.
Figure 6B:
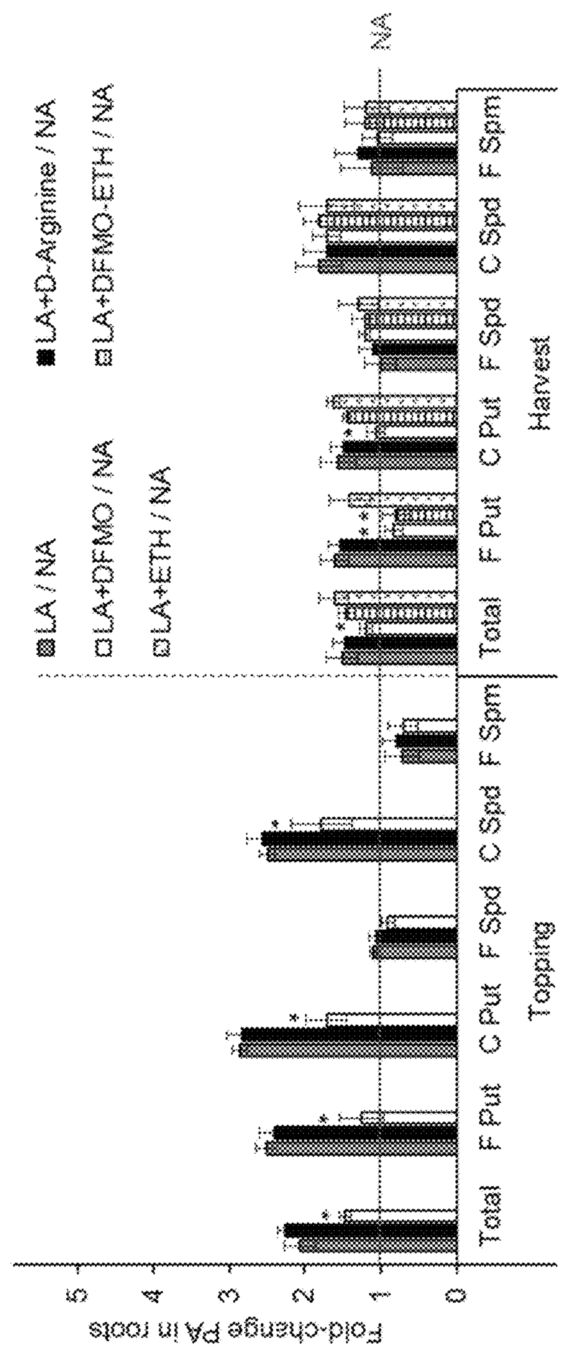

The analysis of polyamine levels revealed that the DFMO treatment 2.5 weeks before topping increased the levels of total polyamines in the LA leaves by 2.1-fold, mainly reflecting higher levels of conjugated putrescine and conjugated spermidine (FIG. 6A). This higher proportion of conjugated polyamines remained until harvest in the plants treated with DFMO and DFMO/Ethephon®. In contrast, the treatment with Ethephon® alone led to a significant reduction in total polyamine levels at harvest, mainly reflecting the reduction of free and conjugated putrescine. In the roots, the DFMO treatment significantly reduced ($p<0.05$) the total polyamine content of the LA plants at topping (1.5-fold) and at harvest (1.4-fold) due mainly to reduction of free and conjugated putrescine and conjugated spermidine (FIG. 6B). This decrease was not reversed by the addition of Ethephon®. In contrast to the effect in leaves, the application of Ethephon® alone had no effect on the polyamine content of the roots. The D-arginine treatment had no effect on the polyamine content of the LA plants. The loss of polyamines in the roots could therefore reflect the inhibition of ODC activity, the main enzyme responsible for putrescine biosynthesis in roots.

Example 12: Alteration of Polyamine Levels by Genetic Engineering

Modified tobacco plants are made to suppress ODC activity in a nic1 nic2 mutant background. A topping-responsive promoter (e.g., SED ID Nos: 1 to 21) is used to drive an ODC RNAi cassette (e.g., SEQ ID No: 22) to achieve the suppression of one or more ODC genes (e.g., coding sequences or protein sequences shown in SEQ ID Nos: 23 to 34). Transgenic plants are generated and assessed for leaf phenotypes, including for example, total leaf polyamine level, total root polyamine level, total leaf chlorophyll level, mesophyll cell number per leaf area unit, leaf epidermal cell size, and cured leaf grade.

Modified tobacco plants are also made to modulate the expression and activity of a MYB8 gene in a nic1 nic2 mutant Burley background. MYB8 was reported to control inducible phenolamide levels by activating three hydroxycinnamoyl-coenzyme A:polyamine transferases in *Nicotiana attenuata*. See Onkokesung et al., Plant Physiology 158 (1) 389-407 (2012). A constitutive promoter or a topping-responsive promoter (e.g., SED ID Nos: 1 to 21) is used to drive an MYB8 RNAi cassette or an MYB8 cDNA sequence to achieve suppression or overexpression, respectively. Transgenic plants are generated and assessed for leaf phenotypes, including for example, total leaf polyamine level, total root polyamine level, total leaf chlorophyll level, mesophyll cell number per leaf area unit, leaf epidermal cell size, and cured leaf grade.

Example 13: A Breeding Population

Low-alkaloid tobacco hybrids, varieties, or lines can be made as a Burley type, a dark type, a flue-cured type, a Maryland type or an Oriental type tobacco, or can be essentially derived from BU 64, CC 101, CC 200, CC 27, CC 301, CC 400, CC 500, CC 600, CC 700, CC 800, CC 900, Coker 176, Coker 319, Coker 371 Gold, Coker 48, CU 263, DF911, Galpao tobacco, GL 26H, GL 350, GL 600, GL 737, GL 939, GL 973, HB 04P, K 149, K 326, K 346, K 358, K394, K 399, K 730, KDH 959, KT 200, KT204LC, KY 10, KY 14, KY 160, KY 17, KY 171, KY 907, KY907LC, KTY14×L8 LC, Little Crittenden, McNair 373, McNair 944, msKY 14×L8, Narrow Leaf Madole, NC 100, NC 102, NC 2000, NC 291, NC 297, NC 299, NC 3, NC 4, NC 5, NC 6, NC7, NC 606, NC 71, NC 72, NC 810, NC BH 129, NC 2002, Neal Smith Madole, OXFORD 207, ‘Perique’ tobacco, PVH03, PVH09, PVH19, PVH50, PVH51, R 610, R 630, R 7-11, R 7-12, RG 17, RG 81, RG H51, RGH 4, RGH 51, RS 1410, Speight 168, Speight 172, Speight 179, Speight 210, Speight 220, Speight 225, Speight 227, Speight 234, Speight G-28, Speight G-70, Speight H-6, Speight H20, Speight NF3, TI 1406, TI 1269, TN 86, TN86LC, TN 90, TN 97, TN97LC, TN D94, TN D950, TR (Tom Rosson) Madole, VA 309, or VA359, Maryland 609, HB3307PLC, HB4488PLC, KT206LC, KT209LC, KT210LC, KT212LC, R610LC, PVH2310, NC196, KTD14LC, KTD6LC, KTD8LC, PD7302LC, PD7305LC, PD7309LC, PD7318LC, PD7319LC, PD7312LC, ShireyLC, or any commercial tobacco variety according to standard tobacco breeding techniques known in the art.

The invention claimed is:

1. A tobacco plant comprising a *nic*1 *nic*2 genotype and further comprising a topping inducible promoter operably linked to a transcribable DNA sequence encoding a non-coding RNA for suppression of an ornithine decarboxylase (ODC) gene having at least 90% identity to a sequence selected from the group consisting of SEQ ID NOs: 23, 24, 25, 26, 27, and 28.

2. The tobacco plant of claim 1, wherein said tobacco plant is capable of producing a leaf comprising a level of one or more polyamines within at least 20% relative to a comparable leaf of a control plant not comprising said topping inducible promoter operably linked to a transcribable DNA sequence encoding a non-coding RNA for suppression of an ornithine decarboxylase (ODC) gene.

3. The tobacco plant of claim 1, wherein said tobacco plant is capable of producing a leaf comprising a chlorophyll level within at least 20% relative to a comparable leaf of a control plant not comprising said topping inducible promoter operably linked to a transcribable DNA sequence encoding a non-coding RNA for suppression of an ornithine decarboxylase (ODC) gene.

4. The tobacco plant of claim 1, wherein said tobacco plant is capable of producing a leaf comprising a number of mesophyll cells per unit of leaf area within at least 20% relative to a comparable leaf of a control plant not comprising said topping inducible promoter operably linked to a transcribable DNA sequence encoding a non-coding RNA for suppression of an ornithine decarboxylase (ODC) gene.

5. The tobacco plant of claim 1, wherein said tobacco plant is capable of producing a leaf comprising a epidermal cell size within at least 20% relative to a comparable leaf of a control plant not comprising said topping inducible promoter operably linked to a transcribable DNA sequence encoding a non-coding RNA for suppression of an ornithine decarboxylase (ODC) gene.

6. The tobacco plant of claim 1, wherein said tobacco plant comprises a leaf yield within at least 20% relative to a comparable leaf of a control plant not comprising said topping inducible promoter operably linked to a transcribable DNA sequence encoding a non-coding RNA for suppression of an ornithine decarboxylase (ODC) gene.

7. The tobacco plant of claim 1, wherein said ornithine decarboxylase (ODC) gene encodes a polypeptide sequence having at 90% identity to a sequence selected from the group consisting of SEQ ID NOs: 29, 30, 31, 32, 33, and 34.

8. The tobacco plant of claim 7, wherein said ODC gene comprises a nucleotide sequence having at least 95% identity to a sequence selected from the group consisting of SEQ ID NOs: 23, 24, 25, 26, 27, and 28.

9. The tobacco plant of claim 1, wherein said inducible promoter comprises a sequence selected from the group consisting of SEQ ID NOs: 1, 2, 3, 4, 5, 6, 7, 8, 9, 10, 11, 12, 13, 14, 15, 16, 17, 18, 19, 20, and 21.

10. The tobacco plant of claim 1, wherein said non-coding RNA comprises a nucleotide sequence having at least 95% identity to a sequence selected from the group consisting of SEQ ID NOs: 35 and 36.

11. The tobacco plant of claim 10, wherein said non-coding RNA is provided in an ODC RNAi construct comprising a nucleotide sequence having at least 95% identity to SEQ ID NO: 22.

12. Cured tobacco material from the tobacco plant of claim 1.

13. A tobacco product comprising the cured tobacco material of claim 12.

14. The tobacco product of claim 13, wherein said tobacco product is selected from the group consisting of a cigarette, a cigarillo, a non-ventilated recess filter cigarette, a vented recess filter cigarette, a cigar, snuff, pipe tobacco, cigar tobacco, cigarette tobacco, chewing tobacco, leaf tobacco, shredded tobacco, loose leaf chewing tobacco, plug chewing tobacco, moist snuff, nasal snuff, and cut tobacco.

15. The tobacco plant of claim 1, wherein said ornithine decarboxylase (ODC) gene encodes a polypeptide sequence having at least 95% identity to a sequence selected from the group consisting of SEQ ID NOs: 29, 30, 31, 32, 33, and 34.

16. The tobacco plant of claim 7, wherein said ODC gene comprises a nucleotide sequence having at least 99% identity to a sequence selected from the group consisting of SEQ ID NOs: 23, 24, 25, 26, 27, and 28.

17. The tobacco plant of claim 1, wherein said non-coding RNA comprises a nucleotide sequence having at least 99% identity to a sequence selected from the group consisting of SEQ ID NOs: 35 and 36.

18. The tobacco plant of claim 10, wherein said non-coding RNA is provided in an ODC RNAi construct comprising a nucleotide sequence having at least 99% identity to SEQ ID NO: 22.

* * * * *